United States Patent
Shay et al.

(10) Patent No.: US 12,070,472 B2
(45) Date of Patent: Aug. 27, 2024

(54) TREATMENT OF DRUG RESISTANT PROLIFERATIVE DISEASES WITH TELOMERASE MEDIATED TELOMERE ALTERING COMPOUNDS

(71) Applicant: The Board of Regents of the University of Texas System, Austin, TX (US)

(72) Inventors: Jerry Shay, Dallas, TX (US); Ilgen Mender, Dallas, TX (US); Kimberly Batten, Dallas, TX (US); Sergei Gryaznov, Chicago, IL (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/450,430

(22) Filed: Jun. 24, 2019

(65) Prior Publication Data
US 2019/0388453 A1 Dec. 26, 2019

Related U.S. Application Data

(63) Continuation of application No. 15/467,862, filed on Mar. 23, 2017, now abandoned.

(60) Provisional application No. 62/312,982, filed on Mar. 24, 2016.

(51) Int. Cl.
| *A61K 31/7076* | (2006.01) |
| *A61K 9/00* | (2006.01) |
| *A61K 31/7105* | (2006.01) |
| *A61K 45/06* | (2006.01) |

(52) U.S. Cl.
CPC ........ *A61K 31/7076* (2013.01); *A61K 9/0019* (2013.01); *A61K 31/7105* (2013.01); *A61K 45/06* (2013.01)

(58) Field of Classification Search
CPC ........................ A61K 31/7076; A61K 31/7105
See application file for complete search history.

(56) References Cited

U.S. PATENT DOCUMENTS

| 7,989,428 B2 * | 8/2011 | Go | A61K 31/7068 514/44 R |
| 7,998,938 B2 * | 8/2011 | Moore | A61K 31/454 514/44 R |
| 2011/0059186 A1 * | 3/2011 | Burger | A61K 33/36 424/623 |
| 2014/0030255 A1 | 1/2014 | Loboda et al. | |
| 2014/0303239 A1 * | 10/2014 | Shay | A61P 35/00 514/48 |

FOREIGN PATENT DOCUMENTS

| KR | 10-2012-0064448 | | 6/2012 |
| KR | 102012006448 | * | 6/2012 |
| WO | WO 1998/02581 | * | 1/1998 |

OTHER PUBLICATIONS

Awad, M.M. et al. (2013) Acquired resistance to crizotinib from a mutation in CD74-ROS1. N. Engl. J. Med. 368, 2395-2401.
Basile KJ, et al. Adaptive up-regulation of FOXD3 and resistance to PLX4032/4720 induced cell death in mutant B-RAF melanoma cells. Oncogene 2011; 31(19):2471-2479.
Bauer, S. et al. (2014) Phase I study of panobinostat and imatinib in patients with treatment-refractory metastatic gastrointestinal stromal tumors. Br. J.Cancer 110, 1155-1162.
Bivona TG, et al. FAS and NF-kappaB signaling modulate dependence of lung cancers on mutant EGFR. Nature 2011;471(7339):523-6 Epub Mar. 25, 2011.
Blackburn EH, (2005) Telomerase and Cancer, Molecular Cancer Research 3:477-482.
Blasco, M. A. (2005). Telomeres and human disease: Ageing, cancer and beyond. Nature Reviews Genetics 6(8), 611-622.
Bodnar, A.G., et al. (1998) Extension of life-span by introduction of telomerase into normal human cells. Science, 279, 349-352.
Camp ER, et al., Molecular mechanisms of resistance to therapies targeting the epidermal growth factor receptor. Clin Cancer Res 2005;11(1):397-405.
Chakravarti A, et al. Insulin-like growth factor receptor I mediates resistance to anti-epidermal growth factor receptor therapy in primary human glioblastoma cells through continued activation of phosphoinositide 3-kinase signaling. Cancer Res 2002;62(1):200-7.
Cheung HW, et al., Amplification of CRKL induces transformation and EGFR inhibitor resistance in human non-small cell lung cancers. Cancer Discov. 2011;1(7):608-25.
Costa C, et al. The Impact of EGFR T790M Mutations and BIM mRNA Expression on Outcome in Patients with EGFR-Mutant NSCLC Treated with Erlotinib or Chemotherapy in the Randomized Phase III Eurtac Trial. Clin Cancer Res. 2014. Epub Feb. 5, 2014. Clin Cancer Res. Apr. 1, 2014;20(7), pp. 2001-2010.
Damiano, J. S. Integrins as novel drug targets for overcoming innate drug resistance. Curr. Cancer Drug Targets 2, 37-43 (2002).
De Bruin EC, et al. Reduced NF1 expression confers resistance to EGFR inhibition in lung cancer. Cancer Discov. 2014; 4(5): 606-19. doi: 10.1158/2159-8290. CD-13-0741.
Dean, M. (2009). ABC transporters, drug resistance, and cancer stem cells. Journal of Mammary Gland Biology and Neoplasia 14(1), 3-9.
Doyle, L. A. et al. A multidrug resistance transporter from human MCF-7 breast cancer cells. Proc. Natl Acad. Sci. USA 95, 15665-15670 (1998).
Duesberg, P., et al., Explaining the high mutation rates of cancer cells to drug and multidrug resistance by chromosome reassortments that are catalyzed by aneuploidy. Proc. Natl Acad. Sci. USA 97, 14295-14300 (2000).

(Continued)

*Primary Examiner* — Marcos L Sznaidman
(74) *Attorney, Agent, or Firm* — Parker Highlander PLLC

(57) ABSTRACT

The described invention is directed toward pharmaceutical compositions and methods of using 6-mercaptopurine ribosides and analogues thereof for the treatment of cancer and other hyperproliferative diseases. The described compounds can be converted into telomere substrates in vivo and can be recognized by telomerase for incorporation into telomeres of telomerase active cells, leading to induction of cell death of the telomerase active cells.

8 Claims, 30 Drawing Sheets

Specification includes a Sequence Listing.

(56) References Cited

OTHER PUBLICATIONS

Edwards, S. L. et al. Resistance to therapy caused by intragenic deletion in BRCA2. Nature 451, 1111-1115 (2008).
Emery CM, et al. MEK1 mutations confer resistance to MEK and B-RAF inhibition. Proc. Natl. Acad. Sci. 2009; 106(48):20411-20416.
Engelman JA, et al. MET amplification leads to gefitinib resistance in lung cancer by activating ERBB3 signaling. Science 2007;316(5827):1039-43.
Engelman, J.A. et al. (2006) Allelic dilution obscures detection of a biologically significant resistance mutation in EGFR-amplified lung cancer. J. Clin. Invest. 116, 2695-2706.
Ercan D, et al., Reactivation of ERK signaling causes resistance to EGFR kinase inhibitors. Cancer Discov 2012;2(10):934-47.
Farmer, H. et al. Targeting the DNA repair defect in BRCA mutant cells as a therapeutic strategy. Nature 434, 917-921 (2005).
Fink, D., et al., The role of DNA mismatch repair in drug resistance. Clin. Cancer Res. 4, 1-6 (1998).
Ford, L.P., et al. (2000) Heterogeneous nuclear ribonucleoproteins C1 and C2 associate with the RNA Component of human telomerase. Mol. Cell. Biol., 20, 9084-9091.
Gibney GT, et al., An Unholy Alliance: Cooperation between BRAF and NF1 in Melanoma Development and BRAF Inhibitor Resistance. Cancer Discov. 2013; 3(3):260-263.
Gilbert, L. A., et al., DNA damage-mediated induction of a chemoresistant niche. Cell 143, 355-366 (2010).
Girotti MR, et al., Inhibiting EGF Receptor or SRC Family Kinase Signaling Overcomes BRAF Inhibitor Resistance in Melanoma. Cancer Discov. 2013; 3(2):158-167.
Gorre, M. E. et al. (2001) Clinical resistance to STI—571 cancer therapy caused by BCR-ABL gene mutation or amplification. Science 293, 876-880.
Gottesman, MM, et al., Multidrug resistance in cancer: role of ATP-dependent transporters. Nature Rev. Cancer 2, 48-58 (2002).
Gowrishankar K, et al. Acquired resistance to BRAF inhibition can confer cross-resistance to combined BRAF/MEK inhibition. J. Invest. Dermatol. 2012; 132(7): 1850 1859.
Greider, C.W. and Blackburn, E.H. (1987) The telomere terminal transferase of Tetrahymena is a ribonucleoprotein enzyme with two kinds of primer specificity. Cell, 51, 887-898.
Griffith, J.D., et al. (1999) Mammalian telomeres end in a large duplex loop. Cell, 97, 503-514.
Gutova, M., et al. (2007) Identification of uPAR-positive chemoresistant cells in small cell lung cancer. PLoS One 2(2), 243.
Halvorsen, T.L., et al. (1999) Telomerase activity is sufficient to allow transformed cells to escape from crisis. Mol. Cell. Biol., 19,1864-1870.
Hauschild A et al., Dabrafenib in BRAF-mutated metastatic melanoma: a multicentre, open-label, phase 3 randomised controlled trial. The Lancet 2012; 380(9839):358-365.
Holohan C., et al., Cancer drug resistance: an evolving paradigm, Nature Rev. Cancer, Oct. 2013, vol. 13, 714-726.
Holt, S.E., et al. (1999) Functional requirement of p23 and Hsp90 in telomerase complexes. Genes Dev., 13, 817-826.
Hu, X, et al., Understanding the Genetic Mechanisms of Cancer Drug Resistance Using Genomic Approaches, Trends in Genetics, vol. 32, Issue 2, p. 127-137, Feb. 2016.
Huang S, et al. MED12 controls the response to multiple cancer drugs through regulation of TGF-beta receptor signaling. Cell 2012;151(5):937-50.
Joshi, M. et al., Taxanes, past, present, and future impact on non-small cell lung cancer, Anti-Cancer Drugs 25:571-583 (2014).
Kobayashi S, et al. EGFR mutation and resistance of non-small-cell lung cancer to gefitinib. N Engl J Med 2005; 352(8):786-92.
Kuang, L. S., & Zhou, X. D. (2013). The relationship between tumor stem cells marker CD90 and resistance to cisplatin in human lung adenocarcinoma A549 cells. Tumor 33(9), 770-775 (English Abstract).
Kyula, J. N. et al. Chemotherapy-induced activation of ADAM—17: a novel mechanism of drug resistance in colorectal cancer. Clin. Cancer Res. 16, 3378-3389 (2010).
Leon, G., et al., Cancer stem cells in drug resistant lung cancer: Targeting cell surface markers and signaling pathways, Pharmacol. Ther. 158, 71-90 (2016).
Letai, A. G. Diagnosing and exploiting cancer's addiction to blocks in apoptosis. Nature Rev. Cancer 8, 121-132 (2008).
Lito P, et al. Tumor adaptation and resistance to RAF inhibitors. Nat. Med. 2013; 19(11):1401-1409.
McArthur GA, et al. Safety and efficacy of vemurafenib in BRAFV600E and BRAFV600K mutation-positive melanoma (BRIM-3): extended follow-up of a phase 3, randomised, open-label study. Lancet Oncol. 2014; 15(3):323-332.
Mender et al., "A novel telomerase substrate precursor rapidly induces telomere dysfunction in telomerase positive cancer cells but not telomerase negative normal cells," Oncoscience, 2(8):693-695, 2015.
Mender et al., "Induction of telomere dysfunction mediated by the telomerase substrate precursor, 6-thio-2-deoxyguanosine," *Cancer Discovery*, 5(1):82-95, 2015.
Miyashita, T., et al., bcl-2 gene transfer increases relative resistance of S49.1 and WEHI7.2 lymphoid cells to cell death and DNA fragmentation induced by glucocorticoids and multiple chemotherapeutic drugs. Cancer Res. 52, 5407-5411 (1992).
Montagut, C. et al. (2012) Identification of a mutation in the extracellular domain of the epidermal growth factor receptor conferring cetuximab resistance in colorectal cancer. Nat. Med. 18, 221-223.
Monzo M, et al., Paclitaxel resistance in non-small-cell lung cancer associated with beta-tubulin gene mutations. J Clin Oncol 1999; 17:1786-1793.
Nakamura, T.M., et al. (1997) Telomerase catalytic subunit homologs from fission yeast and human. Science, 277, 955-959.
Nathanson KL, et al., Tumor Genetic Analyses of Patients with Metastatic Melanoma Treated with the BRAF Inhibitor Dabrafenib (GSK2118436). Clin. Cancer Res. 2013; 19(17):4868-4878.
NG KP, et al. A common BIM deletion polymorphism mediates intrinsic resistance and inferior responses to tyrosine kinase inhibitors in cancer. Nat Med 2012;18(4):521-8.
Niederst, MJ. and Engelman, J.A. (2013) Bypass mechanisms of resistance to receptor tyrosine kinase inhibition in lung cancer. Sci. Signal. 6(294).
Nooter, K. et al. The prognostic significance of expression of the multidrug resistance- associated protein (MRP) in primary breast cancer. Br. J. Cancer 76, 486-493 (1997).
Office Action issued in U.S. Appl. No. 15/467,862, mailed Jan. 12, 2018.
Office Action issued in U.S. Appl. No. 15/467,862, mailed May 29, 2018.
Office Action issued in U.S. Appl. No. 15/467,862, mailed Nov. 2, 2018.
Ohashi K, et al., Lung cancers with acquired resistance to EGFR inhibitors occasionally harbor BRAF gene mutations but lack mutations in KRAS, NRAS, or MEK1. Proc Natl Acad Sci USA 2012;109(31):E2127-33 [Epub Jul. 10, 2012].
Paraiso KHT, et al. PTEN Loss Confers BRAF Inhibitor Resistance to Melanoma Cells through the Suppression of BIM Expression. Cancer Res. 2011; 71(7):2750-2760.
PCT International Search Report and Written Opinion issued in International Application No. PCT/US2017/023858, mailed Jun. 20, 2017.
Poulikakos PI, et al. RAF inhibitor resistance is mediated by dimerization of aberrantly spliced BRAF(V600E). Nature 2011; 480(7377):387-390.
Poulikakos PI, et al., Mutant BRAF Melanomas- Dependence and Resistance. Cancer Cell 2011; 19(1):11-15.
Pusztai, L. et al. Phase II study of tariquidar, a selective P-glycoprotein inhibitor, in patients with chemotherapy resistant, advanced breast carcinoma. Cancer 104, 682-691 (2005).
Reyes-Uribe et al., "Exploiting TERT dependency as a therapeutic strategy for NRAS mutant melanoma," Oncogene, 37:4058-4072, 2018.

(56) References Cited

OTHER PUBLICATIONS

Robey, R. W. et al. Inhibition of ABCG2- mediated transport by protein kinase inhibitors with a bisindolylmaleimide or indolocarbazole structure. Mol. Cancer Ther. 6, 1877-1885 (2007).

Rolfo, C., et al., Novel therapeutic strategies for patients with NSCLC that do not respond to treatment with EGFR inhibitors, Cancer Treatment Reviews 40 (2014) 990-1004.

Rosell R et al. Pretreatment EGFR T790M mutation and BRCA1 mRNA expression in erlotinib-treated advanced non-small-celliung cancer patients with EGFR mutations. Clin Cancer Res 2011;17(5):1160-8 Epub Jan. 15, 2011.

Ruff, P. et al. A randomized, placebo-controlled, double-blind phase 2 study of docetaxel compared to docetaxel plus zosuquidar (LY335979) in women with metastatic or locally recurrent breast cancer who have received one prior chemotherapy regimen. Cancer Chemotherapy Pharmacol. 64, 763-768 (2009).

Sakai, W. et al. Secondary mutations as a mechanism of cisplatin resistance in BRCA2—mutated cancers. Nature 451, 1116-1120 (2008).

Sengupta et al., "Induced telomere damage to treat telomerase expressing therapy-resistant pediatric brain tumors," *Mol Cancer Ther,*, 17(7):1504-1514, 2018.

Sequist, L.V. et al. (2011) Genotypic and histological evolution of lung cancers acquiring resistance to EGFR inhibitors. Sci. Transl. Med. 3, (75): 75ra26.

Sharma SV, et al. A chromatin-mediated reversible drug-tolerant state in cancer cell subpopulations. Cell 2010;141(1):69-80.

Shay J.W. and Bacchetti S., "A survey of telomerase activity in human cancer," European Journal of Cancer 1997; 33:787-91.

Shay, "New insights into melanoma development (perspective)," *Science*, 357:1358-1359, 2017.

Shervington, A., et al. Expression of multidrug resistance genes in normal and cancer stem cells. Cancer Invest. 26, 535-542 (2008).

Shi H, et al. (2012) Melanoma whole-exome sequencing identifies V600EB-RAF amplification-mediated acquired B-RAF inhibitor resistance. Nat. Commun.; 3:724.

Smalley KS, et al., Increased cyclin D1 expression can mediate BRAF inhibitor resistance in BRAF V600E-mutated melanomas. Mol. Cancer Ther. 2008; (9):2876-2883.

Spagnolo, F. et al., Overcoming resistance to BRAF inhibition in BRAF-mutated metastatic melanoma, Oncotarget, vol. 5, No. 21 10206-10221.

Straussman, R. et al. (2012) Tumor microenvironment induces innate RAF-inhibitor resistance through HGF secretion. Nature 487, 500-504.

Suda K, et al. (2009) EGFR T790M mutation: a double role in lung cancer cell survival? J Thorac Oncol; 4(1):1-4.

Sun C, et al. Reversible and adaptive resistance to BRAF(V600E) inhibition in melanoma. Nature 2014; 508(7494):118-122.

Szakacs, G et al. Predicting drug sensitivity and resistance: profiling ABC transporter genes in cancer cells. Cancer Cell 6, 129-137 (2004).

Takezawa K, et al. HER2 amplification: a potential mechanism of acquired resistance to EGFR inhibition in EGFR-mutant lung cancers that lack the second-site EGFR T790M mutation. Cancer Discov 2012;2(10):922-33.

Thomas, H. & Coley, H. M. Overcoming multidrug resistance in cancer: an update on the clinical strategy of inhibiting P-glycoprotein. Cancer Control 10, 159-165 (2003).

Triller, N., et al., Multidrug resistance in small cell lung cancer: expression of Pglycoprotein, multidrug resistance protein 1 and lung resistance protein in chemo-naive patients and in relapsed disease. Lung Cancer 54, 235-240 (2006).

Turke AB, et al. Preexistence and clonal selection of MET amplification in EGFR mutant NSCLC. Cancer Cell 2010;17(1):77-88 [Epub Feb. 5, 2010].

Van Allen EM et al., The Genetic Landscape of Clinical Resistance to RAF Inhibition in Metastatic Melanoma. Cancer Discov. 2014; 4(1):94-109.

Wagle N, et al. (2014) MAP Kinase Pathway Alterations in BRAF-Mutant Melanoma Patients with Acquired Resistance to Combined RAF/MEK Inhibition. Cancer Discov. 4(1):61-68.

Wagle N, et al. Dissecting Therapeutic Resistance to RAF Inhibition in Melanoma by Tumor Genomic Profiling. J. Clin. Oncol. 2011, 29(22):3085-3096.

Walsh, KM et al. (2014) Variants near TERT and TERC influencing telomere length are associated with highgrade glioma risk, Nature Genetics 46, 731-735.

Wang, Z. et al. (2015) Activation of the BMP-BMPR pathway conferred resistance to EGFR-TKIs in lung squamous cell carcinoma patients with EGFR mutations. Proc. Natl. Acad. Sci. U.S.A. 112, 9990-9995.

Whittaker SR, et al. A Genome-Scale RNA Interference Screen Implicates NF1 Loss in Resistance to RAF Inhibition. Cancer Discov. 2013; 3(3):350-362.

Wilson, T. R. et al. Widespread potential for growth factor-driven resistance to anticancer kinase inhibitors. Nature 487,505-509 (2012).

Yabuki N., et al., Gene amplification and expression in lung cancer cells with acquired paclitaxel resistance. Cancer Genet. Cytogenet. 2007; 173: 1-9.

Yano S, et al. Hepatocyte growth factor expression in EGFR mutant lung cancer with intrinsic and acquired resistance to tyrosine kinase inhibitors in a Japanese cohort. J Thorac Oncol 2011;6(12):2011-7.

Zalcberg, J. et al. MRP1 not MDR1 gene expression is the predominant mechanism of acquired multidrug resistance in two prostate carcinoma cell lines. Prostate Cancer Prostatic Dis. 3, 66-75 (2000).

Zeller, C. et al. (2012) Candidate DNA methylation drivers of acquired cisplatin resistance in ovarian cancer identified by methylome and expression profiling. Oncogene 31, 4567-4576.

Zhang et al., "Induction of Telomere Dysfunction Prolongs Disease Control of Therapy-Resistant Melanoma," *Clin Cancer Res*, 24(19):4771-4784, 2018.

Zhang, Y.W. et al. (2014) Integrated analysis of DNA methylation and mRNA expression profiling reveals candidate genes associated with cisplatin resistance in non-small cell lung cancer. Epigenetics 9, 896-909.

Zhang, Z. et al. (2012) Activation of the AXL kinase causes resistance to EGFR-targeted therapy in lung cancer. Nat. Genet. 44, 852-860.

Zhou, W. et al. NEK2 induces drug resistance mainly through activation of efflux drug pumps and is associated with poor prognosis in myeloma and other cancers. Cancer Cell 23, 48-62 (2013).

Mender et al., "Telomerase-Mediated Strategy for overcoming Non-Small Cell Lung Cancer Targeted Therapy and Chemotherapy Resistance", *NEOPlasia*, 20(8):826-837, 2018.

\* cited by examiner

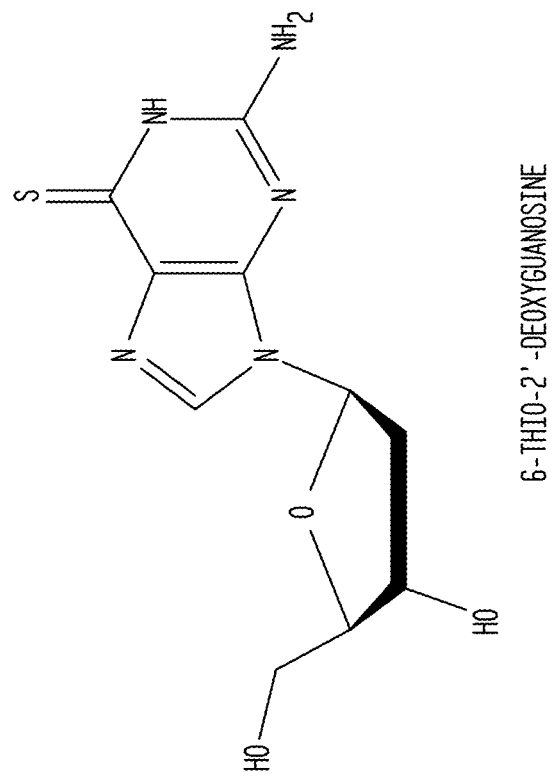
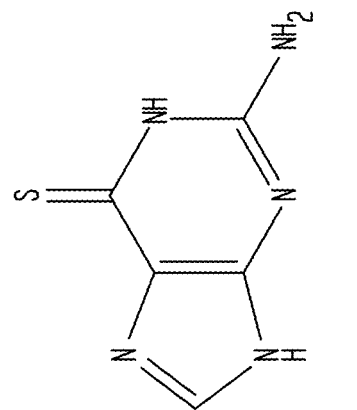
FIG. 1A

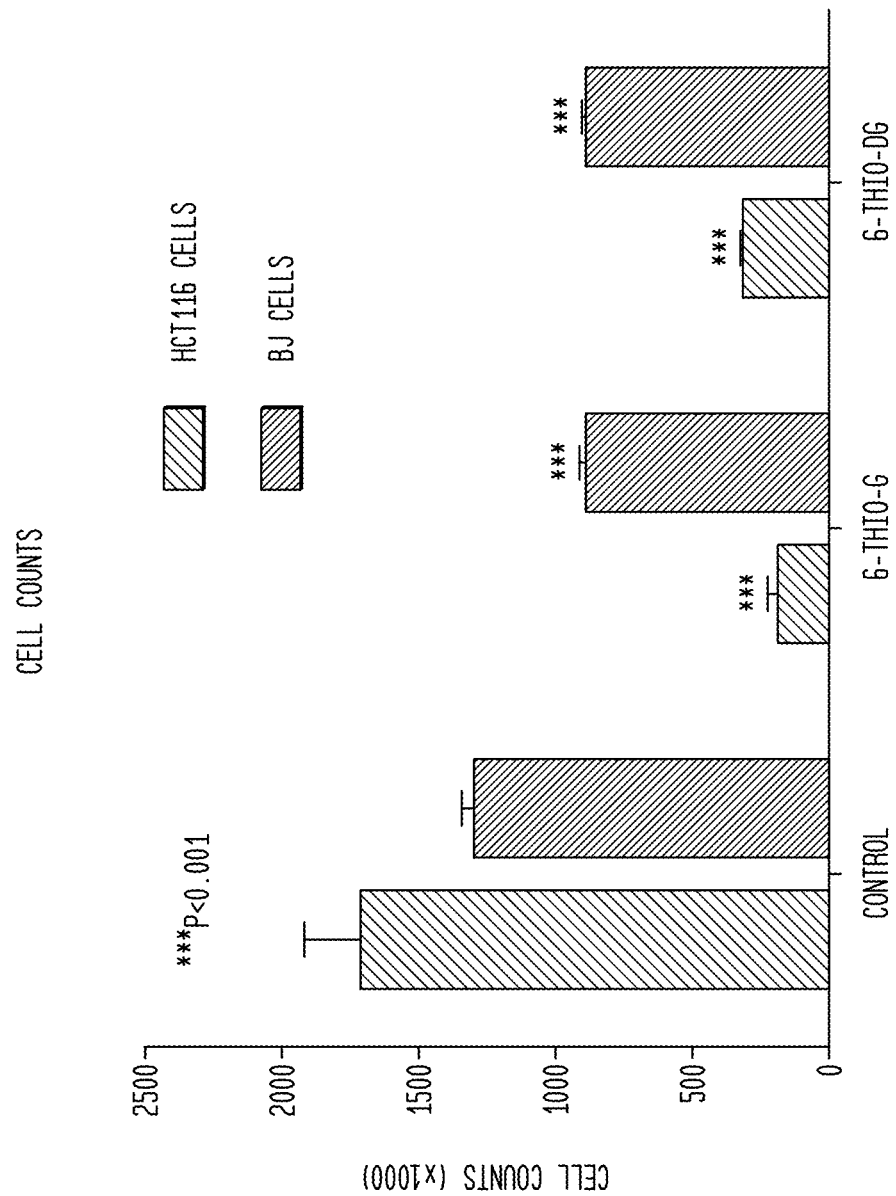

FIG. 2

| WEEK/SAMPLE | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| CONTROL | -- | -- | -- | -- | -- | -- | -- | -- | -- | -- | -- | -- | -- | -- | -- | -- |
| A | 1m | 1m | 1m | 1m | 1m | 1m | 1m | 1m | 1m | 1m | 1m | ■ | ■ | ■ | ■ | ■ |
| B | 6-dG | 6-dG | 6-dG | 6-dG | 6-dG | 6-dG | 6-dG | 6-dG | 6-dG | 6-dG | 6-dG | 6-dG | ■ | ■ | ■ | ■ |
| C | 6-dG | 6-dG | 6-dG | 6-dG | 6-dG | 6-dG | 6-dG | 6-dG | 6-dG | 6-dG | 6-dG | 6-dG | 6-dG | 6-dG | ■ | ■ |
| D | 6-dG | 6-dG | 6-dG | 6-dG | 6-dG | 6-dG | 6-dG | 6-dG | 6-dG | 6-dG | 6-dG | 6-dG | 6-dG | 6-dG | 6-dG | 6-dG |
| E | 6-dG | 6-dG | 6-dG | 6-dG | 6-dG | 6-dG | 6-dG | 6-dG | 6-dG | 6-dG | 6-dG | 6-dG | -- | -- | -- | -- |
| F | 6-dG | 6-dG | 6-dG | 6-dG | 6-dG | 6-dG | 6-dG | 6-dG | 6-dG | 6-dG | 6-dG | 6-dG | -- | -- | ■ | ■ |
| G | 6-dG | 6-dG | 6-dG | 6-dG | 6-dG | 6-dG | 6-dG | 6-dG | 6-dG | 6-dG | 6-dG | 6-dG | COMBO | COMBO | COMBO | COMBO |
| H | 6-dG | 6-dG | 6-dG | 6-dG | 6-dG | 6-dG | 6-dG | 6-dG | 6-dG | 6-dG | 6-dG | 6-dG | COMBO | COMBO | ■ | ■ |
| I | 6-dG | 6-dG | 6-dG | 6-dG | 6-dG | 6-dG | 6-dG | 6-dG | 6-dG | 6-dG | 6-dG | 6-dG | 1m | 1m | 1m | 1m |
| F | 6-dG | 6-dG | 6-dG | 6-dG | 6-dG | 6-dG | 6-dG | 6-dG | 6-dG | 6-dG | 6-dG | 6-dG | 1m | 1m | 1m | 1m |

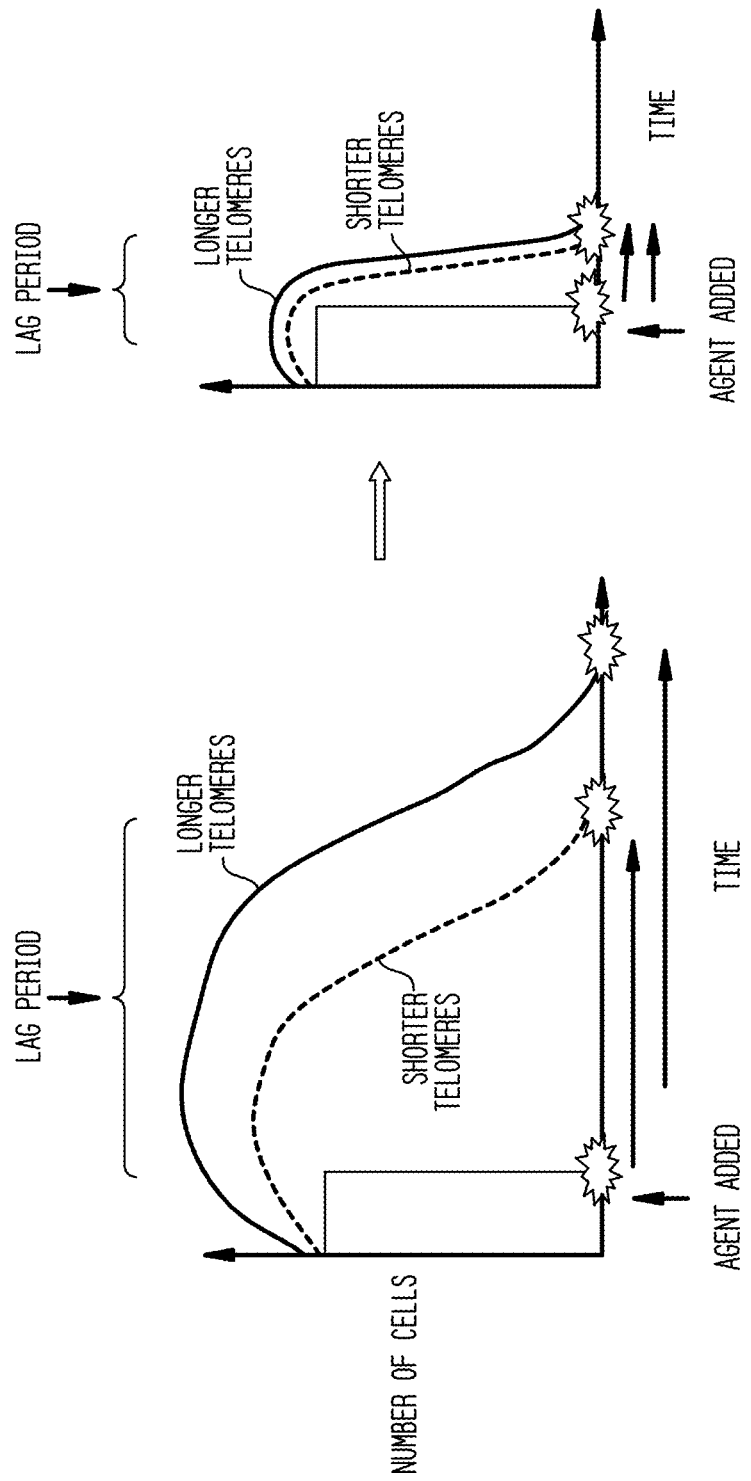

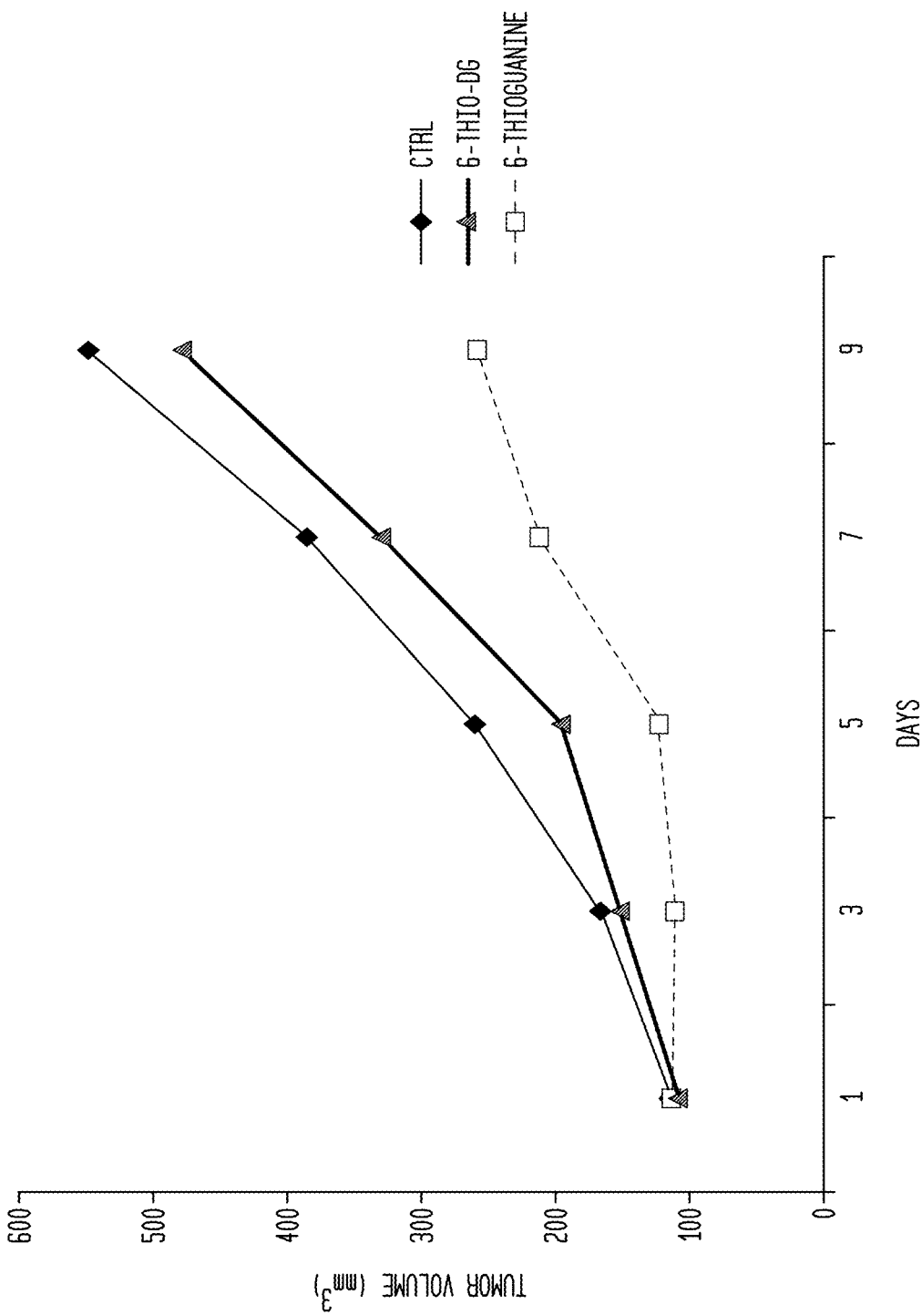

FIGURE SHOWS THE IC50 VALUES OF HCT116 COLON (A), A549 NON-SMALL CELL LUNG CANCER (B), HCEC1 HUMAN COLONIC EPITHELIAL (C) AND BJ NORMAL FIBROBLAST (D) CELLS. WE USED NINE DIFFERENT DOSES OF 6-THIO-DG WITH SERIAL DILUTIONS AND FOUND THAT WHILE HCT116 AND A549 TELOMERASE POSITIVE CANCER CELLS ARE SENSITIVE TO 6-THIO-DG (LOW IC50), HCEC1 AND BJ NORMAL (TELOMERASE SILENT) CELLS ARE NOT SENSITIVE TO 6-THIO-DG.

GENE EXPRESSION DIFFERENCES OF 6-THIO-DG SENSITIVE AND RESISTANT CELL LINES
BONFERRONI ADJUSTED P<0.01:906 PROBES (667 GENES)

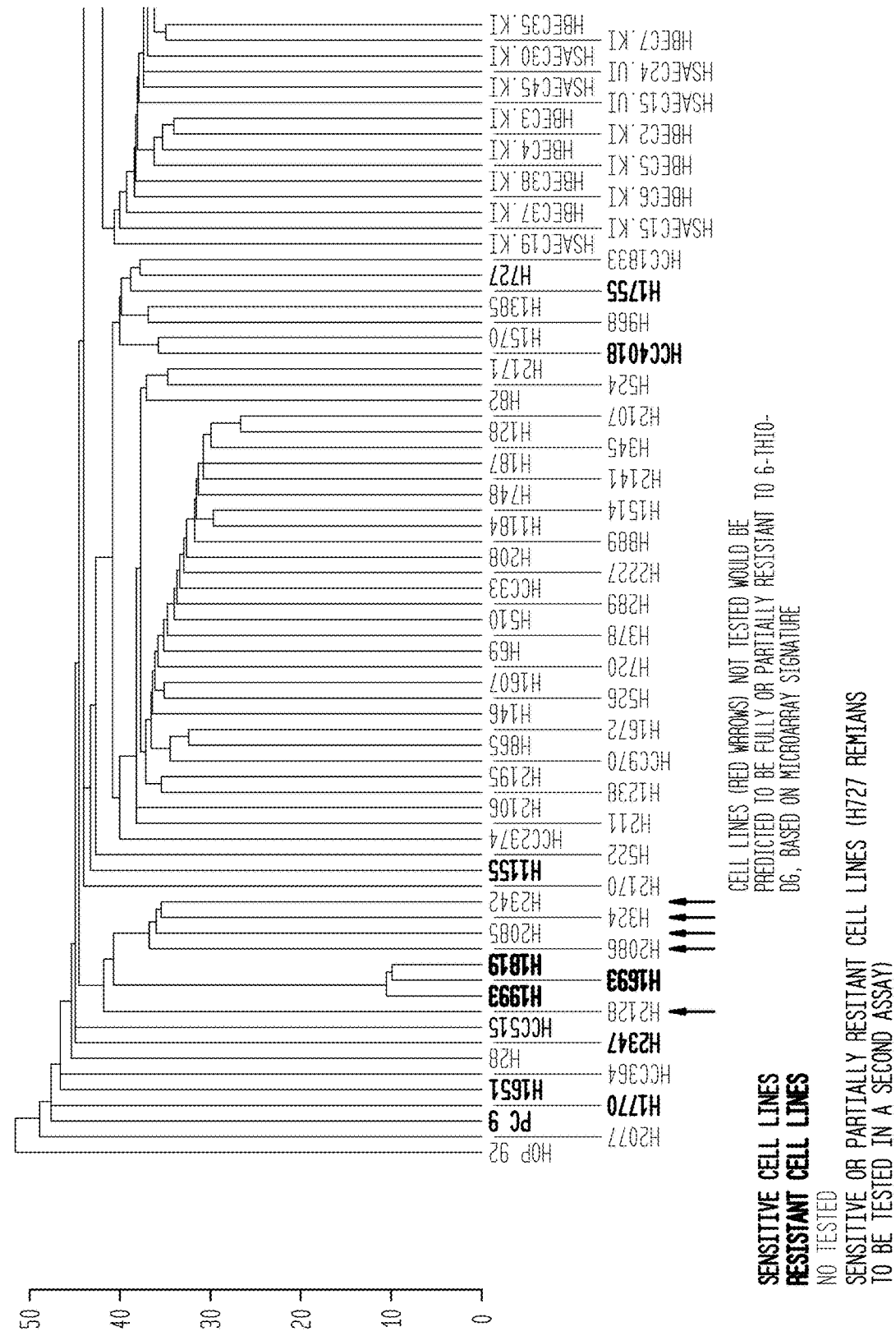

THE VAST MAJORITY (67/71) TESTED NSCLC CELL LINES ARE SENSITIVE TO 6-THIO-DG

SENSITIVE CELL LINES
NO TESTED
SENSITIVE OR PARTIALLY RESITANT CELL LINES (A549 IS PROBABLY SENSITIVE BUT ONE ASSAY INDICATED IT WAS PARTIALLY RESISTANT)

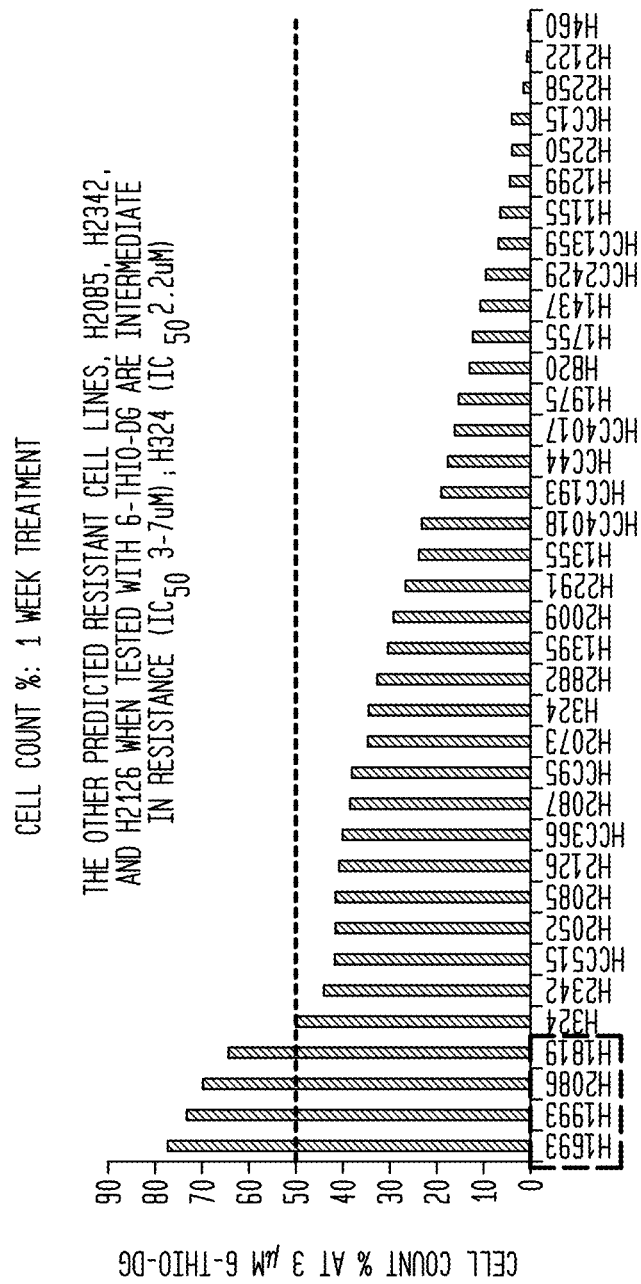

FIG. 13

USING A DIFFERENT ASSAY WE HAVE CONFIRMED RESISTANT AND SENSITIVE CELL LINES (3-4 DAYS TREATMENT)

| CELL LINE | IC50 OF 6-THIO-DG (MICROMOLAR) | | CELL LINE | IC50 OF 6-THIO-DG (MICROMOLAR) |
|---|---|---|---|---|
| H1693 | 40 | RESISTANT CELLS | H2122 | 1.55 |
| H1993 | 34 | | H820 | 1.55 |
| H2086 | 11.5 | | CALU-3 | 1.5 |
| H1819 | 10.5 | | HCC1195 | 1.5 |
| A549 | 2.4-7.5 | IN THE MIDDLE | HCC461 | 1.5 |
| HCC515 | 7 | | H2087 | 1.45 |
| H727 | 6.8 | | HCC4006 | 1.44 |
| H3255 | 5.65 | | HCC1897 | 1.4 |
| H2009 | 5.55 | | H1975 | 1.3 |
| HCC4019 | 4.95 | | HCC44 | 1.2 |
| H1755 | 4.7 | | H157 | 1.15 |
| H2052 | 4.6 | | H1581 | 1.04 |
| H2085 | 4.35 | | H2882 | 1.04 |
| H2030 | 4.25 | | H1651 | 1.03 |
| H2126 | 3.4 | | H2110 | 1 |
| H322 | 3.35 | | H125 | 0.84 |
| SK-LU-1 | 3.35 | | CALU-6 | 0.81 |
| H1437 | 3.3 | | HCC366 | 0.785 |
| H358 | 2.95 | SENSITIVE CELLS | HCC2108 | 0.735 |
| H520 | 2.95 | | H1944 | 0.665 |
| HCC193 | 2.35 | | H1770 | 0.655 |
| HCC95 | 2.35 | | H2347 | 0.58 |
| HCC2814 | 2.35 | | H2073 | 0.52 |
| H2444 | 2.25 | | H661 | 0.505 |
| H324 | 2.1 | | H2250 | 0.49 |
| H441 | 2 | | PC9 | 0.44 |
| H2887 | 2 | | HCC827 | 0.415 |
| HCC4313 | 1.9 | | HCC4017 | 0.39 |
| HCC15 | 1.9 | | H2258 | 0.35 |
| H1355 | 1.75 | | HCC1359 | 0.35 |
| H1395 | 1.7 | | H920 | 0.31 |
| H647 | 1.7 | | A427 | 0.305 |
| H1155 | 1.7 | | H1666 | 0.275 |
| HCC2450 | 1.7 | | H1792 | 0.24 |
| HCC4018 | 1.7 | | HCC2429 | 0.205 |
| H460 | 1.65 | | H1373 | 0.17 |

H2085, H2126, HCC515, H2052 ARE IN THE MIDDLE GROUP WITH ONE TIME TREATMENT FOR 3-4 DAYS (THESE WERE ALSO IN THE MIDDLE GROUP WITH ONE WEEK TREATMENT (TWO TIMES)).

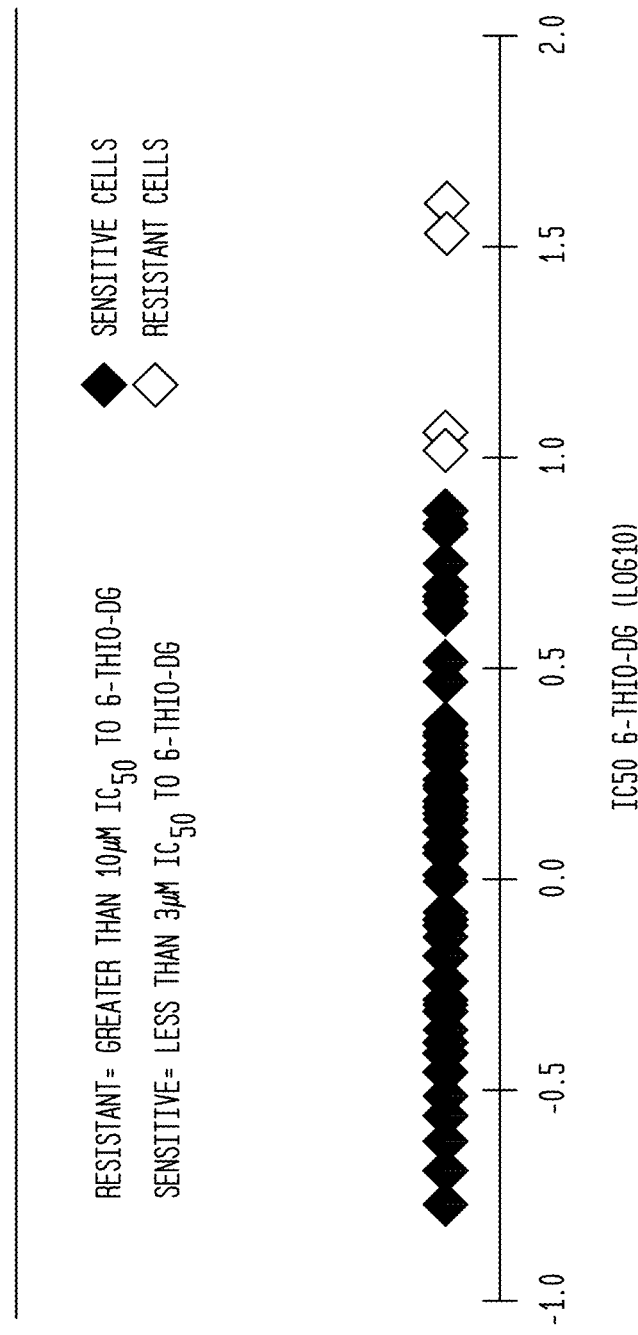

CLUSTER ANALYSIS ADDING ANOTHER 6-THIO-DG RESISTANT CELL LINE IMPROVED THE SEPARATION OF 6-THIO-DG RESISTANT NSCLC FROM SENSITIVE NSCLC CELL LINES

BONFERRONI ADJUSTED P<0.01: 444 RPOBES (354 GENES)

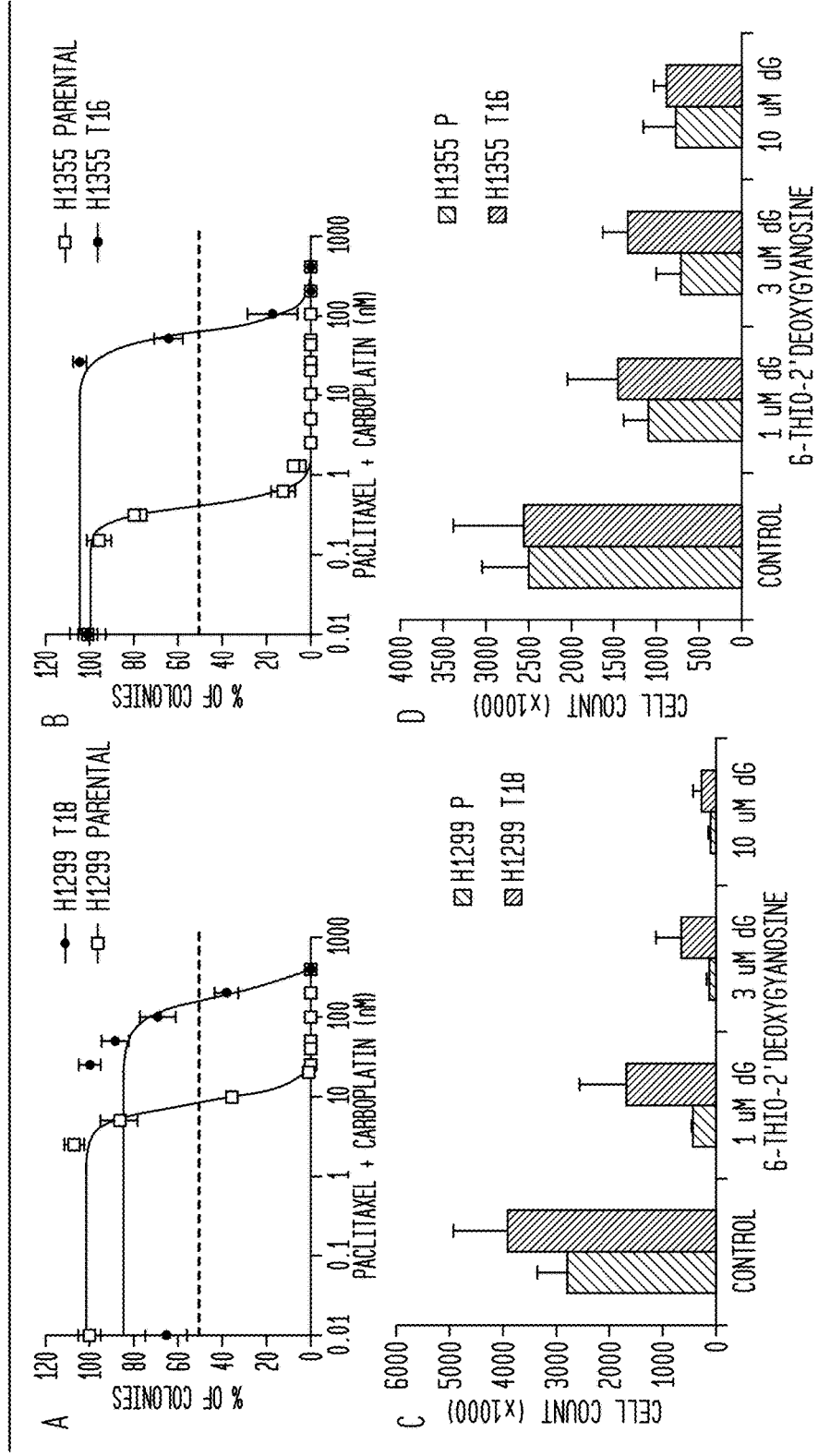

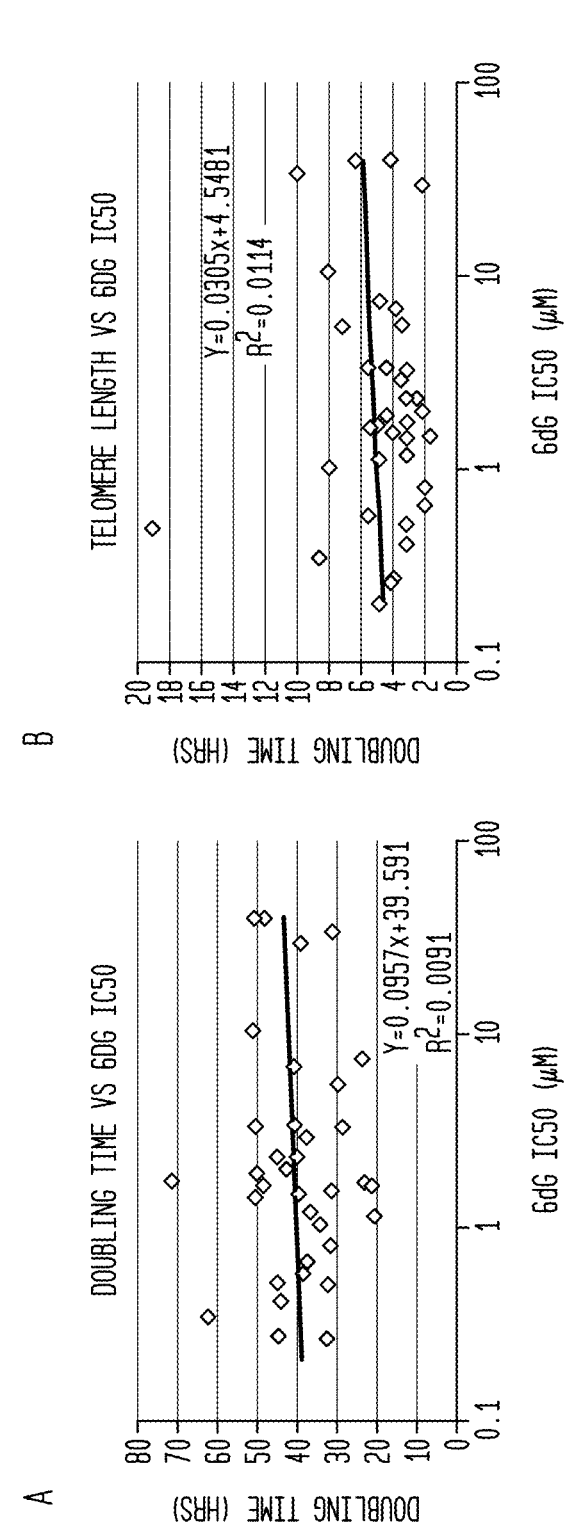

FIG. 17
6-THIO-DG CORRELATIONS

LACK OF CORRECTION OF CELL DOUBLING TIME (A) AND TELOMERE LENGTH (B) OF CELL LINES WITH 6-THIO-DG IC50 VALUES. A. EACH CELL LINES HAS SLIGHTLY DIFFERENT DOUBLING TIME (THE TIME THAT IS REQUIRED FOR CELLS TO DOUBLE IN POPULATION VALUE). NO CORRELATION WAS FOUND BETWEEN DOUBLING TIMES AND IC50 6-THIO-DG VALUES. THIS SHOWS THAT WHILE 6-THIO-DG KILLS FAST GROWING CELLS, THE CELLS THAT GROW SLOWER ARE ALSO SENSITIVE TO 6-THIO-DG. B. NO CORRELATION WAS FOUND BETWEEN TELOMERE LENGTH AND 6-THIO-DG IC50 VALUES. THIS ALSO SHOWS THAT THE EFFECT OF 6-THIO-DG IS INDEPENDENT FROM TELOMERE INITIAL LENGTH.

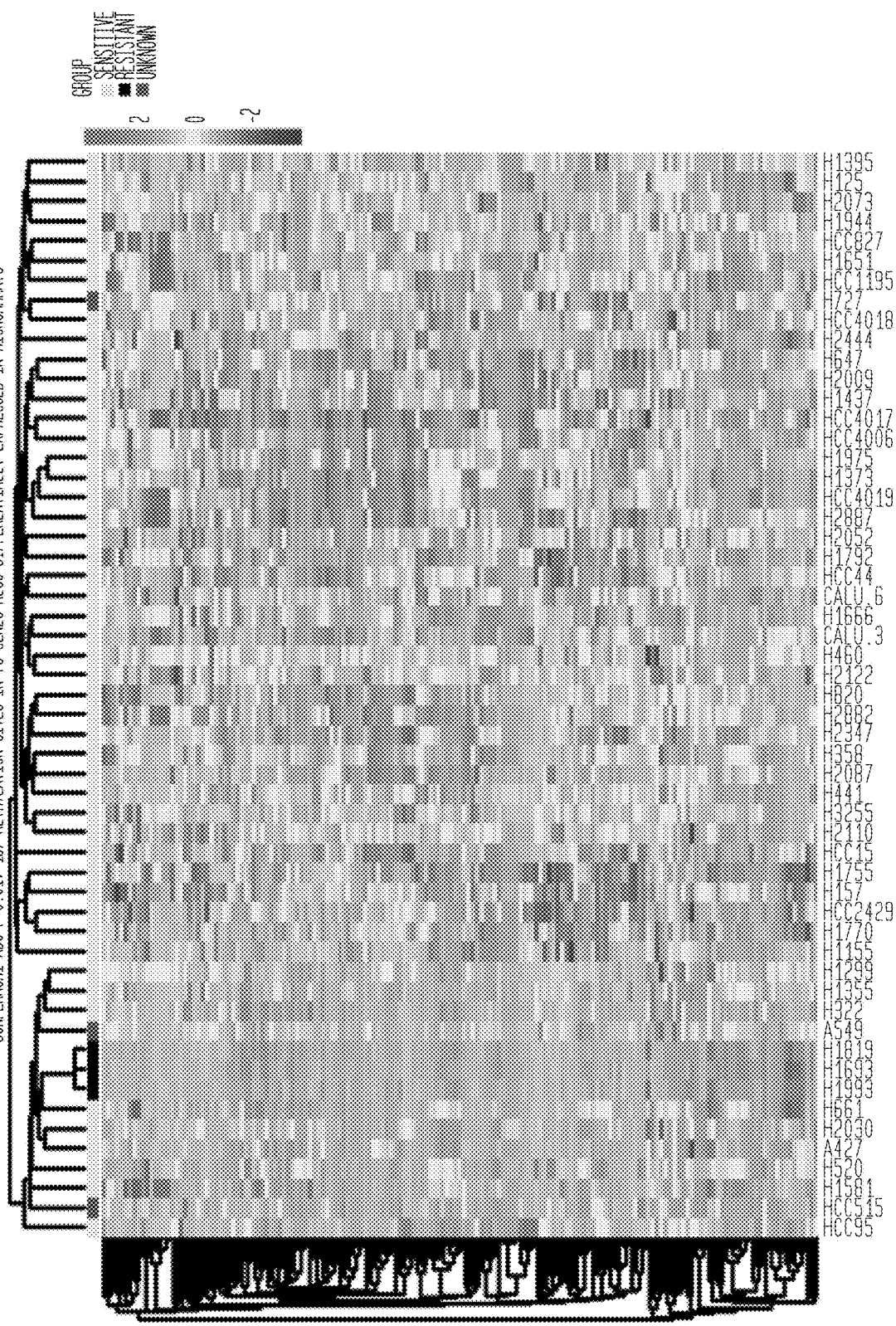

75 GENES ARE DIFFERENTIALLY EXPRESSED (HYPERMETHYLATED/SILENCED) IN GENE EXPRESSION AND METHYLATION INTEGRATIVE ANALYSIS
BONFERRONI ADJUSTED P<0.01: 82 PROBES (75 GENES) WITH EXPRESSION AND METHYLATION CHANGES

FIG. 20A

H1993 CELLS BECOMES SENSITIVE TO 6-THIO-DG AFTER 5-AZACYTIDINE PRETREATMENT

| ISOGENIC CELL LINES | 6-THIO-DG (µM) | 5-AZA PRETREATMENT (500 nM 1 WEEK) |
|---|---|---|
| H1693 | RESISTANCE (IC50>100 µM) | RESISTANCE (IC50>100 µM) |
| H1819 | RESISTANCE (IC50>100 µM) | RESISTANCE (IC50>100 µM) |
| H1993 | RESISTANCE (IC50>100 µM) | SENSITIVE (IC50~4.1 µM) |
| H2073 | SENSITIVE (IC50~0.7 µM) | — |

H1693/H1819:
H1693 CHEMO-NAIVE METASTASIZED TUMOR,
H1819 CHEMO-RESISTANT PRIMARY TUMOR

H1993/H2073:
H1993 CHEMO-NAIVE METASTASIZED TUMOR,
H2073 CHEMO-RESISTANT PRIMARY LUNG TUMOR

H1693/H1819 AND H1993/H2073 ARE ISOGENIC PAIRS (E.G. DERIVED FROM THE SAME PATIENT). BOTH CELL LINES FROM ONE PAIR ARE FROM SAME PATIENT. WE TREATED THESE CELL LINES WITH 6-THIO-DG AND FOUND THAT H1693, H1819 AND H1993 ARE INTRINSICALLY RESISTANT, H2073 IS SENSITIVE TO 6-THIO-DG. WE PRETREATED THESE RESISTANT CELL LINES WITH DEMETHYLATED AGENT 5-AZACYTIDINE AND FOUND THAT ONLY H1993 BECAME SENSITIVE TO 6-THIO-DG AFTER 5-AZACYTIDINE PRETREATMENT. THIS SUGGESTS THAT HYPERMETHYLATION OF GENES MIGHT BE THE RESISTANT MECHANISM FOR THIS SPECIFIC CELL LINE.

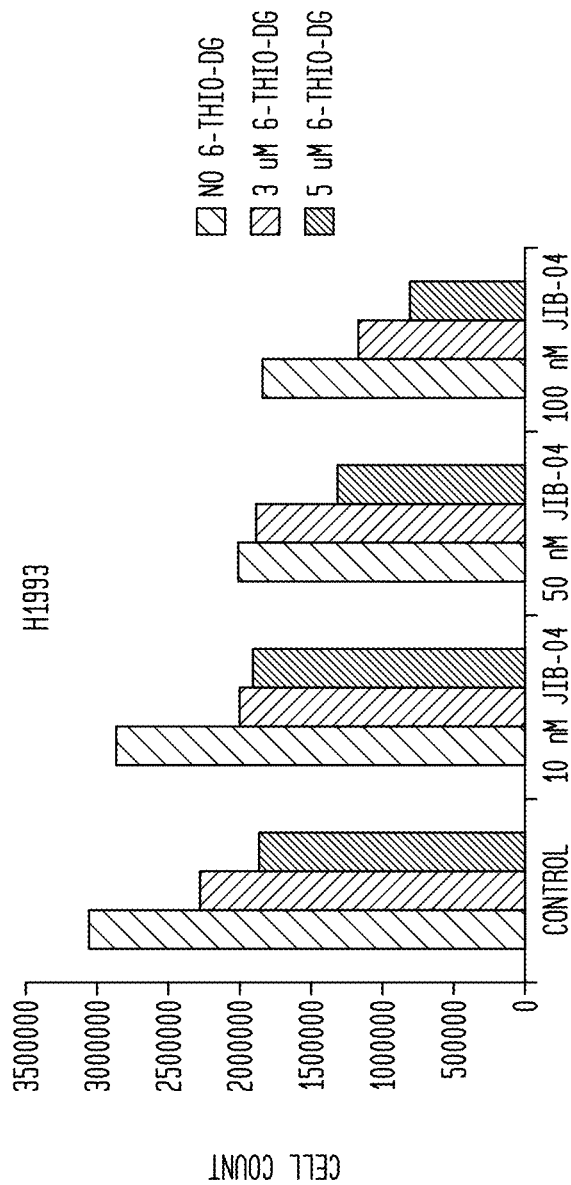

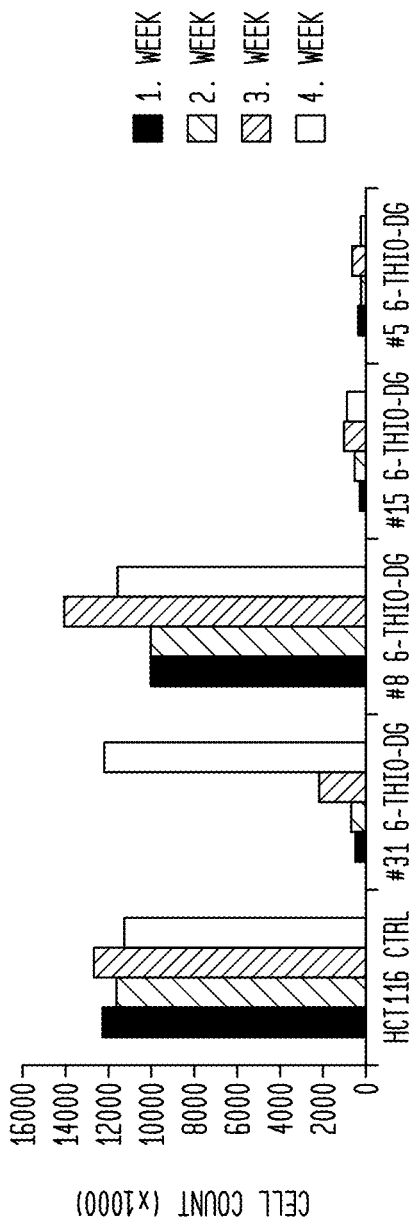

FIG. 23

HCT116 CLONES CAN ACQUIRE RESISTANCE OR INTRINSICALLY DEVELOP RESISTANCE TO 6-THIO-DG

HCT116 CLONES WERE TREATED WITH 3 μM 6-THIO-DG FOR 1-4 WEEKS (EVERY THREE DAYS)

WE SELECTED 4 CLONES AND TREATED THEM WITH 3 μM 6-THIO-DG FOR 4 WEEKS. WHILE SUBCLONE #31 IS SENSITIVE TO 6-THIO-DG FOR 3 WEEKS, IT ACQUIRED RESISTANCE FOLLOWING 4 WEEKS OF TREATMENT. INTRINSICALLY RESISTANT CLONE #8 WAS STILL RESISTANT TO THIO-6-DG FOLLOWING 4 WEEKS TREATMENT. #15 AND #5 CLONES WERE SENSITIVE DURING 4 WEEKS TREATMENT. THESE ISOGENIC CELLS THAT ARE EITHER SENSITIVE OR INTRINSICALLY/ACQUIRED RESISTANT TO 6-THIO-DG WILL BE HELPFUL TOOL TO STUDY RESISTANT MECHANISM OF 6-THIO-DG.

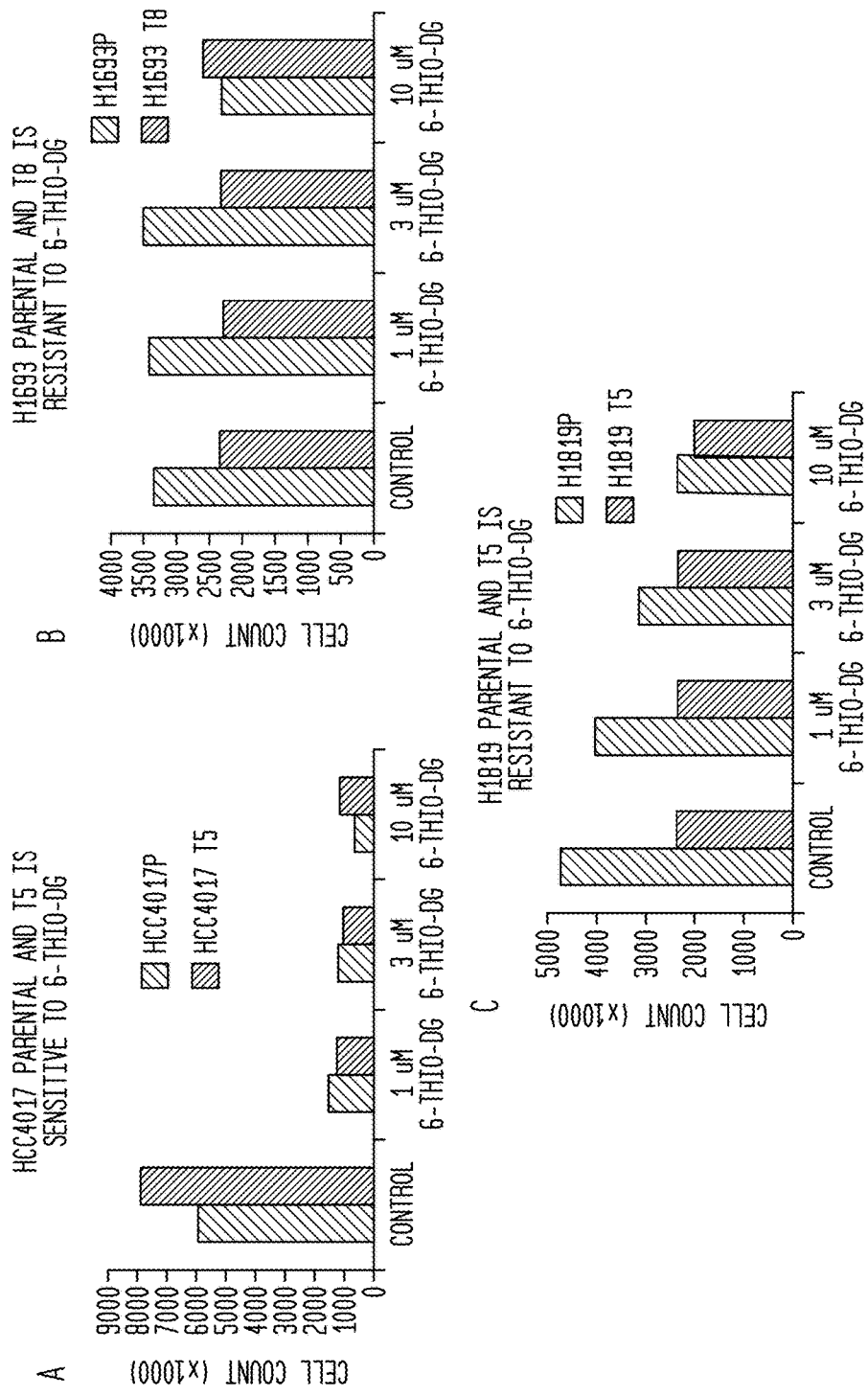

FIG. 24

CELL LINES THAT ARE SENSITIVE TO PACLITAXEL/CARBOPLATIN STANDARD CHEMOTHERAPY WERE TREATED IN VITRO FOR 5-6 CYCLES TO DEVELOP RESISTANT CELL LINES. HCC4017 (A), H1693 (B), H1819 CELL LINES (C) TREATED WITH PACLITAXEL/CARBOPLATIN DOUBLE THERAPY IN CLINICALLY RELEVANT 2:3 RATIO FOR LONG-TERM WITH INCREASING DOSES. WE TESTED THE EFFECT OF 6-THIO-DG WITH 3 DIFFERENT CONCENTRATIONS (1, 3 AND 10 $\mu$M) ON THESE PACLITAXEL/CARBOPLATIN RESISTANT CELL LINES AND FOUND THAT WHILE HCC4017 PACLITAXEL/CARBOPLATIN RESISTANT CELL LINE WAS STILL SENSITIVE TO 6-THIO-DG, H1693 AND H1819 PARENTAL AND PACLITAXEL/CARBOPLATIN RESISTANT CELL LINES WERE RESISTANT TO 6-THIO-DG, SHOWING THAT THE GENES THAT ARE RESPONSIBLE FOR ACQUISITION OF THE PACLITAXEL/CARBOPLATIN RESISTANCE ARE NOT RESPONSIBLE FOR THE ACQUISITION OF 6-THIO-DG RESISTANCE.

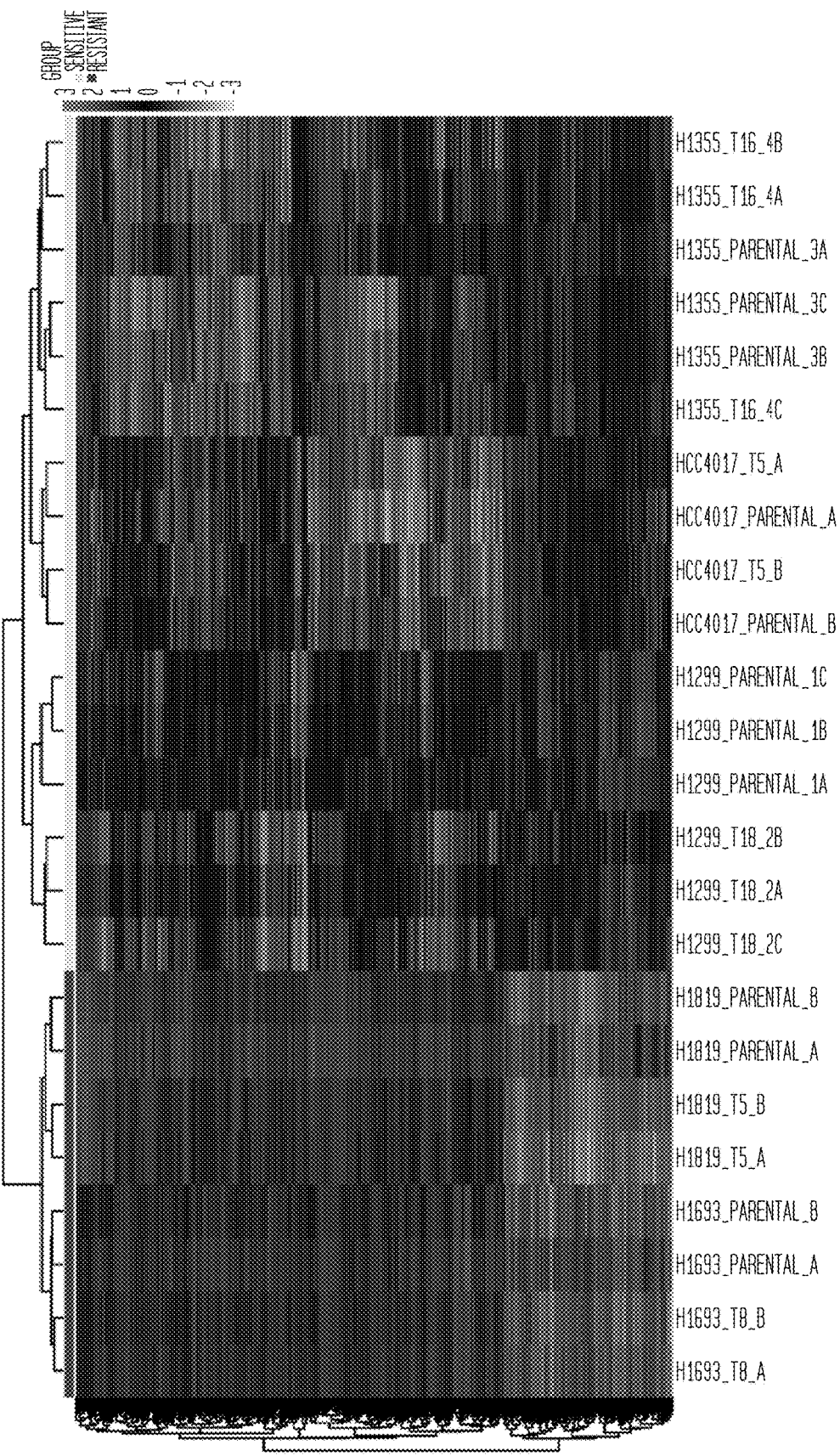

SEQUENCE LISTING

```
<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: GRN163L

<400> SEQUENCE: 1
tagggttaga caa                                                        13
```

TREATMENT OF DRUG RESISTANT PROLIFERATIVE DISEASES WITH TELOMERASE MEDIATED TELOMERE ALTERING COMPOUNDS

CROSS-REFERENCE TO RELATED APPLICATION

This application is a continuation of U.S. application Ser. No. 15/467,862, filed Mar. 23, 2017, which claims the benefit of priority to U.S. Provisional Application No. 62/312,982, filed Mar. 24, 2016, entitled "Treatment of Drug Resistant Proliferative Diseases with Telomerase Mediated Telomere Altering Compounds," the content of each of which is incorporated by reference herein in its entirety.

INCORPORATION OF SEQUENCE LISTING

The sequence listing that is contained in the file named "UTSDP3242USC1.txt", which is 1 KB (as measured in Microsoft Windows®) and was crated on Jun. 13, 2019, is filed herewith by electronic submission and is incorporated by reference herein.

FIELD OF THE INVENTION

The described invention relates generally to pharmaceutical compositions and therapeutic approaches involving compounds that have an anti-cancer effect.

BACKGROUND OF THE INVENTION

Telomeres and Telomerase

Telomeres are protective structures that are found at the end of linear eukaryotic chromosomes consisting of multiple copies of TTAGGG DNA repeats. Telomeres are associated with six proteins; telomeric repeat binding factor (TRF)1, TRF2, TIN2, Rap1, TPP1 and POT1, which all together are called the shelterin complex. (de Lange T., "Shelterin: the protein complex that shapes and safeguards human telomeres," Genes & Development 2005; 19:2100-10.) Human telomeres are protected from the cellular machinery that would normally treat the end of a linear DNA strand as being broken and needing repair. The two major telomeric binding proteins, TRF1 and TRF2 are expressed in all human cells and are associated with the telomeric repeat DNA sequences throughout the cell cycle. [Shay J W, Telomerase and cancer, Hum Mol Genet. 2001 Apr. 10(7):677-85] TRF1 and TRF2 are known to associate with hRap1 and the Mre11/Rad50/Nbs1 DNA repair complex. [Id. citing Li, B. B., et al. (2000) Identification of human Rap1: Implications for telomere evolution. Cell, 101, 471-483; Zhu, X. D., et al. (2000) Cell-cycle-regulated association of RAD50/MRE11/NBS1 with TRF2 and human telomeres. Nature Genet., 25, 347-352.] TRF2 is also known to bind to other DNA damage detection and repair factors, such as Ku70/80 heterodimer. [Id. citing Bianchi, A. and de Lange, T. (1999) Ku binds telomeric DNA in vitro. J. Biol. Chem., 274, 21223-21227; Hsu, H. L., e al. (2000) Ku acts in a unique way at the mammalian telomere to prevent end joining. Genes Dev., 14, 2807-2812.] Heterogeneous nuclear RNPs (hnRNPs), ataxia-telangiectasia mutated (ATM) kinase, and poly(ADP-ribose) polymerase (PARP) have been identified as having an effect on telomere length. [Id. citing McKay, S. J. and Cooke, H. (1992) hnRNP A2/B1 binds specifically to single stranded vertebrate telomeric repeat TTAGGGn. Nucleic Acids Res., 20, 6461-6464; LaBranche, H., et al. (1998) Telomere elongation by hnRNP A1 and a derivative that interacts with telomeric repeats and telomerase. Nature Genet., 19, 199-202; Eversole, A. and Maizels, N. (2000) In vitro properties of the conserved mammalian protein hnRNP D suggest a role in telomere maintenance. Mol. Cell. Biol., 20, 5425-5432; Dallaire, F., et al. (2000) Heterogeneous nuclear ribonucleoprotein A1 and UP1 protect mammalian telomeric repeats and modulate telomere replication in vitro. J. Biol. Chem., 275, 14509-14516; Smilenov, L. B., et al. (1997) Influence of ATM function on telomere metabolism. Oncogene, 15, 2659-2666; Smilenov, L. B., Dhar, S. and Pandita, T. K. (1999) Altered telomere nuclear matrix interactions and nucleosomal periodicity in cells derived from individuals with ataxia telangiectasia before and after ionizing radiation treatment. Mol. Cell. Biol., 19, 6963-6971; Wood, L. D., et al. (2001) Characterization of ataxia telangiectasia fibroblasts with extended life-span through telomerase expression. Oncogene, 20, 278-288; di Fagagna, F. D., et al. (1999) Functions of poly(ADP-ribose) polymerase in controlling telomere length and chromosomal stability. Nature Genet., 23, 76-80.] The far 3' end comprising the telomere terminus has a single stranded overhang that can form a higher ordered structure called the t-loop. [Id. citing Griffith, J. D., et al. (1999) Mammalian telomeres end in a large duplex loop. Cell, 97, 503-514.] These collective components and DNA structures are responsible for the protection and maintenance of the DNA ends.

Human telomerase ribonuclear protein (RNP) comprises a catalytic protein component (hTERT) and a 451 base pair RNA component, human telomerase RNA (hTR), that are both responsible for telomerase activity. [Id. citing Bodnar, A. G., et al. (1998) Extension of life-span by introduction of telomerase into normal human cells. Science, 279, 349-352; Weinrich, S. L., et al. (1997) Reconstitution of human telomerase with the catalytic protein subunit hTRT. Nature Genet., 17, 498-502.] The 3' end of the hTR is similar to the box H/ACA family of small nucleolar RNAs (snoRNAs) and is essential for 3' end processing, while the 5' end contains the template used for the addition of telomeric sequences to the chromosome ends. [Id. citing Narayanan, A., et al. (1999) Nucleolar localization signals of Box H/ACA small nucleolar RNAs. EMBO J., 18, 5120-5130; Greider, C. W. and Blackburn, E. H. (1987) The telomere terminal transferase of Tetrahymena is a ribonucleoprotein enzyme with two kinds of primer specificity. Cell, 51, 887-898.] The 5' end also contains a pseudoknot that may be important for telomerase function, as well as a 6 base pair U-rich tract necessary for interaction with hnRNPs C1 and C2. [Id. citing Gilley, D. and Blackburn, E. H. (1999) The telomerase RNA pseudoknot is critical for the stable assembly of a catalytically active ribonucleoprotein. Proc. Natl Acad. Sci. USA, 96, 6621-6625; Ford, L. P., et al. (2000) Heterogeneous nuclear ribonucleoproteins C1 and C2 associate with human telomerase. Mol. Cell. Biol., 20, 9084-9091.]

Several other proteins have been identified as associating with the human telomerase RNP. For example, the vault protein TEP1 was first identified, as well as the snoRNA binding proteins dyskerin and hGAR1, which bind to the 3' end of hTR. The chaperone proteins p23/hsp90 have also been identified as binding partners and are thought to be involved in the formation of an active telomerase assembly. [Id. citing Holt, S. E., et al. (1999) Functional requirement of p23 and Hsp90 in telomerase complexes. Genes Dev., 13, 817-826.] The La autoantigen, which is involved in the assembly of other RNA particles and maturation of tRNAs, has been shown to interact with telomerase RNP and to have expression levels that correlate with telomere length. [Id.

citing Ford, L. P., Shay, J. W. and Wright, W. E. (2001) The La antigen associates with the human telomerase ribonucleoprotein and influences telomere length in vivo. RNA, 7:1068-1075

Telomeres in all normal somatic cells undergo progressive shortening with each cell division due to an end replication problem, eventually resulting in cellular senescence. The end replication problem results from DNA replication being bidirectional, while DNA polymerase is unidirectional and must initiate replication from a primer. Therefore each round of DNA replication leaves approximately 50-200 base pairs of DNA unreplicated at the 3' end of the each DNA strand forming the chromosome. If left unchecked, the chromosome ends would become progressively shorter after each round of DNA replication. Replication-dependent telomeric shortening can be counteracted by telomerase, which adds TTAGGG repeats to the end of linear chromosomes.

Telomerase is a reverse transcriptase because of its action of copying the short RNA template sequence within the hTR into DNA. Unlike retroviral reverse transcriptases, telomerase specializes in making the short tandem repeats found at the ends of chromosomes. [Blackburn E H, Telomerase and Cancer, Molecular Cancer Research 3:477-482.] The protein component of telomerase, hTERT, includes reverse transcriptase motifs. [Id.] The core structure of the hTR component includes a pseudoknot, which is a part of the RNA that interacts strongly with the TERT protein component. [Id.]

Telomerase expression is tightly regulated in normal human cells, where it is found active in stem cells and germ cells. In other normal cell types, the levels of telomerase are typically too low to sustain telomere length through the lifetime of an average human. [Id.]

Telomeres and Cancer

While most normal somatic human cells do not have telomerase activity, it is detected, almost universally, in primary human cancer cells (~85-90%). Thus, the progressive shortening of telomeres in normal cells without telomerase activity provide an initial barrier for tumorigenesis.

Normal cells divide a limited number of times before growth and replication is arrested. The phenomenon of growth arrest is known as "cellular senescence" or "replicative senescence." By contrast, tumor cells typically have the ability to divide indefinitely; i.e. they are immortalized cells. Experimental evidence suggests that cellular aging, which ultimately results in senescence, is dependent on the number of cell divisions, and that the progressive loss of telomeric ends of chromosomes during each division is an important mechanism in the cellular aging process. [Shay J W, Telomerase and cancer, Hum Mol Genet. 2001 Apr. 10(7):677-85 citing Hayflick, L. and Moorhead, P. S. (1961) The limited in vitro lifetime of human diploid cell strains. Exp. Cell Res., 25, 585-621; Shay, J. W. and Wright, W. E. (2000) Haylick, his limit, and cellular aging. NatureRev. Mol. Cell. Biol., 1, 72-76; Greider, C. W. (1998) Telomeres and senescence: the history, the experiment, the future. Curr. Biol., 8, 178-181; Campisi, J. (1996) Replicative senescence—an old lives tale. Cell, 84, 497-500; Wright, W. E. and Shay, J. W. (1992) The two-stage mechanism controlling cellular senescence and immortalization. Exp. Gerontol., 27, 383-389; Harley, C. B. (1991) Telomere loss: mitotic clock or genetic time bomb? Mutat. Res., 256, 271-282; Harley, C. B. et al. (1990) Telomeres shorten during aging. Nature, 345, 458-460; Hastie, N. D., et al. (1990) Telomere reduction in human colorectal carcinoma and with aging. Nature, 346, 866-868; deLange, T., et al. (1990) Structure and variability of human chromosome ends. Mol. Cell. Biol., 10, 518-527; Lindsey, J., et al. (1991) In vivo loss of telomeric repeats with age in humans. Mutat. Res., 256, 45-48; Counter, C. M., et al. (1992) Telomere shortening associated with chromosome instability is arrested in immortal cells which express telomerase activity. EMBO J., 11, 1921-1929; Wright, W. E., et al. (1996) Experimental elongation of telomeres in immortal human cells extends the lifespan of immortal x normal cell hybrids. EMBO J., 15, 1734-1741; Bodnar, A. G. et al. (1998) Extension of life-span by introduction of telomerase into normal human cells. Science, 279, 349-352; Vaziri, H. and Benchimol, S. (1998) Reconstitution of telomerase activity in normal human cells leads to elongation of telomeres and extended replicative life span. Curr. Biol., 8, 279-282; Halvorsen, T. L., et al. (1999) Telomerase activity is sufficient to allow transformed cells to escape from crisis. Mol. Cell. Biol., 19, 1864-1870.] In most cases, cells enter senescence without accumulating enough mutations to become cancerous. Thus, the senescence caused by the shortening of telomeres acts as a potent anti-cancer mechanism.

Human cancers often comprise short telomeres and have high levels of telomerase. The detection of telomerase activity, including reactivation or upregulation of telomerase activity and its hTR, are associated with all cancer cell types that have been investigated.

hTERT, which is the catalytic protein of human telomerase, is thought to be critical to telomerase activity. [Id. citing Nakamura, T. M., et al. (1997) Telomerase catalytic subunit homologs from fission yeast and humans. Science, 277, 955-959.] hTERT expression is normally limited to proliferating stem-like cells and their immediate descendants in normal epithelial tissue but not in quiescent stem cells. In cancers with high telomerase activity hTERT is detected in almost all cells, while cancers with lower telomerase activity have fewer hTERT positive cells. [Id.] The level of hTERT expression in the nucleus of individual cells does not differ much between tumors having various levels of telomerase activity, indicating that relative telomerase activity from the tissue of cancer patients may be an indicator of overall tumor burden. [Id.]

While short telomeres are in the vast majority of human cancers, somewhat longer telomeres have been reported as being associated with an increased risk of brain cancer. [Walsh, K M et al. Variants near TERT and TERC influencing telomere length are associated with high-grade glioma risk, Nature Genetics 46, 731-735 (2014).] Individuals with variants of the telomere related genes TERT and TERC were, on average, found to have longer telomere length and a higher average risk factor for gliomas. [Id.]

Cancer Drug Resistance Mechanisms

Both traditional and targeted cancer therapies have varying degrees of success, in part due to drug resistant cancer cells. The drug resistance of cancer cells can be broadly classified into two types. "Intrinsic resistance" is a type of drug resistance that results from resistance mediating factors that are present in tumor tissue before treatment with an anti-cancer agent. In contrast, "acquired resistance" is the result of resistance mechanisms that develop only after treatment with an anti-cancer agent that is initially successful. Due to the heterogeneity of tumor tissues, the distinction between the two types of drug resistance is not always clear. For example, an acquired resistance may be the result of the presence of a small sub-population of cells present in the original tumor. [Xueda Hu and Zemin Zhang, Understanding the Genetic Mechanisms of Cancer Drug Resistance Using Genomic Approaches, Trends in Genetics, 2015 Dec. 12. pii: S0168-9525(15)00206-1. doi: 10.1016/j.tig.2015.11.003.

[Epub ahead of print], citing Bedard, P. L. et al. (2013) Tumour heterogeneity in the clinic. Nature 501, 355-364.]

Several biochemical and genetic mechanisms of cancer drug resistance have been implicated with respect to targeted therapies. "Targeted therapies" are drugs or other agents that interfere with specific molecules that are involved in the growth and spread of cancer. Targeted therapies differ from "standard chemotherapy" in important ways. Targeted therapies act on specific targets, while standard chemotherapy acts on all rapidly dividing cells. Targeted therapies are developed or chosen to specifically interact with a target, while standard chemotherapy agents are selected only for the ability to kill rapidly dividing cells. Targeted therapies often block tumor cell proliferation, while standard chemotherapy kill tumor cells. Exemplary mechanisms implicated in intrinsic or acquired resistance to targeted and standard anti-cancer agents include, without limitation, alteration of a drug target through secondary mutations, activation of bypass biological pathways, activation of downstream effectors that prevent cell death, epigenetic changes, alterations to drug transport and metabolism, changes to DNA mutation and repair mechanisms, and alteration to tumor cell microenvironment, and have all been implicated in drug resistance to targeted therapies. [Id.]

Alteration in Drug Targets

Alterations to a drug target can result in drug response resistance. Such changes may be the result of mutations or over-expression of a drug target protein's gene. Mutations or expression perturbations, which are examples of molecular alterations of a given target, can both result in acquired drug resistance. For example, a secondary mutation changing a glycine reside to an arginine residue at position 2032 (G2032R) in the ROS proto-oncogene 1 (ROS 1) kinase domain has been shown to result in lung adenocarcinoma resistance to crizotinib, a tyrosine kinase inhibitor of each of the anaplastic lymphoma receptor tyrosine kinase (ALK), ROS1, and the MET proto-oncogene (MET). [Awad, M. M. et al. (2013) Acquired resistance to crizotinib from a mutation in CD74-ROS1. N. Engl. J. Med. 368, 2395-2401] For example, a secondary mutation in epidermal growth factor receptor resulting in a serine residue changed to arginine at position 492 (S492R) has been found associated with colorectal cancer resistance to cetuximab by preventing proper EGFR antibody binding to its target. [Montagut, C. et al. (2012) Identification of a mutation in the extracellular domain of the epidermal growth factor receptor conferring cetuximab resistance in colorectal cancer. Nat. Med. 18, 221-223]

Altered drug target resistance has also been identified for the drug imatinib, which acts as an inhibitor of the BCR-ABL1 fusion gene responsible for chronic myeloid leukemia. A single missense mutation at T315 of BCR-ABL1 is capable of impairing imatinib binding while preserving the oncogenic functionality of the fusion protein. [Gone, M. E. et al. Clinical resistance to STI-571 cancer therapy caused by BCR-ABL gene mutation or amplification. Science 293, 876-880 (2001).]

Several examples of alterations to drug targets have been identified in lung cancer. The most common form of lung cancer is non-small cell lung cancer (NSCLC), which accounts for approximately 85% of lung cancer cases. Research into the development of targeted therapies for NSCLC has identified four members of the ErbB Family as central regulators of tumor cell proliferation, survival, migration, and metastasis. The ErbB Family comprises four members: epidermal growth factor receptor (EGFR/ErbB1), human epidermal growth factor receptor 2 (HER2/Erb2), Erb3, and Erb4. Targeting of these family members has become a primary strategy for the development of targeted therapy against NSCLC. [Christian Rolfo et al., Novel therapeutic strategies for patients with NSCLC that do not respond to treatment with EGFR inhibitors, Cancer Treatment Reviews 40 (2014) 990-1004.]

Two targeted therapies commonly used in the treatment of NSCLC are the EGFR tyrosine kinase inhibitors gefitinib and erlotinib. These two agents generally have an initial clinical benefit for certain populations of NSCLC patients, but almost invariably the cancer cell population eventually acquires resistance. There are also a number of NSCLC patient populations that do not respond to tyrosine kinase inhibitors at all. [Id.]

Intrinsic resistance of NSCLC to EGFR tyrosine kinase inhibitors can be a result of multiple genetic changes. The primary mechanism for intrinsic resistance is believed to be a mutation in EGFR of tyrosine to methionine at position 790 (T790M), which is present before tyrosine kinase inhibitor treatment. [Id. citing Fujita Y et al. Highly sensitive detection of EGFR T790M mutation using colony hybridization predicts favorable prognosis of patients with lung cancer harboring activating EGFR mutation. J Thorac Oncol 2012; 7(11):1640-4 Epub 2012 Aug. 18; Rosell R et al. Pretreatment EGFR T790M mutation and BRCA1 mRNA expression in erlotinib-treated advanced non-small-cell lung cancer patients with EGFR mutations. Clin Cancer Res 2011; 17(5):1160-8 Epub 2011 Jan. 15.] The presence of this mutation has a prognostic and predictive value for the outcome of patients when treated with EGFR tyrosine kinase inhibitors.

Other mutations to EGFR are responsible for acquired resistance to EGFR tyrosine kinase inhibitors in certain populations. For example, resistance to EGFR tyrosine kinase inhibitors can be attributed to the presence of one or more of the additional mutations D761Y, L747S, or T854A in approximately 50-80% of NSCLC patients having the T790M mutation. [Id. citing Kobayashi S, et al. EGFR mutation and resistance of non-small-cell lung cancer to gefitinib. N Engl J Med 2005; 352(8):786-92 [Epub 2005 Feb. 25]; Sharma S V, et al. A chromatin-mediated reversible drug-tolerant state in cancer cell subpopulations. Cell 2010; 141(1):69-80 [Epub 2010 Apr. 8]; Suda K, et al. EGFR T790M mutation: a double role in lung cancer cell survival? J Thorac Oncol 2009; 4(1):1-4.]

The drug target of paclitaxel, a taxane, may also be mutated, resulting in resistance. Taxanes are microtubule stabilizing agents that interfere with normal cell replication, and which have been shown to be effective against NSCLC. The taxanes bind to beta-tubulin and interferes with the dynamic equilibrium between polymerization and depolymerization of microtubules. The taxane family of drugs also includes docetaxel, and nab-paclitaxel, among others. The resistance mechanism of NSCLC cells against paclitaxel is not fully understood, but is believed to be a result of a mutation in beta-tubulin. [Monika Joshi et al., Taxanes, past, present, and future impact on non-small cell lung cancer, Anti-Cancer Drugs 25:571-583, citing Monzo M, et al., Paclitaxel resistance in non-small-cell lung cancer associated with beta-tubulin gene mutations. J Clin Oncol 1999; 17:1786-1793; Yabuki N, et al. Gene amplification and expression in lung cancer cells with acquired paclitaxel resistance. Cancer Genet Cytogenet 2007; 173:1-9.] A study of a patient population having paclitaxel resistant NSCLC found that about 33% of the patients have had a beta-tubulin mutation in exon 1 or exon 4 of the beta-tubulin gene, and that none of those patients harboring the beta-tubulin mutation showed a response to paclitaxel treatment. [Id. citing Monzo M. et al., Paclitaxel resistance in non-small cell lung cancer associated with beta-tubulin gene mutations. J. Clinical Oncology 1999; 17:1786-1793.]

Mutations to v-RAF murine sarcoma viral oncogene homolog B1 (BRAF), which is the target of several small molecule inhibitors, may result in resistance. Alternative splicing of V600E mutant BRAF has been identified as conferring drug resistance in melanoma cells. In one study, in vitro resistant cell lines were found to harbor a 61 kDa form of V600E BRAF that lacked exons 4 through 8, which coded for a RAS-binding domain critical for RAF activation. The cells expressing this splice variant were resistant to vemurafenib through a mechanism involving dimerization of the splice variant of BRAF, which strongly activates MEK and ERK in the presence of the inhibitor. [Poulikakos P I, et al. RAF inhibitor resistance is mediated by dimerization of aberrantly spliced BRAF(V600E). Nature 2011; 480(7377):387-390.]

BRAF copy number amplification, which results in BRAF overexpression, may also be responsible for conferring resistance to BRAF inhibitors by leading to ERK reactivation in a RAS or CRAF-independent manner. [Id citing Shi H, et al. Melanoma whole-exome sequencing identifies V600EB-RAF amplification-mediated acquired BRAF inhibitor resistance. Nat. Commun. 2012; 3:724.] Copy number amplification of BRAF has been identified in 8% to 20% of tumor samples after disease progression following BRAF inhibitor treatment. [Id.] BRAF amplification has also been identified in patients after treatment with both BRAF and MEK inhibitors. [Id. citing Wagle N, Van Allen E M, Treacy D J, Frederick D T, Cooper Z A, Taylor-Weiner A, Rosenberg M, Goetz E M, Sullivan R J, Farlow D N, Friedrich D C, Anderka K, Perrin D et al. MAP Kinase Pathway Alterations in BRAF-Mutant Melanoma Patients with Acquired Resistance to Combined RAF/MEK Inhibition. Cancer Discov. 2014; 4(1):61-68.]

Downstream Resistance Mechanisms

After an anti-cancer agent has accumulated inside a cell and reached its cellular target, the result of the treatment depends on how the cancer cell responds. If the anti-cancer agent is successful, the damage it causes will result in cell death. But the pathways that regulate cell death may be dysfunctional, resulting in resistance to the anti-cancer compound.

Apoptosis is the highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand (FasL) expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and-7 are downstream caspases that are activated by the upstream proteases and act themselves to cleave cellular targets.

The upregulation of the proapoptotic protein BIM (BCL2-like 11) has been found to be required for induction of apoptosis by EGFR tyrosine kinase inhibitors in EGFR-mutant NSCLC. Conversely, low BIM expression in EGFR-mutant NSCLC has been associated with resistance to EGFR tyrosine kinase inhibitors. [Faber A C, et al. BIM expression in treatment-naive cancers predicts responsiveness to kinase inhibitors. Cancer discovery. 2011; 1(4):352-65. [Epub 2011 Dec. 7]; Costa C, et al. The Impact of EGFR T790M Mutations and BIM mRNA Expression on Outcome in Patients with EGFR-Mutant NSCLC Treated with Erlotinib or Chemotherapy in the Randomized Phase III EURTAC Trial. Clin Cancer Res. 2014. Epub 2014 Feb. 5. Clin Cancer Res. 2014 Apr. 1; 20(7), pp. 2001-10.] The presence or absence of a BIM deletion polymorphism in certain populations appears to be associated with intrinsic resistance of EGFR tyrosine kinase inhibitors in EGFR-mutant NSCLC. [Ng K P, et al. A common BIM deletion polymorphism mediates intrinsic resistance and inferior responses to tyrosine kinase inhibitors in cancer. Nat Med 2012; 18(4):521-8.]

Some studies have identified cancer cells that are "addicted" to a small number of anti-apoptotic proteins, which account for survival. For example, mutations, amplifications, chromosomal translocations and over-expression of one or more of the anti-apoptotic BCL-2 family members, inhibitors of apoptosis proteins (IAPs), and the caspase 8 inhibitor FLIP may provide drug resistance due to their anti-apoptotic effects.

Autophagy is a lysosomal degradation pathway, distinct from apoptosis, that degrades organelles and proteins to maintain cellular viability during metabolic stress. Autophagy is regulated by the protein kinases mTOR and AMPK, which act as negative regulators of the Unc-51-like kinases ULK1 and ULK2. The ULK kinases activate Beclin-1, which forms the autophagy-inducable Beclin-1 complex with p150, aTg14L and the class III phosphatidylinositol 3-phosphate kinase VPS34. ULK and Beclin-1 complex re-localize to the phagophore, i.e. the site of autophagosome initiation, where they both contribute to the subsequent formation and closure of autophagosomes, which fuse with the lysosome for degradation of cargo.

Autophagy has been found to facilitate cancer cell survival during the metabolic stress cause by anti-cancer agents. [White, E. Deconvoluting the context-dependent role for autophagy in cancer. Nature Rev. Cancer 12, 401-410 (2012).] For example, treatment of cells with chloroquine, an inhibitor of autophagy, increases the regression of tumors in response to alkylating agents in a mouse model of lymphoma. Moreover, human cancer cells have been found to be sensitized to cancer therapy by hydroxychloroquine. [Amaravadi, R. K. et al. Autophagy inhibition enhances therapy-induced apoptosis in a Myc-induced model of lymphoma. J. Clin. Invest. 117, 326-336 (2007); Sasaki, K. et al. Chloroquine potentiates the anticancer effect of 5-fluorouracil on colon cancer cells. BMC Cancer 10,370 (2010).]

Resistance Promoting Responses—Bypass Biological Pathways

Oncogenic bypass and pathway redundancy are also possible mechanisms that result in drug resistant cancer cells. Oncogenic bypass occurs when a primary drug target remains unaltered and continues to be inhibited by an anti-cancer agent, but an alternative pathway becomes activated as a result of an adaptive feedback loop or genetic mutation that gets selected during anti-cancer agent treatment. For example, activation of MET, which is the gene responsible for driving ErbB3-dependent activation of PI3 kinase, is associated with resistance to EGFR inhibitors and is present in about 20% of patients with EGFR driven lung cancer.

Bypass mechanisms that result in drug resistance may be related to pathway redundancy and bypass of target agents. For example, the activation of a secondary receptor tyrosine kinase (RTK) can cause resistance to an inhibitor of a primary tyrosine kinase. [Niederst, M. J. and Engelman, J. A. (2013) Bypass mechanisms of resistance to receptor tyrosine kinase inhibition in lung cancer. Sci. Signal. 6, re6.] For example, activation of the bone morphogenetic protein (BMP)-signaling pathway in lung squamous cancers was found to result in resistance to EGFR tyrosine kinase inhibitors. [Wang, Z. et al. (2015) Activation of the BMP-BMPR pathway conferred resistance to EGFR-TKIs in lung squamous cell carcinoma patients with EGFR mutations. Proc. Natl. Acad. Sci. U.S.A. 112, 9990-9995.]

Genomic alterations that result in dysregulation of signaling proteins acting up- or down-stream of a therapeutic agent can also lead to acquired resistance. For example it has been demonstrated that, in EGFR-mutant cancer cells, a mutation resulting in oncogenic Phosphatidylinositol-4,5-bisphosphate 3-kinase catalytic subunit alpha (PIK3CA) was enough to cause resistance to the drug gefitinib, which is an EGFR inhibitor. Similar mutations in EGFR-mutant tumors have been found to cause resistance to another EGFR inhibitor, erlotinib. [Engelman, J. A. et al. (2006) Allelic dilution obscures detection of a biologically significant resistance mutation in EGFR-amplified lung cancer. J. Clin. Invest. 116, 2695-2706; Sequist, L. V. et al. (2011) Genotypic and histological evolution of lung cancers acquiring resistance to EGFR inhibitors. Sci. Transl. Med. 3, 75ra26.]

Post-transcriptional up-regulation of thymidylate synthase, a key enzyme in synthesis of 2'-deoxythymidine-5'-monophosphate, an essential precursor for DNA biosynthesis, abrogates the response to thymidylate synthase inhibitors such as 5-fluorouracil (5-FU) and permetrexed. [Holohan C., et al., Cancer drug resistance: an evolving paradigm, Nature Rev. Cancer, October 2013, vol. 13, 714-726 citing Gottesman, et al., Multidrug resistance in cancer: role of ATP-dependent transporters. Nature Rev. Cancer 2, 48-58 (2002) citing Longley, D. B., Harkin, D. P. & Johnston, P. G., 5-fluorouracil: mechanisms of action and clinical strategies. Nature Rev. Cancer 3, 330-338 (2003).] A genomically amplified androgen receptor (AR) is present in 30% of prostate cancers that have developed drug resistance to androgen deprivation therapy, such as testosterone lowering drugs and AR antagonists. [Id. citing Palmberg, C. et al. Androgen receptor gene amplification in a recurrent prostate cancer after monotherapy with the nonsteroidal potent antiandrogen Casodex (bicalutamide) with a subsequent favorable response to maximal androgen blockade. Eur. Urol. 31, 216-219 (1997).]

The expression of the Breast Cancer Type 1 susceptibility protein (BRCA1) has also been found to be a predictive marker for NSCLC patients treated with EGFR tyrosine kinase inhibitors. Patients having the T790M EGFR mutation before treatment with tyrosine kinase inhibitors and low BRCA1 levels have been found to have a longer progression free survival after treatment with erlotinib. [Id. citing Rosell R et al. Pretreatment EGFR T790M mutation and BRCA1 mRNA expression in erlotinib-treated advanced non-small-cell lung cancer patients with EGFR mutations. Clin Cancer Res 2011; 17(5):1160-8 Epub 2011/01/15.]

Other studies have identified a potentially important role for nuclear factor kappa-light-chain-enhancer (NF-kB) in NSCLC resistance to tyrosine kinase inhibitors. For example, NF-kB activation in B cells has been associated with regulating EGFR oncogene dependence in EGFR-mutant NSCLC. Furthermore, inhibition of NF-kB was found to substantially enhance the response to erlotinib treatment of EGFR-mutant NSCLC cells, both in vitro and in vivo. [Id. Bivona T G, et al. FAS and NF-kappaB signaling modulate dependence of lung cancers on mutant EGFR. Nature 2011; 471(7339):523-6 Epub 2011 Mar. 25]. Conversely, studies of EGFR-mutant NSCLC specimens also having hyperactivation of NF-kB showed a worse response to EGFR tyrosine kinase inhibitors. [Id.]

Another group of acquired drug resistance NSCLC results from amplification of mesenchymal-epithelial transition factor (MET) receptor tyrosine kinase (RTK), which activates different signaling pathways from EGFR. [Id. citing Engelman J A, et al. MET amplification leads to gefitinib resistance in lung cancer by activating ERBB3 signaling. Science 2007; 316(5827):1039-43.] MET and RTK are responsible for regulating several processes, such as cell proliferation, invasion, and angiogenesis. Various genetic alterations to MET can result in tumor formation, and stimulate the ErbB3 signaling pathway, effectively bypassing the inhibitory effects of EGFR tyrosine kinase inhibitors. MET mutations are found in about 20% of patient NSCLC cells that have acquired resistance to EGFR tyrosine kinase inhibitors. The ligand of MET, hepatocyte growth factor (HGF), may also play a role in getifitinib resistance by restoring the PI3K/Akt pathway through Gab1, but not through EGFR or ErbB3. [Id. citing Turke A B, et al. Preexistence and clonal selection of MET amplification in EGFR mutant NSCLC. Cancer Cell 2010; 17(1):77-88 [Epub 2010 Feb. 5]; Yano S, et al. Hepatocyte growth factor expression in EGFR mutant lung cancer with intrinsic and acquired resistance to tyrosine kinase inhibitors in a Japanese cohort. J Thorac Oncol 2011; 6(12):2011-7.]

The receptor tyrosine kinase AXL is a member of the TAM (Tyro3-AXL-Mer) family, and is involved in regulating tumor cell growth, proliferation, migration, adhesion and chemosensitivity. Studies have shown that EGFR-mutant NSCLC resistance to tyrosine kinase inhibitors is associated with an increase in expression of AXL and its ligand GAS6. Furthermore, inhibition of AXL, via genetic or pharmacological means, restored sensitivity to erlotinib (Tarceva®), an epidermal growth factor receptor inhibitor. [Id.]

Other receptor mutations and signaling pathways associated with EGFR tyrosine kinase inhibitor resistance include: vascular endothelial growth factor (VEGF), which has been found post-treatment with tyrosine kinase inhibitors; insulin-like growth factor 1 receptor (IGF-1R), which has been found to activate many of the same pathways as EGFR; phosphoinositide-3kinase, catalytic, alpha polypeptide (PIK3CA) mutants, which are found in about 5% of NSCLC patients having mutant EGFR who develop resistance to EGFR tyrosine kinase inhibitors; v-RAF murine sarcoma viral oncogene homolog B1 (BRAF) mutations, which have been found in about 1% of tumors with acquired tyrosine kinase resistance; HER2 amplication, which is found in 12% of lung cancers which develop resistance to EGFR tyrosine kinase inhibitors; and reduced expression of neurofibromin, which is associated with resistance to erlotinib. [Camp E R, et al., Molecular mechanisms of resistance to therapies targeting the epidermal growth factor receptor. Clin Cancer Res 2005; 11(1):397-405; Chakravarti A, Loeffler J S, Dyson N J. Insulin-like growth factor receptor I mediates resistance to anti-epidermal growth factor receptor therapy in primary human glioblastoma cells through continued activation of phosphoinositide 3-kinase signaling. Cancer Res 2002; 62(1):200-7; Ohashi K, et al., Lung cancers with acquired resistance to EGFR inhibitors occasionally harbor BRAF gene mutations but lack mutations in KRAS, NRAS, or MEK1. Proc Natl Acad Sci USA 2012; 109(31):E2127-33 [Epub 2012 Jul. 10]; Takezawa K, et al. HER2 amplification: a potential mechanism of acquired resistance to EGFR inhibition in EGFR-mutant lung cancers that lack the second-site EGFRT790M mutation. Cancer Discov 2012; 2(10):922-33; Ercan D, et al., Reactivation of ERK signaling causes resistance to EGFR kinase inhibitors. Cancer Discov 2012; 2(10):934-47; De Bruin E C, et al. Reduced NF1 expression confers resistance to EGFR inhibition in lung cancer. Cancer Discov. 2014; 4(5): 606-19. doi: 10.1158/2159-8290. CD-13-0741].

Another bypass mechanism of BRAF inhibitors may rely on the presence of activating MEK1 and MEK2 mutations, which have been identified in a small number of melanoma cases. [Wagle N, et al. Dissecting Therapeutic Resistance to RAF Inhibition in Melanoma by Tumor Genomic Profiling. J. Clin. Oncol. 2011, 29(22):3085-3096; Shi H, et al. Preexisting MEK1 Exon 3 Mutations in V600E/BRAF Melanomas Do Not Confer Resistance to BRAF Inhibitors. Cancer Discov. 2012; 2(5):414-424; Emery C M, et al. MEK1 mutations confer resistance to MEK and B-RAF inhibition. Proc. Natl. Acad. Sci. 2009; 106(48):20411-20416.] Many different mutations in MEK1 and MEK2 have been identified, but only some are able to confer BRAF inhibitor resistance. [Id.]

In some cases an early adaptive response to BRAF inhibitors may select for a sub-population of resistant melanoma cells, which then undergo further changes that lead to a secondary acquired resistance. For example, in BRAF mutated cells BRAF largely exists as an active monomer and ERK-dependent feedback suppresses RAS activation, causing a decreased sensitivity to growth factors and transduction signals from receptor tyrosine kinases. Exposure of such cells to BRAF inhibitors relieves the ERK negative feedback, which results in an enhanced ability for growth factors, and other ligands, to activate signaling and an increased level of activated RAS. Thus, the relief of ERK negative feedback via BRAF-inhibitors has the perverse effect of restoring sensitivity to growth factors. Studies have shown, however, that RAS activation levels vary between cell lines and in most cases is not sufficient to cause resistance alone, but can cooperate with other resistance mechanisms requiring active receptor tyrosine kinases. [Lito P, Rosen N, Solit D B. Tumor adaptation and resistance to RAF inhibitors. Nat. Med. 2013; 19(11):1401-1409.]

Upregulated forkhead box D3 (FOXD3) can lead to BRAF inhibitor resistance in some examples of melanoma. The FOXD3 protein is a stem cell/pluripotency transcription factor found to be upregulated during MAPK inhibition, which primes cells for resistance to cell death. [Id. citing Abel E V, Aplin A E. FOXD3 Is a Mutant B-RAF-Regulated Inhibitor of G1-S Progression in Melanoma Cells. Cancer Res. 2010; 70(7):2891-2900.] Some studies have shown that combined treatment of BRAF inhibitors with integrin inhibitors may overcome this form of resistance, because the integrin inhibitors block signals from the extracellular matrix, thus preventing upregulation of FOXD3. [Basile K J, Abel E V, Aplin A E. Adaptive upregulation of FOXD3 and resistance to PLX4032/4720-induced cell death in mutant B-RAF melanoma cells. Oncogene 2011; 31(19): 2471-2479.]

Pro-survival signaling pathways may also be involved in bypass mechanisms of anti-cancer agent resistance. Pro-survival signaling refers to the collective cell signaling pathways responsible for active inhibition of apoptosis accomplished by inhibiting expression of pro-apoptotic factors and promoting expression of anti-apoptotic factors. For example, the PI3K pathway, which is activated by many pro-survival signaling pathways, leads to activation of Akt, which is an important player in survival signaling.

Pro-survival transcription factors, such as nuclear factor-kappa B (NF-κB) and signal transducer and activator of transcription 3 (STAT3), may be activated by oncogenic mutations resulting in the activation of upstream pro-survival signaling pathways. [Letai, A. G. Diagnosing and exploiting cancer's addiction to blocks in apoptosis. Nature Rev. Cancer 8, 121-132 (2008).] In leukemic cells and mouse thymocytes, over-expression of the anti-apoptotic factor BCL-2 causes resistance to various cytotoxic chemotherapeutic agents, suggesting a common pathway of cell death despite diverse mechanisms of action of each cytotoxic drug. [Sentman, C. L., et al., Bcl-2 inhibits multiple forms of apoptosis but not negative selection in thymocytes. Cell 67, 879-888 (1991); Miyashita, T. & Reed, J. C. bcl-2 gene transfer increases relative resistance of S49.1 and WEHI7.2 lymphoid cells to cell death and DNA fragmentation induced by glucocorticoids and multiple chemotherapeutic drugs. Cancer Res. 52, 5407-5411 (1992).] The interplay between anti-apoptotic BCL-2 family members (such as BCL-X and MCL1), and pro-apoptotic family members (such as BAX, BAD and BAK) controls cell death by ultimately inhibiting or facilitating induction of mitochondrial outer membrane permeablization (MOMP), which is considered the point of no return for apoptotic cell death. As such, BCL-2 family members play a pivotal role in cell death, and mutations in those family members can result in anti-apoptotic resistance to anti-cancer agents. [Wang, G. Q. et al., A role for mitochondrial Bak in apoptotic response to anticancer drugs. J. Biol. Chem. 276, 34307-34317 (2001); Chipuk, J. E., Moldoveanu, T., Llambi, F., Parsons, M. J. & Green, D. R. The BCL-2 family reunion. Mol. Cell 37, 299-310 (2010).]

Activation of epidermal growth factor receptor (EGFR) has been reported as a resistance mechanism to various chemotherapy agents. [Kishida, O. et al. Gefitinib ("Iressa", ZD1839) inhibits SN38-triggered EGF signals and IL-8 production in gastric cancer cells. Cancer Chemother. Pharmacol. 55, 393-403 (2005); Sumitomo, M., et al., ZD1839 modulates paclitaxel response in renal cancer by blocking paclitaxel-induced activation of the epidermal growth factor receptor extracellular signal-regulated kinase pathway. Clin. Cancer Res. 10, 794-801 (2004); Van Schaeybroeck, S. et al. Epidermal growth factor receptor activity determines response of colorectal cancer cells to gefitinib alone and in combination with chemotherapy. Clin. Cancer Res. 11, 7480-7489 (2005); Van Schaeybroeck, S. et al. Src and ADAM-17 mediated shedding of transforming growth factor-α is a mechanism of acute resistance to TRAIL. Cancer Res. 68, 8312-8321 (2008).] As such, EGFR-target therapies have been identified as sensitizers of various tumors for agents such as 5-FU, irinotecan, paclitaxel, and TRAIL, both in vivo and in vitro. [Id.] Zinc-dependent, membrane-associated metalloproteinases, ADAM (a disintegrin and metalloproteinase) can cleave and thereby activate ligands which in turn activate growth factor receptor tyrosine kinases (RTKs). One ADAM member, ADAM 17, has been shown to activate an adaptive resistance mechanism through chemotherapy induced activation of EGFR. Furthermore, inhibition of ADAM 17 combined with chemotherapy results in synergistic inhibition of tumor growth in several cancer models. [Id. citing Sunnarborg, S. W. et al. Tumor necrosis factor-α converting enzyme (TACE) regulates epidermal growth factor receptor ligand availability. J. Biol. Chem. 277, 12838-12845 (2002); Lee, D. C. et al. TACE/ADAM17 processing of EGFR ligands indicates a role as a physiological convertase. Ann. NY Acad. Sci. 995, 22-38 (2003); Kyula, J. N. et al. Chemotherapy-induced activation of ADAM-17: a novel mechanism of drug resistance in colorectal cancer. Clin. Cancer Res. 16, 3378-3389 (2010); Zhou, B. B. et al. Targeting ADAM-mediated ligand cleavage to inhibit HER3 and EGFR pathways in non-small cell lung cancer. Cancer Cell 10, 39-50 (2006).]

Bypass mechanisms of resistance have been described in melanoma cells. Approximately half of metastatic melanoma patients harbor a mutation in B-Raf proto-oncogene (BRAF), which is one causative agent of the disease, and BRAF inhibitors, such as vemurafenib and dabrafenib, have had some success in treating melanoma in some patients. [Spagnolo, F. et al., Overcoming resistance to BRAF inhibition in BRAF-mutated metastatic melanoma, Oncotarget, Vol. 5, No. 21 10206-10221, citing McArthur G A, et al. Safety and efficacy of vemurafenib in BRAFV600E and BRAFV600K mutation-positive melanoma (BRIM-3): extended follow-up of a phase 3, randomised, open-label study. Lancet Oncol. 2014; 15(3):323-332.] Unfortunately, the majority of melanomas treated with BRAF inhibitors acquire resistance to the treatment. Furthermore, about 15% of melanomas treated with BRAF inhibitors have intrinsic resistance, and do not achieve tumor regression at all. [Hauschild A et al., Dabrafenib in BRAF-mutated metastatic melanoma: a multicentre, open-label, phase 3 randomised controlled trial. The Lancet 2012; 380(9839):358-365.]

Several possible bypass mechanisms of intrinsic resistance to BRAF inhibitors in melanoma have been identified. For example, P29S mutations in RAC1, which is a RAS-related GTPase that regulates cell proliferation and migration, is a recurrent mutation associated with drug resistance and is present in about 9.2% of non-acral melanomas. [Krauthammer M, et al. Exome sequencing identifies recurrent somatic RAC1 mutations in melanoma. Nat. Genet. 2012; 44(9):1006-1014.] One study found that the P29S RAC1 mutation was present in three members of a cohort of 14 patients exhibiting intrinsic resistance, and in no patient harboring the mutations that responded to BRAF inhibitor therapy. [Van Allen E M et al., The Genetic Landscape of Clinical Resistance to RAF Inhibition in Metastatic Melanoma. Cancer Discov. 2014; 4(1):94-109.]

Loss of PTEN, which functions as a tumor suppressor by inhibiting PI3K signaling, is found in 10% to 33% of melanoma specimens. The loss of PTEN may play a role in intrinsic drug resistance to BRAF inhibitors by increasing PI3K/AKT signaling when BRAF is inhibited. Loss of PTEN may also result in the suppression of apoptosis via protein BIM, which is a member of the Bcl-2 protein family. [Paraiso KHT, et al. PTEN Loss Confers BRAF Inhibitor Resistance to Melanoma Cells through the Suppression of BIM Expression. Cancer Res. 2011; 71(7):2750-2760; Xing F, et al., Concurrent loss of the PTEN and RB1 tumor suppressors attenuates RAF dependence in melanomas harboring V600EBRAF. Oncogene 2012; 31(4):446-457; Nathanson K L, et al., Tumor Genetic Analyses of Patients with Metastatic Melanoma Treated with the BRAF Inhibitor Dabrafenib (GSK2118436). Clin. Cancer Res. 2013; 19(17): 4868-4878.] It is believed that PTEN loss alone is not sufficient to confer drug resistance in melanoma cells, but rather only when it occurs with other mutations. Nevertheless, it has been observed in a clinical setting that melanoma patients having wild type PTEN are more sensitive to the BRAF inhibitor dabrafenib and have longer progression free survival than patients with at least one functionally inactive allele of PTEN. [Nathanson K L et al. Tumor Genetic Analyses of Patients with Metastatic Melanoma Treated with the BRAF Inhibitor Dabrafenib (GSK2118436). Clin. Cancer Res. 2013; 19(17):4868-4878.]

Intrinsic resistance to BRAF inhibitors may also be conferred to melanoma cells via dysregulation of cyclin-dependent kinase 4 (CDK4) and/or cyclin D1. Cyclin D1 is a known regulator of proliferation, binding to both CDK4 and CDK6, resulting in phosphorylation of retinoblastoma protein and leading to progression through the cell cycle. Some studies have found that while CDK4 mutations alone did not alter responsiveness to BRAF inhibitors, cyclin D1 overexpression alone increased resistance to BRAF inhibitors. [Smalley K S, et al., Increased cyclin D1 expression can mediate BRAF inhibitor resistance in BRAF V600E—mutated melanomas. Mol. Cancer Ther. 2008; 7(9):2876-2883.] Furthermore, studies have shown that cells harboring both a mutation to CDK4 and a cyclin D1 amplification were most resistant to BRAF inhibitors in BRAF mutant melanomas. [Id.]

Melanoma cells may also be endowed with intrinsic resistance to BRAF inhibitors through the loss of NFL NF1 is a known tumor suppressor that is involved in the signaling pathways downstream of RAS, including PI3K/AKT and MAPK. Functional inactivation of NF1 results in activation of these pathways. Studies have shown that inactivating mutations in NF1 are exhibited in about 4% of BRAF-mutant melanomas. Such a NF1 mutant may both cooperate with BRAF mutations to drive melanoma progression and play a role in intrinsic and acquired resistance to BRAF inhibitors. [Mar V J, et al. BRAF/NRAS Wild-Type Melanomas Have a High Mutation Load Correlating with Histologic and Molecular Signatures of UV Damage. Clin. Cancer Res. 2013; 19(17):4589-4598; Gibney G T, Smalley K S M. An Unholy Alliance: Cooperation between BRAF and NF1 in Melanoma Development and BRAF Inhibitor Resistance. Cancer Discov. 2013; 3(3):260-263; Whittaker S R, et al. A Genome-Scale RNA Interference Screen Implicates NF1 Loss in Resistance to RAF Inhibition. Cancer Discov. 2013; 3(3):350-362; Maertens O, et al. Elucidating Distinct Roles for NF1 in Melanomagenesis. Cancer Discov. 2013; 3(3):338-349; Nissan M H, et al., Loss of NF1 in Cutaneous Melanoma Is Associated with RAS Activation and MEK Dependence. Cancer Res. 2014; 74(8):2340-2350.]

In addition to intrinsic resistance via bypass mechanisms, melanoma cells may acquire BRAF inhibitor resistance during treatment. This resistance may occur from a single acquired mechanism, or through multiple mechanisms acquired simultaneously. [Gowrishankar K, et al. Acquired resistance to BRAF inhibition can confer cross-resistance to combined BRAF/MEK inhibition. J. Invest. Dermatol. 2012; 132(7):1850-1859.] The drug vemurafenib, which is an inhibitor of the most common form of mutated BRAF (V600E), displays initial anti-cancer activity, but invariably resistance develops, which is believed to be the result of numerous resistance mechanisms, including acute adaptive response (such as the activation of alternative RAF isoforms) and selection of tumor cells that have acquired mutations in KRAS, NRAS, and MEK1 genes.

Some studies have identified the upregulation and activation of some receptor tyrosine kinases (RTKs) as conferring BRAF inhibitor resistance. Upregulation and activation of platelet derived growth factor receptor b (PDGFRb) has been identified as an acquired mechanism of BRAF inhibitor resistance, and has been associated with resistance to the inhibitor imatinib. [Id. citing Poulikakos P I, Rosen N. Mutant BRAF Melanomas—Dependence and Resistance. Cancer Cell 2011; 19(1):11-15.] In another study, melanoma cells derived from six progressing tumor samples acquired EGFR expression, which is not generally expressed by melanoma cells. [Id.] While studies have shown that EGFR expression in melanoma cells is disadvantageous for BRAF V600E mutant melanomas in the absence of BRAF inhibitors, the expression of EGFR provides a survival benefit in the presence of BRAF inhibitors. [Id. citing Sun C, et al. Reversible and adaptive resistance to BRAF(V600E) inhibition in melanoma. Nature 2014; 508(7494):118-122; Girotti M R, et al., Inhibiting EGF Receptor or SRC Family Kinase Signaling Overcomes BRAF Inhibitor Resistance in Melanoma. Cancer Discov. 2013; 3(2):158-167.]

Activating mutations have been implicated in bypass mechanisms of resistance. An activating mutation is a mutation to a gene coding for a protein that confers constitutive activity. For example, an activating mutation to a receptor tyrosine kinase would result in activation of the receptor and constitutive kinase activity independent of the receptor's ligand. Some studies have identified an activating mutation to NRAS as conferring BRAF inhibitor resistance in BRAF mutant melanoma. One study identified NRAS mutations in 4 out of 19 tumor samples with acquired resistance to the drug vemurafenib, suggesting a role for NRAS in a clinical setting. [Poulikakos P I, et al. RAF inhibitor resistance is mediated by dimerization of aberrantly spliced BRAF (V600E). Nature 2011; 480(7377):387-390.]

Epithelial-Mesenchymal Transition (EMT)

Epithelial cells are capable of transitioning to a mesenchymal phenotype, whereby the epithelial cells lose polarized organization and tight cell-cell junctions and change cell shape to a fibroblast morphology associated with increased motility and invasiveness. This change in cell phenotype can result from changes to a variety of transcription factors that regulate expression of proteins responsible for cell polarity, cell-cell contacts, cytoskeletal structure, and extra-cellular matrix degradation. These phenotypic changes may also be associated with resistance to various anti-cancer agents. [Sequist L V, et al. Genotypic and histological evolution of lung cancers acquiring resistance to EGFR inhibitors. Sci Transl Med. 2011; 3(75):75ra26.]

For example, the activation of AXL receptor tyrosine kinase (AXL) and the resulting epithelial-mesenchymal transition of non-small cell lung carcinoma cells cause resistance to EGFR-targeting therapies. [Zhang, Z. et al. (2012) Activation of the AXL kinase causes resistance to EGFR-targeted therapy in lung cancer. Nat. Genet. 44, 852-860.] The AXL receptor tyrosine kinase is not required for continued intrinsic resistance. [Konieczkowski, D. J. et al. (2014) A melanoma cell state distinction influences sensitivity to MAPK pathway inhibitors. Cancer Discov. 4, 816-827.]

In another example, NSCLC drug resistance resulted from the process of epithelial-mesenchymal transformation (EMT). [Sequist L V, et al. Genotypic and histological evolution of lung cancers acquiring resistance to EGFR inhibitors. Sci Transl Med. 2011; 3(75):75ra26.] Studies have shown that cells containing wild-type EGFR, which retained certain epithelial cell features (such as E-cadherin expression) were more sensitive to erlotinib. Conversely, those cells expressing mesenchymal markers such as vimentin and/or fibronectin were erlotinib resistant. [Id. citing Thomson S et al. Epithelial to mesenchymal transition is a determinant of sensitivity of non-small-cell lung carcinoma cell lines and xenografts to epidermal growth factor receptor inhibition. Cancer Res 2005; 65(20):9455-62] The EMT phenotype of NSCLC may result from a loss of MED12, which negatively regulates transforming growth factor [TGF]-betaR2. Studies have shown that TGF-beta receptor inhibition is capable of restoring drug responsiveness in NSCLC cells displaying loss of MED12. [Id. citing Huang S, et al. MED12 controls the response to multiple cancer drugs through regulation of TGF-beta receptor signaling. Cell 2012; 151(5):937-50.]

Some studies have identified the phenotypic changes to NSCLC associated with resistance to tyrosine kinase inhibitors (TKIs) in about 14% of the NSCLC patients studied. One phenotypic change identified was from an NSCLC phenotype originally present to a small cell lung cancer (SCLC) phenotype at the time of resistance. [Sequist L V et al., Genotypic and histological evolution of lung cancers acquiring resistance to EGFR inhibitors. Sci Transl Med. 2011; 3(75):75ra26.] The study revealed that the phenotype transition from NSCLC to SCLC was specific to tyrosine kinase inhibitor resistant cells. [Id.]

Another type of phenotypic change found in NSCLC that can result in drug resistance is a high-level amplification at cytoband 22q11.21, which contains the crk-lke (CRKL) gene responsible for cell proliferation, and is present in multiple NSCLC cell lines and 3% of lung cancer specimens. [Cheung H W, et al., Amplification of CRKL induces transformation and epidermal growth factor receptor inhibitor resistance in human non-small cell lung cancers. Cancer Discov. 2011; 1(7):608-25.] This amplification results in overexpression of CRKL and promotes anchorage independent growth and tumorigenicity through activation of the SOS1-RAS-RAF-ERK signaling pathway and the SRC-C3G-RAP1 signaling pathway. CRKL overexpression has been associated with resistance to gefitinib in EGFR mutant cells. [Cheung H W et al., Amplification of CRKL induces transformation and epidermal growth factor receptor inhibitor resistance in human non-small cell lung cancers. Cancer Discov 2011; 1(7):608-25; Kim Y H, et al., Genomic and functional analysis identifies CRKL as an oncogene amplified in lung cancer. Oncogene 2010; 29(10):1421-30.]

Tumor Microenvironment

A tumor's microenvironment may also play a role in resistance to chemotherapy and targeted drugs. Different types of cancer live and evolve in different microenvironments. For example, while the microenvironment of solid tumors comprises extracellular matrix, cancer associated fibroblasts, immune/inflammatory cells, and blood vessels, hematological malignancies live in a microenvironment comprising bone marrow stromal cells, bone marrow endothelial cells, osteoclasts, osteoblasts, macrophages, and T cells. These differences present different challenges for cancer treatment. For example, expression of integrins, which are the cell surface adhesion molecules that bind to the extracellular matrix, can be overexpressed in tumors cells, and is associated with drug resistance and increased cancer cell survival. Studies have shown that integrin mediated signaling can effect drug sensitivity by altering apoptotic mechanisms and causing changes to drug targets. [Ruoslahti, E. & Pierschbacher, M. D. New perspectives in cell adhesion: RGD and integrins. Science 238, 491-497 (1987); Hoyt, K. et al. Tissue elasticity properties as biomarkers for prostate cancer. Cancer Biomark 4, 213-225 (2008); Damiano, J. S. Integrins as novel drug targets for overcoming innate drug resistance. Curr. Cancer Drug Targets 2, 37-43 (2002).] For example, integrins are capable of modulating cell signaling pathways including PI3kinase-AKT, ERK, and NF-κB, which promote cell survival and drug resistance. Such drug resistance mechanisms have been identified in ErbB2-positive metastatic breast cancer cells, where β1-integrin expression level could be used to predict cancer cell response to trastuzamab, which is an ErbB2 targeting antibody. [Danen, E. H. Integrins: regulators of tissue function and cancer progression. Curr. Pharm. Des. 11, 881-891 (2005); Lesniak, D. et al. β1-integrin circumvents the antiproliferative effects of trastuzumab in human epidermal growth factor receptor-2-positive breast cancer. Cancer Res. 69, 8620-8628 (2009).]

Innate resistance to RAF inhibitors has been shown to be caused by hepatocyte growth factor (HGF) secretion in the tumor microenvironment. [Straussman, R. et al. (2012) Tumour micro environment elicits innate resistance to RAF inhibitors through HGF secretion. Nature 487, 500-504.] B-Raf proto-oncogene (BRAF), a component of the tumor microenvironment, may be inhibited and result in activation of melanoma-associated fibroblasts, which results in drug resistance via focal adhesion kinase (FAK)-dependent melanoma survival signaling. [Hirata, E. et al. (2015) Intravital imaging reveals how BRAF inhibition generates drug-tolerant microenvironments with high integrin beta 1/FAK signaling. Cancer Cell 27, 574-588.]

Cytokines and growth factors present in the microenvironment may also be responsible for resistance to anticancer agents. In one study, both interleukin 6 (IL-6) and tissue inhibitor of metalloproteinases (TIMP1) were released into the thymus of a mouse model of Burkitt's lymphoma in response to treatment with doxorubicin, which resulted in establishment of a chemoresistant niche which could lead to survival of residual lymphoma cells. [Gilbert, L. A. & Hemann, M. T. DNA damage-mediated induction of a chemoresistant niche. Cell 143, 355-366 (2010).] In another study, a cell line panel derived from multiple cancer types was used to assess the differential effects of various growth factors on sensitivity to kinase inhibitors. The results of the study revealed that each of hepatocyte growth factor (HGF), fibroblast growth factor (FGF) and neuregulin (NRG1) caused drug resistance by reactivating one or more of the PI3K-AKT or MEK-ERK pathways. [Wilson, T. R. et al. Widespread potential for growth factor-driven resistance to anticancer kinase inhibitors. Nature 487, 505-509 (2012).] This type of ligand mediated resistance to therapies has been identified in ErbB2 amplified breast cancer cell lines, and melanoma models. [Id.] Furthermore, the presence of hepatocyte growth factor (HGF) circulating in patients with BRAF mutant (V600E) melanoma has been associated with a decrease in overall survival for patients treated with vemurafenib. [Id.] Another study investigated the effects of stromal cells on the sensitivity of human cancer cell lines to a panel of anticancer drugs. The stromal cell lines were derived from human bone marrow, cancer-associated fibroblasts, mammary fibroblasts, skin, and umbilical cord epithelium. The stromal cells were co-cultured with breast cancer, non-small cell lung cancer, colorectal cancer, pancreatic cancer, head and neck squamous cell carcinoma, gastrointestinal stromal tumor, and melanoma cell lines. The study revealed that the BRAF (V600E) mutant melanoma cells co-cultured with fibroblasts and treated with BRAF inhibitor PLX4720 had a higher resistance to the therapy due to the presence of HGF in the co-culture medium; this cell line could be re-sensitized to the BRAF inhibitor by inhibiting HGF or its receptor, MET. [Straussman, R. et al. Tumour micro-environment elicits innate resistance to RAF inhibitors through HGF secretion. Nature 487, 500-504 (2012).]

A possible mechanism of intrinsic BRAF inhibitor drug resistance in melanoma involves alterations in RTK signaling, resulting in stromal secretion of hepatocyte growth factor (HGF). Studies have found that adding HGF to BRAF mutant melanoma cell lines results in resistance to BRAF inhibitors. [Wilson T R, et al. Widespread potential for growth-factor-driven resistance to anticancer kinase inhibitors. Nature 2012; 487(7408):505-509.] The mechanism of resistance has been shown in some studies to be mediated by activation of HGF receptor c-MET, which results in activation of MAPK and PI3K-AKT signaling pathways. This mechanism of BRAF inhibitor resistance is sensitive to c-MET and HGF inhibition. [Straussman R, et al. Tumour micro-environment elicits innate resistance to RAF inhibitors through HGF secretion. Nature 2012; 487(7408):500-504.] Studies have also found that melanoma patients with high baseline HGF level have reduced response rates to BRAF inhibitors. [Id.]

Epigenetic Changes

Epigenetic modifications have also been implicated in resistance to targeted therapies and chemotherapies, in part, because epigenetic changes can result in diverse gene expression patterns in tumors. For example, a fraction of otherwise sensitive lung cancer cell line PC9 treated with an EGFR inhibitor can become resistant by entering a reversible epigenetic state. This resistant epigenetic state may be reversed by treatment with a histone deacetylase inhibitor. [Sharma, S. V. et al. (2010) A chromatin-mediated reversible drug tolerant state in cancer cell subpopulations. Cell 141, 69-80.] Furthermore, potential DNA methylation drivers of cisplatin resistance in several types of cancer have been identified by DNA methylation and RNA expression profiling. [Zeller, C. et al. (2012) Candidate DNA methylation drivers of acquired cisplatin resistance in ovarian cancer identified by methylome and expression profiling. Oncogene 31, 4567-4576; Zhang, Y. W. et al. (2014) Integrated analysis of DNA methylation and mRNA expression profiling reveals candidate genes associated with cisplatin resistance in non-small cell lung cancer. Epigenetics 9, 896-909.] Several clinical trials of epigenetic therapeutic agents on solid tumors are being pursued because epigenetic modulators have been found to achieve re-sensitization of tumors to chemotherapy agents. [Garrido-Laguna, I. et al. (2013) A phaseI/II study of decitabine in combination with panitumumab in patients with wild-type (wt) KRAS metastatic colorectal cancer. Inves. NewDrugs 31, 1257-1264; Bauer, S. et al. (2014) Phase I study of panobinostatandimatinibin patients with treatment-refractory metastatic gastrointestinal stromal tumors. Br. J. Cancer 110, 1155-1162; Falchook, G. S. et al. (2013) Methylation and histone deacetylase inhibition in combination with platinum treatment in patients with advanced malignancies. Inves. NewDrugs 31, 1192-1200; Glasspool, R. M. et al. (2014) A randomised, phase II trial of the DNA-hypomethylating agent 5-aza-20-deoxycytidine (decitabine) in combination with carboplatin vs carboplatin alone in patients with recurrent, partially platinum-sensitive ovarian cancer. Br. J. Cancer 110, 1923-1929.]

Drug Transport and Metabolism

Drug transport and metabolism is also involved in drug resistance in cancer cells. For example, resistance to several commonly used chemotherapy agents has been associated with cell membrane transporter proteins (for example, the ATP-binding cassette (ABC) transporter family of membrane proteins, which are known to regulate the flux of mechanistically unrelated chemotherapy agents across the cell membrane. [Holohan C., et al., Cancer drug resistance: an evolving paradigm, Nature Rev. Cancer, October 2013, vol. 13 714-726 citing Gottesman, et al., Multidrug resistance in cancer: role of ATP-dependent transporters. Nature Rev. Cancer 2, 48-58 (2002)] that promote drug efflux. The presence of these ABC transporters has been shown to confer drug resistance via physical removal of anti-cancer agents from the cell. [Dean, M. (2009). ABC transporters, drug resistance, and cancer stem cells. Journal of Mammary Gland Biology and Neoplasia 14(1), 3-9.] Elevated levels of ABC transporters ABCA2, MDR1, and MRP1 were identified in the lung cancer cell lines H460, H23, HTB-58, A549, H441, and H2170. All cell lines had increased resistance to cisplatin, gemcitabine, and vinorelbine, which are common first-line lung cancer therapies. Also, high telomerase activity was identified in those cell lines. [Blasco, M. A. (2005). Telomeres and human disease: Ageing, cancer and beyond. Nature Reviews Genetics 6(8), 611-622; Ho, M. M., Ng, A. V., Lam, S., & Hung, J. Y. (2007). Side population in human lung cancer cell lines and tumors is enriched with stem-like cancer cells. Cancer Research 67(10), 4827-4833.]

Each of the ABC family members multi-drug resistance protein 1 (MDR1), multi-drug resistance-associated protein 1 (MRP1) and breast cancer resistance protein (BCRP) has been associated with drug resistant cancer cells. Each family member has been found to share substrate specificity and promote elimination of hydrophobic compounds that include common chemotherapy agent such as taxanes, topoisomerase inhibitors and antimetabolites. MDR1 has been found to be overexpressed in many tumors before treatment, (providing intrinsic drug resistance) and has also been found to be overexpressed in response to chemotherapy (providing acquired resistance). [Thomas, H. & Coley, H. M. Overcoming multidrug resistance in cancer: an update on the clinical strategy of inhibiting P-glycoprotein. Cancer Control 10, 159-165 (2003).] MDR1 over-expression has been associated with many types of drug resistant cancers, including kidney, colon, liver, prostate, lung, and breast cancers, as well as leukemias and lymphomas. [Triller, N., et al., Multidrug resistance in small cell lung cancer: expression of P-glycoprotein, multidrug resistance protein 1 and lung resistance protein in chemo-naive patients and in relapsed disease. Lung Cancer 54, 235-240 (2006); Nooter, K. et al. The prognostic significance of expression of the multidrug resistance-associated protein (MRP) in primary breast cancer. Br. J. Cancer 76, 486-493 (1997); Zalcberg, J. et al. MRP1 not MDR1 gene expression is the predominant mechanism of acquired multidrug resistance in two prostate carcinoma cell lines. Prostate Cancer Prostatic Dis. 3, 66-75 (2000).] BCRP protein has been found to be associated with chemoresistance in breast cancer and leukemia. [Doyle, L. A. et al. A multidrug resistance transporter from human MCF-7 breast cancer cells. Proc. Natl Acad. Sci. USA 95, 15665-15670 (1998); Robey, R. W. et al. Inhibition of ABCG2-mediated transport by protein kinase inhibitors with a bisindolylmaleimide or indolocarbazole structure. Mol. Cancer Ther. 6, 1877-1885 (2007).] Recent studies have also identified targeted therapies, such as imatinib, sunitinib, erlotinib, and nilotinib, as substrates for BCRP and MDR1. In another study, it was discovered that over-expression of MDR/ABCB1 could result in NSCLC cell acquisition of paclitaxel resistance. [Yabuki N., et al., Gene amplification and expression in lung cancer cells with acquired paclitaxel resistance. Cancer Genet. Cytogenet. 2007; 173:1-9]

Inhibitors of multiple drug resistant proteins, such as zosuquidar and tariquidar, which are inhibitors of MDR1, have not had much success in achieving progression free survival in cancer patients. It is unclear whether this result shows the unimportance of such proteins, or whether there is a high degree of functional redundancy among family members. [Id. citing Pusztai, L. et al. Phase II study of tariquidar, a selective P-glycoprotein inhibitor, in patients with chemotherapyresistant, advanced breast carcinoma. Cancer 104, 682-691 (2005); Ruff, P. et al. A randomized, placebo-controlled, doubleblind phase 2 study of docetaxel compared to docetaxel plus zosuquidar (LY335979) in women with metastatic or locally recurrent breast cancer who have received one prior chemotherapy regimen. Cancer Chemother. Pharmacol. 64, 763-768 (2009); Szakacs, G. et al. Predicting drug sensitivity and resistance: profiling ABC transporter genes in cancer cells. Cancer Cell 6, 129-137 (2004).]

DNA Mutation and Repair

Cellular response to DNA damage may also play a role in formation of drug resistant cancer cells. Since many chemotherapy drugs induce DNA damage resulting in cell death, the capacity for a cancer cell to repair that damage can influence effectiveness of chemotherapy treatment. For example, some cancer cells display disruptions in the regulation of cell cycle arrest in response to DNA damage because of gain-of-function alterations in oncogenes and loss-of-function alterations in tumor suppressor genes. Also, synthetic lethality, which is present when dysfunction in at least one DNA repair mechanism makes a cell entirely dependent on an alternative DNA repair mechanism, may be exploited to kill cancer cells by disrupting particular protein targets necessary to the cell's remaining mechanism. However, in some circumstances, a cancer cell may acquire resistance to such targeting through mutation. For example, for cells exhibiting BRCA1 and BRCA2 mutations, inhibitors of DNA repair enzyme poly(ADP-ribose) polymerase 1 (PARP1) is useful for exploiting synthetic lethality by inhibiting the single-strand break repair mechanism. However, in-frame deletions of BRCA2 have been found to result in resistance to PARP1 inhibitors, because the in-frame deletion partially restores an alternative DNA repair mechanism function, thus eliminating synthetic lethality. [Farmer, H. et al. Targeting the DNA repair defect in BRCA mutant cells as a therapeutic strategy. Nature 434, 917-921 (2005); Edwards, S. L. et al. Resistance to therapy caused by intragenic deletion in BRCA2. Nature 451, 1111-1115 (2008); Sakai, W. et al. Secondary mutations as a mechanism of cisplatin resistance in BRCA2-mutated cancers. Nature 451, 1116-1120 (2008).]

Mismatch repair mechanism (MMR) is necessary for maintaining genomic integrity by correcting base-base mismatches and insertion/deletion mis-pairs created during DNA replication and recombination. MMR involves proteins PMS2, MLH1, MSH6, and MSH2, which recruit the enzyme EXO1 to recognize a mismatched base pair and excise the segment of the mutant strand. DNA polymerase then fills in the gap, repairing the strand. Alterations to MMR can lead to resistance to various cytotoxic drugs. For example, hypermethylation of MMR gene MLH1 can result in resistance to cisplatin and carboplatin. [Fink, D., Aebi, S. & Howell, S. B., The role of DNA mismatch repair in drug resistance. Clin. Cancer Res. 4, 1-6 (1998).]

"Genomic instability" refers to a high degree of mutations within the genome of a cellular lineage. The mutations that can occur include changes to nucleic acid sequences, chromosome rearrangements or aneuploidy. Genetic instability is a hallmark of cancer, and can result in increased tumor cell heterogeneity and increased resistance to chemotherapies and targeted therapies. For example, genomic instability has been associated with resistance to various taxanes and poor survival in various cancer types. [Id. citing Duesberg, P., Stindl, R. & Hehlmann, R. Explaining the high mutation rates of cancer cells to drug and multidrug resistance by chromosome reassortments that are catalyzed by aneuploidy. Proc. Natl Acad. Sci. USA 97, 14295-14300 (2000); Swanton, C. et al. Chromosomal instability determines taxane response. Proc. Natl Acad. Sci. USA 106, 8671-8676 (2009); Faragher, A. J. & Fry, A. M. Nek2A kinase stimulates centrosome disjunction and is required for formation of bipolar mitotic spindles. Mol. Biol. Cell 14, 2876-2889 (2003); Zhou, W. et al. NEK2 induces drug resistance mainly through activation of efflux drug pumps and is associated with poor prognosis in myeloma and other cancers. Cancer Cell 23, 48-62 (2013).]

Drug Resistance of Cancer Stem Cells

Cancer stem cells, also known as "tumor initiating cells" are believed to be a small population of tumor cells that have stem cell markers and have the ability to self-renew and give rise to progeny. In some cancers, cancer stem cells are the source of all tumor cells present in a malignant tumor, the source of cell resistance to chemotherapeutic agents used to treat a malignant tumor, and the source of cells that give rise to distant metastasis. [Dawood, S., Austin L., and Cristofanilli, M., Cancer Stem Cells: Implications for Cancer Therapy, Oncology, Dec. 15, 2014.] In that regard, there is a hierarchy within a tumor with unique self-renewing populations of cells at the top of the hierarchy and all other cells comprising the bulk of the tumor below. Under this model, non-stem cancer cells may be harmful, but cannot sustain damage to the body of a patient over a long period of time.

The concept of the cancer stem cell is important because many cancer therapies are judged by the ability to shrink the size of a tumor. But if those therapies are not able to target the small sub-population of cancer stem cells, then the tumor will eventually grow back. Furthermore, cancer stem cells can give rise to distant metastasis and can act as a reservoir for relapse of cancer after surgery, chemotherapy or radiation.

Cancer stem cells retain stem-like properties through dysregulation of signaling pathways and networks normally responsible for controlling self-renewal and differentiation. For example, activation of PI3K/AKT signaling pathway is involved in several cancer types, and has been found to lead to cellular transformation and tumorigenesis. An E17K mutation in AKT1 can result in an increase in anti-apoptotic protein Bcl-2 and phosphorylation of proapoptotic protein BAD, which results in resistance to apoptosis. Other member of the PI3K pathway, such as PTEN and mTOR, may contain mutations. For example, mutations in PTEN have been observed in various cancers such as T-cell acute lymphoblastic leukemia, glioblastoma and endometrial carcinoma. The JAK/STAT pathway may also be involved in tumorigenesis. Pim-1 and Pim-2 kinases have been show to aberrantly induce v-Abl dependent JAK/STAT signaling in pre-B cells, which is involved in cellular transformation. Furthermore, V617F mutation in JAK2 has been found to be a critical factor that contributes to malignant transformation of hematopoietic cells. [Chen, K, Huang, Y, Chen J, Understanding and targeting cancer stem cells: therapeutic implications and challenges, Acta Pharmacologica Sinica (2013) 34:732-740.]

In both cancer stem cells and normal stem cells, nuclear factor kappa B (NF-kappaB), a transcription factor that participates in the control of numerous genes, participates in the control of numerous cellular processes affecting the expression of many apoptosis related proteins like Bcl-xL, Bcl-2, survivin, cellular inhibitors of apoptosis (cIAPs), TRAF, among other. Studies have found that aberrant activation of NF-kappaB may be responsible for cancer development and progression and chemoresistance. [Chen, K, Huang, Y, Chen J, Understanding and targeting cancer stem cells: therapeutic implications and challenges, Acta Pharmacologica Sinica (2013) 34:732-740.]

Cancer stem cell populations may also be maintained via Notch, Hedgehog, and Wnt signaling pathways, which are known to be involved in self-renewal and differentiation. Studies have found that elevated Notch4 activity is present in breast cancer stem cells and that tumor initiation can be suppressed by inhibiting Notch4 activity. [Chen, K, Huang, Y, Chen J, Understanding and targeting cancer stem cells:

therapeutic implications and challenges, Acta Pharmacologica Sinica (2013) 34:732-740.]

Cancer stem cell properties may also be maintained through abnormal Wnt signaling, which has been found in various cancers such as leukemia, colon cancer, epidermal, breast, and cutaneous carcinoma. In human colon carcinoma, a defective mutation in the adenomatous polyposis coli (APC) gene stabilizes beta-catenin, thereby activating Wnt pathway mediated cell transformation. [Chen, K, Huang, Y, Chen J, Understanding and targeting cancer stem cells: therapeutic implications and challenges, Acta Pharmacologica Sinica (2013) 34:732-740.]

Cancer stem cell populations may have higher resistance to chemotherapy and/or radiation therapy. This may be attributed in part to their slower growth rate compared to other cell in the tumor, thus allowing more time for DNA repair and avoidance of apoptosis, [Leon G, et al. Cancer stem cells in drug resistant lung cancer: Targeting cell surface markers and signaling pathways, Pharmacol. Ther. 2015 Dec. 17. pii: S0163-7258(15)00227-2. doi: 10.1016/j.pharmthera.2015.12.001. Epub ahead of print.] and to cancer stem cells' ability to develop tumor cell heterogeneity, which is known to interfere with conventional chemotherapy, radiation therapy, and molecularly targeted therapy. [Id. citing Kreso, A., & Dick, J. E. (2014). Evolution of the cancer stem cell model. Cell Stem Cell 14(3), 275-291.] Also, the presence of ATP-binding cassette transporters (ABC transporters) are indicative of stemness in both normal cells and cancer cells, and promote drug resistance.

Tumor stem cells have been described in hematological malignancies such as acute myeloid leukemia (AML). Patients with AML are typically treated with chemotherapy, followed by hematopoietic stem cell transplantation. Studies have shown that AML cells have a stem cell hierarchy, and contain CD34+ stem cells that can sustain serial transplantation. Furthermore, studies have identified an association between the presence of CD34+CD38− cancer stem cells and a high frequency of minimal residual disease post treatment and poor prognosis. [Dawood, S., Austin L., and Cristofanilli, M., Cancer Stem Cells: Implications for Cancer Therapy, Oncology, Dec. 15, 2014.] The cells present in the minimal residual disease population were enriched with CD34+CD38− cancer stem cells, which have been found to be resistant to therapy with cytarabine. [Dawood, S., Austin L., and Cristofanilli, M., Cancer Stem Cells: Implications for Cancer Therapy, Oncology, Dec. 15, 2014.]

Cluster of differentiation 133 (CD133) is a marker associated with stemness in solid tumors. [Leon G, et al. Cancer stem cells in drug resistant lung cancer: Targeting cell surface markers and signaling pathways, Pharmacol. Ther. 2015 Dec. 17. pii: S0163-7258(15)00227-2. doi: 10.1016/j.pharmthera.2015.12.001. Epub ahead of print.] Studies have shown that lung cancer cells displaying CD133+ markers were resistant to successive treatment with chemotherapeutic agents such as cisplatin, etoposide, paclitaxel and gemcitabine. Studies have also shown increased tumorigenicity of lung cancer cells displaying CD133+ with its regulator aldehyde dehydrogenase (ALDH). [Id. citing Jiang, F., et al. (2009). Aldehyde dehydrogenase 1 is a tumor stem cell-associated marker in lung cancer. Molecular Cancer Research 7(3), 330-338.]

CD44 is another marker of stemness associated with drug resistance. CD44+ populations of NSCLC show enhanced tumor initiating capacity both in vivo and in vitro. [Id.] Furthermore, in SCLC, activation of CD44-MAPK-PI3K signaling causes increased expression of urokinase plasminogen activator (uPA), its receptor (uPAR) and MDR1, resulting in increased invasiveness and multi-drug resistance when treated with 5-fluorouracil (5-FU), cisplatin and etoposide. [Id. citing Gutova, M., et al. (2007) Identification of uPAR-positive chemoresistant cells in small cell lung cancer. PLoS One 2(2), 243.]

CD166 is another cancer stem cell marker associated with drug resistance. CD166, an immunoglobulin superfamily member of cell adhesion molecules (Ig-CAMs), mediates intercellular adhesion via hetero- or homophilic interactions (e.g. CD166-CD6 or CD166-CD166) and has been identified as conferring a stem cell phenotype to NSCLC cells. [Id. citing Zhang, W. et al., (2012). Glycine decarboxylase (GLDC) activity drives non-small cell lung cancer tumor-initiating cells and tumorigenesis. Cell 148(1-2), 259-272.] In tumor sphere formation experiments, CD166+ NSCLC cells required 100-fold fewer cells for initiation of the xenograft. In some studies $GLDC^{hi}$/CD166+ expression was found to be an indicator of shorter overall survival in NSCLC patients. Furthermore, chemical-induced hypoxia induced a stemness phenotype generated in lung adenocarcinoma cells, enhanced stem cell transcription factors and drug resistance. Cancer subpopulations expressing CD166 also showed greater drug resistance to cisplatin, docetaxel and pemetrexed relative to their CD166− counterparts. [Id. citing Zhao, M., et al. (2015). Hypoxia induced cell stemness leads to drug resistance and poor prognosis in lung adenocarcinoma. Lung Cancer 87(2), 98-106.]

CD90, which is a glycosylphosphatidylinsitol (GPI)-anchored glycoprotein responsible for cell-cell and cell-matrix interactions, has been identified in murine breast cancer stem cells and primary high-grade glioma cancer stem cells. [Id. citing Cho, R., Wang, X., Diehn, M., Shedden, K., Chen, G., Sherlock, G., et al. (2008). Isolation and molecular characterization of cancer stem cells in MMTV-Wnt-1 murine breast tumors. Stem Cells 26(2), 364-371; He, H. C., Chen, J. H., Chen, X. B., Qin, G. Q., Cai, C., Liang, Y. X., et al. (2012). Expression of hedgehog pathway components is associated with bladder cancer progression and clinical outcome. Pathology Oncology Research 18(2), 349-355; He, J., Liu, Y., Zhu, T., Zhu, J., DiMeco, F., Vescovi, A. L., et al. (2012). CD90 is identified as a candidate marker for cancer stem cells in primary high-grade gliomas using tissue microarrays. Molecular & Cellular Proteomics 11(6) (M111.010744).] CD90 has also been identified as a marker for stemness in NSCLC. [Id. citing Kuang, L. S., & Zhou, X. D. (2013). The relationship between tumor stem cells marker CD90 and resistance to cisplatin in human lung adenocarcinoma A549 cells. Tumor 33(9), 770-775; Yan, X., et al. (2013). Identification of CD90 as a marker for lung cancer stem cells in A549 and H446 cell lines. Oncology Reports 30(6), 2733-2740.] CD90+ NSCLC cell lines have been found to display a higher xenograft capacity than do CD90− counterparts after treatment with cisplatin. [Id. citing Wang, P., Gao, Q., Suo, Z., Munthe, E., Solberg, S., Ma, L., et al. (2013). Identification and characterization of cells with cancer stem cell properties in human primary lung cancer cell lines. PLoS One 8(3), e57020.]

Cancer stem cells may also express aldehyde dehydrogenase (ALDH) enzymes, which are putative stem cell markers associated with drug resistance in multiple cancer types. [Id.] In studies with NSCLC cells, high ALDH1 activity increased capacity for proliferation, self-renewal, differentiation, expression of stem cell marker CD133, and also displayed resistance to the chemotherapeutic drugs cisplatin, gemcitabine, vinorelbine, docetaxel, daunorubicin and doxorubicin, when compared to NSCLC cells lacking ALDH1 activity. [Id. citing Ucar, D., et al. (2009). Aldehyde dehydrogenase activity as a functional marker for lung cancer. Chemico-Biological Interactions 178(1-3), 48-55; Jiang, F., et al. (2009). Aldehyde dehydrogenase 1 is a tumor stem cell-associated marker in lung cancer. Molecular Cancer Research 7(3), 330-338.]

Cancer stem cells also display a higher level of expression of drug efflux proteins, which may confer inherent drug resistance. [Id. citing Shervington, A. & Lu, C. Expression of multidrug resistance genes in normal and cancer stem cells. Cancer Invest. 26, 535-542 (2008).] The presence of the cancer stem cell marker CD44 has been associated with overexpression of multiple drug resistance protein (e.g. BCRP) and a strong negative correlation with patient survival. [Id.]

A need remains for anti-cancer compounds that can overcome intrinsic or acquired resistance mechanisms of cancer cells alone or in combination with other anti-cancer agents. The described invention provides 6-mercaptopurine nucleoside analogues useful for this purpose.

SUMMARY

One aspect of the invention comprises a method for treating a resistant or refractory cancer exhibiting pronounced telomerase activity, the patient population being characterized by relapse of the cancer within six months of a first line anti-cancer agent (resistant) or no response to the first-line anticancer agent treatment (refractory), the method comprising administering to the subject a first amount or dose of a 6-mercaptopurine deoxyribonucleoside analogue selected from the group consisting of:

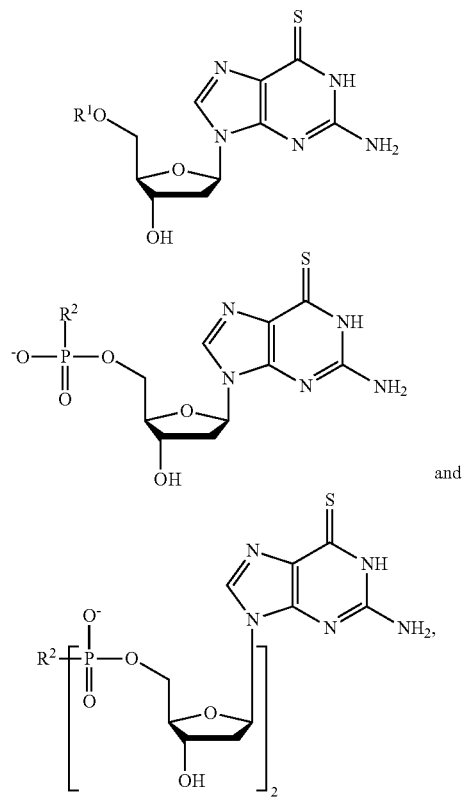

and, where $R_1$ is $-C(O)(CH_2)_nCH_3$ where n=6-16, and pharmaceutically acceptable salts or polymorphs thereof;

and where R2 is spermine or spermidine and pharmaceutically acceptable salts or polymorphs thereof; and a second amount or dose of an anti-cancer agent, wherein the first and second amounts or doses together comprise a therapeutically effective amount of a combination; wherein the combination is effective to: shorten telomere length; reduce size of a tumor; reduce growth rate of a tumor; reduce incidence of metastasis; promote an immune response; reduce progression of the cancer; increase lifespan of the subject; or a combination thereof.

According to some embodiments, the cancer is a carcinoma, a sarcoma, a leukemia, a lymphoma/myeloma or a brain/spinal cord cancer. According to some embodiments, the cancer comprises a solid tumor comprising tumor cells, a metastatic cancer comprising metastatic tumor cells, or a combination thereof. According to some embodiments, the 6-mercaptopurine ribonucleoside analogue is 6-thio-2'-deoxyguanosine. According to some embodiments, the amount or dose of the 6-mercaptopurine ribonucleoside analogue is about 0.5 mg/kg to about 3 mg/kg. According to some embodiments, the combination is administered intravenously or orally. According to some embodiments, the combination is administered by intratumoral injection. According to some embodiments, the subject is a human being. According to some embodiments, the anticancer agent of the second amount or dose is the first-line anticancer agent to which the cancer is refractory or resistant. According to some embodiments, the combination produces an additive effect. According to some embodiments, the combination produces a synergistic effect. According to some embodiments, the anti-cancer agent is selected from the group consisting of an alkylating agent, an antimetabolite agent, an anti-folate agent, a pyrmidine analog, a purine analog, an antimitotic agent, an epipodophyllotoxin agent; a camptothecin analog, an antibiotic agent, a biologic agent, an antiestrogen agent; a GnRH analog, an androgen analog, a somatostatin analog, a kinase inhibitor; an agent that forms a platinum coordination complex, and EDTA derivative; a platelet-reducing agent, a retinoid, and a histone deacetylase inhibitor.

One aspect of the invention comprises a method for treating a resistant or refractory cancer in a subject, the resistant or refractory cancer comprising one or more cells characterized by (i) a less than a 4 fold change in one or more of the genes listed in TABLE III, relative to the level of expression in one or more of cell lines H1792, HCC44, HCC4017, H2887, H358, H2009, HCC827, H2347, H2291, H1975, H1373, H2258, H2250, HCC4006, H2087, HCC193, H820, H441, HCC1897, HCC2450, HCC1195, H1666, Calu3, H2122, H647, H1437, PC 9, H1770, HCC1359, HCC461, H157, H2882, H920, H1944, A549, H460, H2073, H1395, HCC2108, HCC15, H1651, HCC366, H1355, HCC1313, HCC2814, HCC95, HCC4018, H1755, H520, H661, Calu6, H125, H1299, HCC2429, H1155; and (ii) a greater than −2 fold change in one or more of the genes listed in TABLE IV, relative to the level of expression in one or more of cell lines H1792, HCC44, HCC4017, H2887, H358, H2009, HCC827, H2347, H2291, H1975, H1373, H2258, H2250, HCC4006, H2087, HCC193, H820, H441, HCC1897, HCC2450, HCC1195, H1666, Calu3, H2122, H647, H1437, PC 9, H1770, HCC1359, HCC461, H157, H2882, H920, H1944, A549, H460, H2073, H1395, HCC2108, HCC15, H1651, HCC366, H1355, HCC1313, HCC2814, HCC95, HCC4018, H1755, H520, H661, Calu6, H125, H1299, HCC2429, H1155; the method comprising administering to the subject:

(a) an amount or dose of a 6-mercaptopurine deoxyribonucleoside analogue selected from the group consisting of:

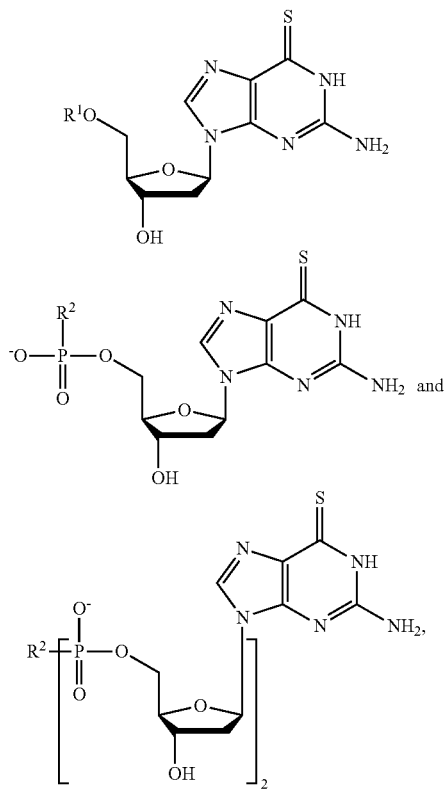

where $R^1$ is —C(O)(CH$_2$)$_n$CH$_3$ where n=6-16, and pharmaceutically acceptable salts or polymorphs thereof; and where $R^2$ is spermine or spermidine and pharmaceutically acceptable salts or polymorphs thereof; wherein the amount or dose of the 6-mercaptopurine deoxyribonucleoside analogue is effective to: (i) shorten telomere length; (ii) reduce size of a tumor; (iii) reduce growth rate of a tumor; (iv) reduce incidence of metastasis; (v) promote an immune response; (vi) reduce progression of the cancer; (vii) increase lifespan of the subject; or (viii) a combination thereof.

According to some embodiments, the cancer is a carcinoma, a sarcoma, a leukemia, a lymphoma/myeloma or a brain/spinal cord cancer. According to some embodiments, the cancer comprises a solid tumor comprising tumor cells, a metastatic cancer comprising metastatic tumor cells, or a combination thereof. According to some embodiments, the 6-mercaptopurine ribonucleoside analogue is 6-thio-2'-deoxyguanosine. According to some embodiments, the amount or dose of the 6-mercaptopurine ribonucleoside analogue is about 0.5 mg/kg to about 3 mg/kg. According to some embodiments, the combination is administered intravenously or orally. According to some embodiments, the subject is a human being.

BRIEF DESCRIPTION OF THE DRAWINGS

FIG. 1A shows the chemical structures of 6-thioguanine (6-thio-G) and 6-thio-deoxyguanosine (6-thio-dG).

FIG. 1B shows a graph demonstrating the cell counts of HCT116 and BJ cells treated with 6-thio-dG (3 μM) and 6-thio-G (3 μM) for 1 week (every 3 days). (Control; untreated)

FIG. 2 shows a time table of HCT116 cells treatment protocols with no drug (—), 6-thio-dG (6dG), GRN163L (Im) or combination of 6-thio-dG and GRN163L (combo). Each week 1×10$^6$ cells/sample were collected for TRF analysis. HCT116 cells were treated 10 μM 6-thio-dG for 12-16 weeks. After treating with 10 μM 6-thio-dG for 12 weeks, the cells were treated with combination of 10 μM 6-thio-dG and 3 μM GRN163L for 2-4 weeks or only GRN163L for 2-4 weeks or cessation of drug for 2-4 weeks. (Control; untreated). TRF analysis was used to ascertain telomere shortening at the end of each treatment protocol.

FIGS. 3A and 3B. (A) A comparative line graph showing the lag period between administration of a telomerase inhibitor and cell death for cells with short telomeres and long telomeres. (B) A comparative line graph showing the lag period between administration of a telomere-altering compound and cell death for cells with short telomeres and long telomeres.

FIGS. 7A and 7B. (A) Line graph showing a reduction in the rate of tumor growth in xenograft animal models with HCT116. (B) Line graph showing a reduction in the rate of tumor growth in xenograft animal models with A549 cells.

FIG. 11A and FIG. 11B show a graphical representation of predicted drug resistance NSCLC cell lines based on gene expression similarity to three known NSCLC resistant cell lines.

FIG. 12 shows the quantified cell survival of a panel of NSCLC cell lines arranged according to resistance to a 1 week treatment of 3 μM 6-thio-dG. The panel of NSCLC cell lines was treated with 3 μM 6-thio-dG every three days for one week. A cell count of viable cells was performed at the end of one week.

FIG. 13 shows the NSCLC cell lines that were determined to be resistant, intermediate sensitive, and very sensitive to 6-thio-dG treatment, after treatment 3 μM 6-thio-dG every three days for one week. IC50 values for each of a panel of tested cell lines are listed.

FIG. 14 shows the IC50 distribution, on a logarithmic scale, of 67 NSCLC cell lines treated with 6-thio-dG for 3-4 days. 6-thio-dG $IC_{50}$ values designated as "sensitive" are less than 3 μM. 6-thio-dG $IC_{50}$ values designated as "resistant" are greater than 10 μM. Cells having $IC_{50}$ values between 3 μM and 10 μM are somewhat sensitive.

FIG. 16 shows the experimental results of 6-thio-dG treatment on carboplatin/paclitaxel resistant NSCLC cell lines compared to controls. Cell lines normally sensitive to paclitaxel/carboplatin were treated with a clinically relevant 2:3 ratio over 8-9 months with incrementally increased doses to generate resistant lines. T[n] indicates the cell line variant developed after 'n' cycles of carboplatin/paclitaxel treatment. Resistance is shown compared to parental control (FIG. 16A and FIG. 16B). Cells which were identified as paclitaxel/carboplatin resistant were treated with three different concentrations of 6-thio-dG every three days for one week, and evaluated for survival (FIG. 16C and FIG. 16D).

FIG. 17 shows cellular doubling time (A) and measured telomere length (B) plotted against the IC50 values of various NSCLC cell lines (A549, Calu-3, Calu-6, H1155, H1355, H1395, H1437, H157, H1666, H1693, H1792, H1819, H1838, H1944, H1993, H2009, H2073, H2087, H2122, H2126, H2347, H2882, H2887, H3122, H322, H3255, H358, H460, H661, H727, HCC1359, HCC193, HCC2429, HCC44, HCC515, HCC827, HCC95). Average telomere length was determined by Telomere Restriction Fragment via Southern blot. The results suggest sensitivity to 6-thio-dG is independent of telomere length (FIG. 17B).

FIG. 20A shows sensitivity of isogenic pairs of cell lines to 6-thio-dG after pretreatment with 5-azacytidine. FIG. 20B shows sensitivity of H1993 6-thio-dG resistant cell line treated with JumonjiC demethylase inhibitor (10, 50, and 100 nM JIB-04) and 6-thio-dG (3 and 5 uM) for 5 days (drugs were added at the same time).

FIG. 21A show light microscopy images of cells treated with 6-thio-dG or control for 1 week and 10 weeks. FIG. 21B shows cell survival of 6-thio-dG and control treated cells for each of weeks 1 through 10.

FIG. 23 depicts data showing that HCT116 cells can acquire resistance or intrinsically develop resistance to 6-thio-dG. Sub clones #31, #8, #15, and #5 were treated with 3 uM 6-thio-dG for 1-4 weeks relative to DMSO:water control. At the end of treatment, a cell count was performed. The results show that sub clone #31, which was originally sensitive, acquired resistance. Clone #8, which was intrinsically resistant, remained so for the duration of the treatment.

FIG. 24 depicts data showing that the genes that are responsible for acquisition of the paclitaxel/carboplatin resistance are not responsible for the acquisition of 6-thio-dG resistance. Cell lines that are sensitive to paclitaxel/carboplatin standard chemotherapy were treated in vitro for 5-8 cycles to develop resistant cell lines. HCC4017 (A), H1693 (B), H1819 cell lines (C) treated with paclitaxel/carboplatin double therapy in clinically relevant 2:3 ratio for long-term with increasing doses. The effect of 6-thio-dG was tested with 3 different concentrations (1, 3 and 10 μM) on these paclitaxel/carboplatin resistant cell lines and found that while HCC4017 paclitaxel/carboplatin resistant cell line was still sensitive to 6-thio-dG, H1693 and H1819, parental and paclitaxel/carboplatin resistant cell lines were resistant to 6-thio-dG.

FIG. 25 depicts data showing 2652 genes differentially expressed for 6-thio-dG sensitive and resistant cell lines (NSCLC parental versus paclitaxel/carboplatin resistant) as determined by gene chip (Illumina WG-6 V3, Cat. No. BD101-0201, BD-101-0603). The hybridized chip was scanned using Illumina TotalPrep Kit (Ambion) Cat. No. AMIL1791 and Illumina Beadstation 500 Bead Array reader. Data acquisition for visualization and data mining was performed with BeadStudio (Illumina). Genes were

DETAILED DESCRIPTION OF THE INVENTION

Glossary

Figure 4:
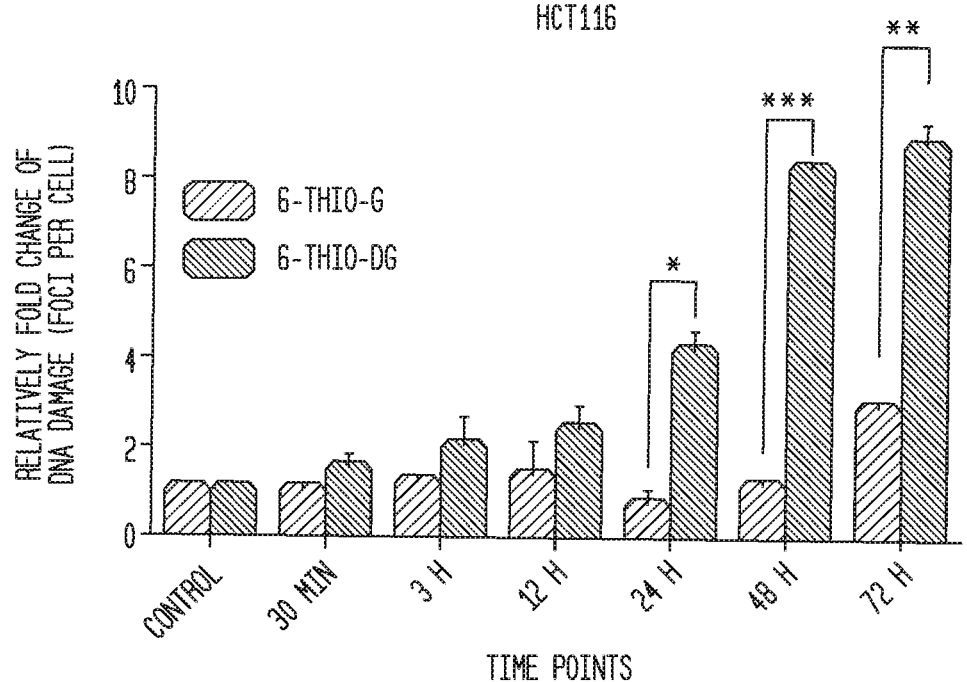
FIG. 4 shows DNA damage foci per cell. HCT116 cells treated with 6-thio-dG (3 μM) and 6-thio-G (3 μM) (n=75, SDs from two independent experiments). P=0.003, *P=0.0005, *P=0.0141 (6-thio-G versus 6-thio-dG), in the unpaired Student t test. ns, not significant differences in the unpaired Student t test. (Control; untreated).

The term "acyl" is used throughout the specification to describe a group at the 5' position of the nucleoside analog (e.g., at the free hydroxyl position in the sugar unit) which contains a C1 to C20 linear, branched or cyclic alkyl chain or a related group as otherwise described herein. The acyl group at the 5' position (R), in combination with the corresponding hydroxyl group results in an ester, which, after administration, may be cleaved to produce the free nucleoside form of the present invention.

The term "alkyl" shall mean within its context a C1-C20, preferably a C1-C10 linear, branch-chained or cyclic fully saturated hydrocarbon radical, which may be optionally substituted, such as with a phenyl group, for example. The term alkyl shall also embrace aralkyl groups such as benzyl groups, which phenyl group may be optionally substituted. Functional groups not expressly provided are understood to one of a hydrogen or alkyl group as defined herein. The term "ether" shall mean a C1 to C20 ether group, formed from an oxygen and an alkyl group at a position on the sugar moiety of compounds according to the present invention, and preferably contains at least one oxygen group within the alkyl chain.

The term "adjuvant therapy" as used herein refers to a treatment added to a primary treatment to prevent recurrence of a disease, or the additional therapy given to enhance or extend the primary therapy's effect, as in chemotherapy's addition to a surgical regimen.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "antagonist" as used herein refers to a small molecule, peptide, protein, or antibody that can bind to an enzyme, a receptor or a co-receptor, competitively or non-competitively through a covalent bond, ionic bond, hydrogen bond, hydrophobic interaction, or a combination thereof and either directly or indirectly deactivate a related downstream signaling pathway.

The term "additive effect" as used herein refers to the combined effect of two drugs predicted from the sum of the quantitative effects of the individual components.

The term "administering" and its various grammatical forms as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be administered by means such as, but not limited to, injection, implantation, grafting, topical application, or parenterally.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another:
Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).

The terms "analog" and "derivative" are used interchangeably to mean a compound produced from another compound of similar structure in one or more steps. A "derivative" or "analog" of a compound retains at least a degree of the desired function of the reference compound. Accordingly, an alternate term for "derivative" may be "functional derivative." Derivatives can include chemical modifications, such as akylation, acylation, carbamylation, iodination or any modification that derivatizes the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "antagonistic effect" as used herein refers to a less than expected additive effect when the drugs are evaluated in combination.

The term "anti-cancer effect" as used herein refers to a therapeutic effect that can include one or more of: inhibiting further growth of a tumor comprising tumor cells; reducing the likelihood of metastases; eliminating metastases; contributing to cell death in the tumor comprising tumor cells, or other cells with an abnormal activation of telomerase; shrinking the tumor comprising tumor cells; reducing the number of cancer cells; or reducing regrowth of a tumor comprising tumor cells after the patient's tumor or cancer is in remission.

The terms "apoptosis" or "programmed cell death" refer to a highly regulated and active process that contributes to biologic homeostasis comprising a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

The term "benign" or "nonmalignant" as used herein refers to being not cancerous. Benign tumors may grow larger but do not spread to other parts of the body.

The terms "cancer", "neoplasm" or "malignancy" are used interchangeably to refer to diseases in which abnormal cells divide without control and can invade nearby tissues. Cancer cells also can spread to other parts of the body through the blood and lymph systems. A carcinoma is a cancer that begins in the skin or in tissues that line or cover internal organs. A sarcoma is a cancer that begins in bone, cartilage, fat, muscle, blood vessels, or other connective or supportive tissue. A leukemia is a cancer that starts in blood-forming tissue such as the bone marrow, and causes large numbers of abnormal blood cells to be produced and enter the blood. A lymphoma and multiple myeloma are cancers that begin in cells of the immune system. A central nervous system cancer is a cancer that begins in the tissues of the brain and spinal cord.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "chemoresistance" as used herein refers to the development of a cell phenotype resistant to a variety of structurally and functionally distinct agents. Tumors can be intrinsically resistant prior to chemotherapy, or resistance may be acquired during treatment by tumors that are initially sensitive to chemotherapy. Drug resistance is a multifactorial phenomenon involving multiple interrelated or independent mechanisms. A heterogeneous expression of involved mechanisms may characterize tumors of the same type or cells of the same tumor and may at least in part reflect tumor progression. Exemplary mechanisms that can contribute to cellular resistance include: increased expression of defense factors involved in reducing intracellular drug concentration; alterations in drug-target interaction; changes in cellular response, in particular increased cell ability to repair DNA damage or tolerate stress conditions, and defects in apoptotic pathways.

The term "chemosensitive", "chemosensitivity" or "chemosensitive tumor" as used herein refers to a tumor that is responsive to a chemotherapy or a chemotherapeutic agent. Characteristics of a chemosensitive tumor include, but are not limit to, reduced proliferation of the population of tumor cells, reduced tumor size, reduced tumor burden, tumor cell death, and slowed/inhibited progression of the population of tumor cells.

The term "chemotherapeutic agent" as used herein refers to a chemical substance useful in the treatment or control of a disease, e.g., cancer.

The term "chemotherapy" as used herein refers to a course of treatment with one or more chemotherapeutic agents. In the context of cancer, the goal of chemotherapy is, e.g., to kill cancer cells, reduce proliferation of cancer cells, reduce growth of a tumor containing cancer cells, reduce invasiveness of cancer cells, increase apoptosis of cancer cells.

The terms "composition" and "formulation" are used interchangeably herein to refer to a product of the described invention that comprises all active and inert ingredients. The term "active" refers to the ingredient, component or constituent of the compositions of the described invention responsible for the intended therapeutic effect. The terms "pharmaceutical formulation" or "pharmaceutical composition" as used herein refer to a formulation or composition that is employed to prevent, reduce in intensity, cure or otherwise treat a target condition or disease.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by well known chemical modification methods (see, e.g., Glazer et al., Chemical Modification of Proteins, Selected Methods and Analytical Procedures, Elsevier Biomedical Press, New York (1975)).

The term "growth factor" as used herein refers to a substance that functions to regulate cell division and cell survival.

The term "hyperproliferative" as used herein refers to an abnormally high rate of cell proliferation by rapid division. A hyperproliferative disease state comprises a disease state in which cells are growing in an uncontrolled manner, whether that growth is cancerous or not.

Dose-effect curves. The intensity of effect of a drug (y-axis) can be plotted as a function of the dose of drug administered (X-axis). Goodman & Gilman's The Pharmacological Basis of Therapeutics, Ed. Joel G. Hardman, Lee E. Limbird, Eds., 10th Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug. Id. If the drug is to be administered by transdermal absorption, for example, a highly potent drug is required, since the capacity of the skin to absorb drugs is limited. The slope of the dose-effect curve reflects the mechanism of action of a drug. The steepness of the curve dictates the range of doses useful for achieving a clinical effect.

Biological variability. An effect of varying intensity may occur in different individuals at a specified concentration or a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the minimum effective concentration (MEC). Following administration of a dose of drug, its effects usually show a characteristic temporal pattern. A plot of drug effect vs. time illustrates the temporal characteristics of drug effect and its relationship to the therapeutic window. A lag period is present before the drug concentration exceeds the MEC for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accord to some embodiments, another dose of drug should be given to maintain concentrations within the therapeutic window.

The term "immunotherapeutics" refers to the use of immune effector cells and immune molecules to target and destroy cancer cells.

The term "maximal or clinical efficacy" refers to the maximal effect that can be produced by a drug. Maximal efficacy is determined principally by the properties of the drug and its receptor-effector system and is reflected in the plateau of the curve. In clinical use, a drug's dosage may be limited by undesired effects.

The term "malignant" as used herein refers to being cancerous. Malignant cells can invade and destroy nearby tissue and spread to other parts of the body.

The term "metastatic" as used herein refers to having to do with metastasis, which is the spread of cancer from the primary site (i.e., the place where it started) to other places in the body.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

The term "phosphodiester" describes mono-phosphate groups at the 5' position of the sugar unit which are diesterified such that the phosphate group is rendered neutral, i.e., has a neutral charge.

The term "proliferate" and its various grammatical forms as used herein refers to multiplying or increasing in number. Cell proliferation occurs by cell division.

The term "recurrent cancer" or "recurrence" refers to a cancer that has recurred (come back) usually after a period of time during which the cancer could not be detected. The cancer may come back to the same place as the original (primary) tumor or to another place in the body.

The term "refractory" refers to a disease or condition that does not respond to treatment. For example, a refractory cancer is a cancer that does not respond to treatment. The cancer may be resistant at the beginning of treatment or it may become resistant during treatment.

The term "resistant" and its other grammatical forms refer to a cancer that does not respond to treatment. The resistant cancer may be resistant at the beginning of treatment, or it may become resistant during treatment.

The term "subject" as used herein refers to either a human or non-human, such as primates, mammals, and vertebrates. According to some embodiments, the subject is a human.

The term "subject in need of such treatment" as used herein refers to (i) a patient who suffers from a tumor that is resistant to a chemotherapeutic agent; (ii) a subject who will be administered a compound of the described invention; (iii) is receiving at least one compound of the described invention; or (v) has received at least one compound of the described invention, unless the context and usage of the phrase indicates otherwise.

The term "synergistic effect" as used herein refers to a more than expected additive effect.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The terms "therapeutically effective amount", an "amount effective", or "pharmaceutically effective amount" of an active agent are used interchangeably to refer to an amount that is sufficient to provide the intended benefit of treatment. An effective amount of an active agent that can be employed according to the described invention generally ranges from generally about 0.01 mg/kg body weight to about 100 g/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

The term "treat" or "treating" includes abrogating, substantially inhibiting, slowing or reversing the progression of a disease, condition or disorder, substantially ameliorating clinical symptoms of a condition, substantially preventing the appearance of clinical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The described invention relates to 6-mercaptopurine ribonucleoside and analogues thereof for the treatment of tumors, cancer, and hyperproliferative diseases. According to some embodiments, without being limited by theory, compounds of the described invention can be converted into telomere substrates in vivo and can be recognized by telomerase for incorporation into telomeres of telomerase active cells, leading to induction of cell death of the telomerase active cells. While not wishing to be bound by any particular theory, incorporation of the described compounds into the telomere is believed to be an immediate teloemere DNA chain terminator and/or recognized as having telomeric DNA damage due to the altered telomere structure.

According to one aspect, the described invention provides compounds that can be administered to a subject in need of such treatment.

According to some embodiments, the compound is a compound according to Formula I below:

Formula I

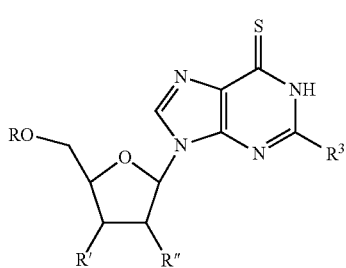

where R can be an H, hydroxyl group, an amino group, an alkyl amino group, a fluoride, an acyl group, a $C_1$-$C_{20}$ alkyl or ether group, a phosphate, diphosphate, triphosphate, phosphonate, or a phosphodiester group; where R' can be an H, a hydroxyl group, flouride group, a $C_1$-$C_{20}$ alkyl or ether group; where R" can be a hydroxyl group, a flouride, or an amino group in the ribo or arabino configuration; where $R^3$ can be an amino group or a alkyl-amino group; and phar- maceutically acceptable salts, solvates or polymorphs thereof. According to some embodiments, R. is H, R' is a hydroxyl group, and R" is H and such compounds are referred to herein as 6-thio-2'-deoxyguanosine.

According to some embodiments, the compound is a compound according to Formula II below:

Formula II

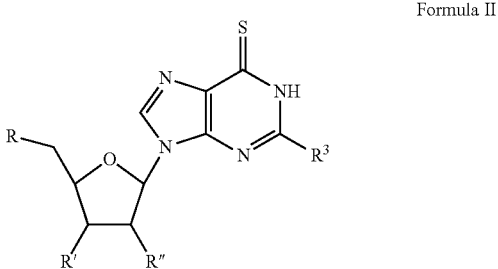

where R can be an H, an acyl group, a $C_1$-$C_{20}$ alkyl or ether group, a phosphate, diphosphate, triphosphate, phosphonate, or a phosphodiester group; where R' can be an H, a hydroxyl group, flouride, a $C_1$-$C_{20}$ alkyl or ether group; where R" can be a hydroxyl group, a flouride, or an amino group in the ribo or arabino configuration; where $R^3$ can be an amino group or a alkyl-amino group; and pharmaceutically acceptable salts, solvates or polymorphs thereof. According to some embodiments, R is H, R' is a hydroxyl group, and R" is H.

According to some embodiments, the compound is a compound according to Formula III below:

Formula III

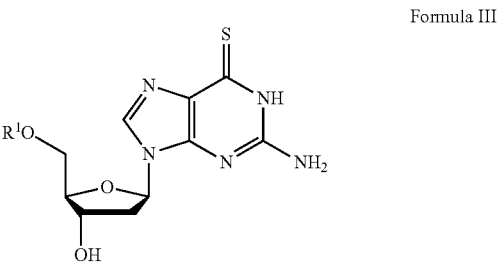

where $R^1$ can be H, or —C(O)(CH$_2$)$_n$CH$_3$, and where n=6-16. According to some such embodiments, such compounds are referred to herein as 6-thio-2'-deoxyguanosine.

According to some embodiments, the compound is a compound according to Formula IV below:

Formula IV

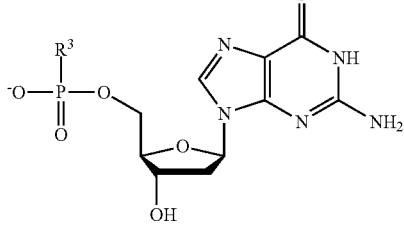

where $R^2$ can be spermine or spermidine. According to some embodiments, such compounds are referred to herein as 6-thio-2'-deoxyguanosine.

According to some embodiments, the compound is a compound according to Formula V below:

Formula V

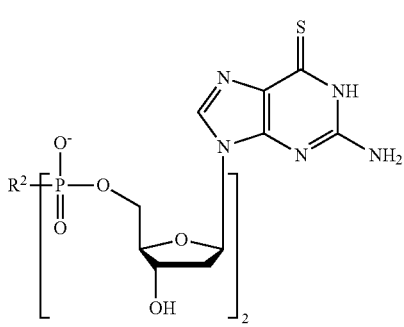

where $R^2$ can be spermine or spermidine and such compounds are referred to herein as 6-thio-2'-deoxyguanosine.

The described invention further provides pharmaceutical compositions comprising a therapeutic amount of a compound of Formula I, II, III, IV, or V and a carrier. According to some embodiments a therapeutic amount of the pharmaceutical composition is administered to the subject per day and the therapeutic amount comprises an amount between 0.5 mg of the analogue per 1 kg of subject to 3 mg of the analogue per 1 kg of subject. According to some embodiments, the pharmaceutical composition contains a therapeutic amount of one or more of the compounds of Formula I, II, III, IV, or V in combination with a therapeutic amount of at least one additional anti-cancer agent.

According to another aspect, the described invention provides a method for treating cancer and other hyperproliferative diseases, including tumors, e.g., malignant tumors and cancer, and any cell which possesses an over-activation of telomerase.

According to some embodiments, a method for treating a refractory cancer comprises administering a therapeutic amount of a 6-mercaptopurine ribonucleoside analogue and an anti-cancer agent. According to some embodiments, the method is effective to reduce drug resistance of the refractory cancer. Administration can occur simultaneously, serially, or in stages wherein the stages at least partially overlap in time or are spaced apart by a certain interval of time. According to some embodiments, the method is effective to provide an additive effect. According to some embodiments, the method is effective to provide a synergistic enhancement of the anticancer activity of one or both of the anti-cancer agents.

According to some embodiments, the therapeutic effect comprises i) acute cytotoxicity derived from anti-metabolic properties and incorporation into genomic DNA and ii) telomeric DNA modification and shortening.

According to some embodiments, the 6-thioguanosine analogues are effective as telomere disrupting compounds. For example, these analogues can be converted in vivo to 5'-triphosphate telomerase substrates, e.g., 2'-deoxyguanosine 5'-triphosphate, and incorporated into telomeres causing telomere shortening, telomere dysfunction, or both.

According to some embodiments, the pharmaceutical composition comprising a therapeutic amount of a 6-thioguanosine analogue of the described invention is effective to target cancer cells expressing telomerase. According to some embodiments, the effect of the pharmaceutical composition comprising the 6-thioguanosine analogues of the described invention on normal telomerase activity negative cells is less than the effect on target cancer cells. According to some embodiments, the pharmaceutical composition is effective to produce acute cell death in at least a portion or majority of telomerase active cells. According to some embodiments, the cell death can result from progressive telomere shortening or telomere dysfunction. According to some embodiments, the cell death can result from a telomere-associated DNA damage. According to some embodiments, the DNA damage comprises replacement of some guanine bases by 6-thio-guanine counterparts. According to some embodiments, the DNA damage response comprises alteration of the structure and function of the shelterin complex. According to some embodiments, compounds of the described invention may not cause any or may cause only a slight inhibition of measurable telomerase activity in vitro, as tested by Telomeric Repeat Amplification Protocol (TRAP) assay. According to some embodiments, the compounds of the described invention may cause genomic DNA damage.

According to some embodiments, modification of the compound of Formula I, II, III, IV, or V compounds, for example, at the 5' position, can affect the solubility, bioavailability and rate of metabolism of the active species, thus providing control over the delivery of the active species. According to some embodiments, the modification can affect the anticancer activity of the compound, in some cases increasing the activity over the unmodified compound. This can be assessed by preparing the derivative and testing its anticancer activity according to the methods described herein, or other method known to those skilled in the art.

According to some embodiments, the method comprises administering a therapeutic amount of a 2-amino-6-mercaptopurine ribonucleoside analogue to a subject having cancer cells. According to some embodiments, the therapeutic amount is effective to reduce the size of a tumor, reduce a reduction in the invasiveness of a tumor, reduction in the growth rate of the cancer, senescence of a portion of cells that exhibit an abnormal activation of telomerase, or prevention of metastasis or recurrence. Treatment of cancer may also refer to prolonging survival of a subject with cancer. As used herein, the phrase "effective amount" describes an amount of a compound which, in context, is used to produce or affect a therapeutic benefit.

According to some embodiments, the method can be used in the treatment of a cancer or other hyperproliferative disease state or in the treatment of cells exhibiting pronounced telomerase activity. According to some embodiments, the cancer may comprise a solid tumor comprising tumor cells, a metastatic cancer comprising metastatic tumor cells, or a non-metastatic cancer. According to some embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. According to some embodiments, a tumor can comprise a malignant or benign growth.

According to some embodiments, the cancer may be of a histological type, e.g., a; carcinoma; a sarcoma, a leukemia, a lymphoma/myeloma, or a brain/spinal cord cancer.

Examples of carcinomas include, without limitation, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; an adenocarcinoma; a gastrinoma, a cholangiocarcinoma; a hepatocellular carcinoma; a combined hepatocellular carcinoma and cholangiocarcinoma; a trabecular adenocarcinoma; an adenoid cystic carcinoma; an adenocarcinoma in adenomatous polyp; an adenocarcinoma, familial polyposis coli; a solid carcinoma; a carcinoid tumor; a branchiolo-alveolar adenocarcinoma; a papillary adenocarcinoma; a chromophobe carcinoma; an acidophil carcinoma; an oxyphilic adenocarcinoma; a basophil carcinoma; a clear cell adenocarcinoma; a granular cell carcinoma; a follicular adenocarcinoma; a non-encapsulating sclerosing carcinoma; adrenal cortical carcinoma; an endometroid carcinoma; a skin appendage carcinoma; an apocrine adenocarcinoma; a sebaceous adenocarcinoma; a ceruminous adenocarcinoma; a mucoepidermoid carcinoma; a cystadenocarcinoma; a papillary cystadenocarcinoma; a papillary serous cystadenocarcinoma; a mucinous cystadenocarcinoma; a mucinous adenocarcinoma; a signet ring cell carcinoma; an infiltrating duct carcinoma; a medullary carcinoma; a lobular carcinoma; an inflammatory carcinoma; paget's disease, a mammary acinar cell carcinoma; an adenosquamous carcinoma; an adenocarcinoma w/squamous metaplasia; a sertoli cell carcinoma; embryonal carcinoma; choriocarcinoma;

Examples of sarcomas include, without limitation, glomangiosarcoma; sarcoma; fibrosarcoma; myxosarcoma; liposarcoma; leiomyosarcoma; rhabdomyosarcoma; embryonal rhabdomyosarcoma; alveolar rhabdomyosarcoma; stromal sarcoma; carcinosarcoma; synovial sarcoma; hemangiosarcoma; kaposi's sarcoma; lymphangiosarcoma; osteosarcoma; juxtacortical osteosarcoma; chondrosarcoma; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; myeloid sarcoma; mast cell sarcoma;

Examples of leukemias include, without limitation, leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; and hairy cell leukemia.

Examples of lymphomas and myelomas include, without limitation, malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant melanoma; amelanotic melanoma; superficial spreading melanoma; malignant melanoma in giant pigmented nevus; epithelioid cell melanoma; multiple myeloma;

Examples of brain/spinal cord cancers include, without limitation, pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant;

Examples of other cancers include, without limitation, a thymoma; an ovarian stromal tumor; a thecoma; a granulosa cell tumor; an androblastoma; a leydig cell tumor; a lipid cell tumor; a paraganglioma; an extra-mammary paraganglioma; a pheochromocytoma; blue nevus, malignant; fibrous histiocytoma, malignant; mixed tumor, malignant; mullerian mixed tumor; nephroblastoma; hepatoblastoma; mesenchymoma, malignant; brenner tumor, malignant; phyllodes tumor, malignant; mesothelioma, malignant; dysgerminoma; teratoma, malignant; struma ovarii, malignant; mesonephroma, malignant; hemangioendothelioma, malignant; hemangiopericytoma, malignant; chondroblastoma, malignant; granular cell tumor, malignant; malignant histiocytosis; immunoproliferative small intestinal disease.

According to some embodiments, the pharmaceutical composition may be effective to treat a non-cancerous disease associated with activation of telomerase in inflammatory (leukocyte) cells (e.g., a fungal infection, a bacterial infection, a viral infection, acute and chronic inflammatory diseases such as inflammatory bowel disease (Crohn's disease, ulcerative colitis), rheumatoid arthritis and/or a neurodegenerative disease associated with inflammation).

According to some embodiments, the pharmaceutical composition may be effective to treat a hyperproliferative disease state, for example, psoriasis, genital warts, hyperproliferative keratinocyte diseases including hyperkeratosis, ichthyosis, keratoderma or lichen planus; and other chronic inflammatory diseases such as osteoarthritis hepatitis C virus (HCV) infections.

According to some embodiments, the pharmaceutical composition can be administered to a subject by any method known to those of ordinary skill in the art. According to some embodiments, the pharmaceutical composition can be administered intravenously, intradermally, intrathecally, intraarterially, intraperitoneally, intramuscularly, subcutaneously; orally, intrarectally, mucosally (intranasal, intravaginal, etc.), topically (i.e., transdermally), locally, via inhalation (e.g., aerosol inhalation), via injection, via infusion, via continuous infusion, via localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

According to some embodiments, the pharmaceutical composition may be formulated into a composition in a free base, neutral or salt form. According to some embodiments, pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. According to some embodiments, salts formed with the free carboxyl groups can also be derived from inorganic bases such as for example, sodium, potassium, ammonium, calcium or ferric hydroxides; or such organic bases as isopropylamine, trimethylamine, histidine or procaine. According to some embodiments, upon formulation, solutions will be administered in a manner compatible with the dosage formulation and in such amount as is therapeutically effective.

According to some embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. According to some embodiments, the proper fluidity can be maintained by the use of a coating, such as lecithin; by the maintenance of the required particle size by dispersion in carriers, such as liquid polyol or lipids; by the use of surfactants, such as hydroxypropylcellulose; or combinations thereof. According to some embodiments, isotonic agents, such as sugars, sodium chloride, or combinations thereof, are used.

According to some embodiments, the actual dosage amount of a composition in accordance with the described invention administered to subject can be determined by physical and physiological factors such as the specific compound employed, age, general health of the subject, diet, body weight, severity of condition, type of disease being treated, previous or concurrent therapeutic interventions, idiopathy of the patient, absorption rates, distribution rates, inactivation rates, excretion rates, time of administration, the route of administration, and on the judgment of the person supervising the administration. According to some embodiments, the dosage and the route of administration, the number of administrations of a preferred dosage, and/or an effective amount may vary according to the response of the subject. According to some embodiments, the active ingredient may be administered at once, or may be divided into a number of smaller doses to be administered at varying intervals of time. According to some embodiments, for any particular subject, specific dosage regimens could be adjusted over time according to the individual need and the professional judgment of the person administering or supervising the administration of the compositions, and that the concentration ranges set forth herein are exemplary only and are not intended to limit the scope or practice of the claimed composition.

According to some embodiments, the Formula I, II, III, IV, and/or V compound is included in the pharmaceutically acceptable carrier or diluent in an amount sufficient to deliver to a patient a therapeutically effective amount for the desired indication, without causing serious toxic effects in the patient treated. According to some embodiments, a dose of the active compound for all of the herein-mentioned conditions is in the range from about 10 ng/kg to 100 mg/kg, preferably 0.1 to 50 mg/kg per day, more generally 0.5 to about 25 mg per kilogram body weight of the subject per day. According to some embodiments, a typical dosage can range from 0.01-20% wt/wt in a suitable carrier. According to some embodiments, the compound can be administered in any suitable unit dosage form, including but not limited to one containing less than 1 mg, 1 mg to 3000 mg, or 5 to 1000 mg of active ingredient per unit dosage form.

According to some embodiments, compositions may be administered on an ongoing or continuous basis; on an as needed basis; or 1, 2, 3, 4, 5, 6, 7, 8, 9, 10, 11, 12, 13, 14, 15, 16, 17, 18, 19, 20 or more times. According to some embodiments, compositions may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more (or any value derivable therein). According to some embodiments, the composition may be administered once daily, twice daily, three times daily, four times daily, five times daily, or six times daily (or any range derivable therein) and/or as needed to the patient. According to some embodiments, a dose may be first administered before or after detection of a disease or health related condition or subsequent to a test where no disease indicators are detected. According to some embodiments, the patient can be administered a composition in cycles of days or weeks and in between each cycle no drug is administered. According to some embodiments, the time between each cycle can be days or weeks, e.g., 2-8 days/weeks. According to some embodiments, the patient is administered the composition for a certain period of time or with a certain number of doses after there is no detectable presence of a disease or disorder.

According to some embodiments, the composition may be administered to (or taken by) the patient about, at least about, or at most about 0.01-1000 µl/min, µl/hour, µl/day, µl/week, µl/month, ml/min, ml/hour, ml/day, ml/week, ml/month, µg/min, µg/hour, µg/day, µg/week, µg/month, mg/min, mg/hour, mg/day, mg/week, mg/month or any range derivable therein.

According to some embodiments, compositions of the described invention are combined with with a second treatment or pharmaceutical composition. According to some embodiments, a method of use can further include administration of a second pharmaceutical composition comprising an anti-cancer agent or other agent effective in the treatment of hyperproliferative disease. According to some embodiments, an anti-cancer agent can negatively affect cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. According to some embodiments, a second pharmaceutical composition can be administered in an effective amount or combined effective amount to kill or inhibit proliferation of certain cells.

According to some embodiments, a method of treatment can comprise a simultaneous co-administration. According to some embodiments, cells are contacted with a single composition or pharmaceutical formulation that includes both a Formula I, II, III, IV, and/or V compound and another anti-cancer agent, or by contacting the cell with two distinct compositions or formulations, at the same time, wherein one composition includes the Formula I, II, III, IV, and/or V compound and the other includes the second agent(s). According to some embodiments, two compositions can be administered not at the same time, but in temporal proximity to each other, e.g., on the same day or within the same week.

According to some embodiments a method of treatment can comprise a first stage wherein a pharmaceutical composition comprising a Formula I, II, III, IV, and/or V compound is administered and a second stage where a second pharmaceutical composition is administered. According to some embodiments, the first stage and the second stage may be sequential in time, spaced apart in time (minutes, days, weeks, or months), or overlapping in time. In addition, the sequential order of treatment stages can be reversed or repeated.

According to some embodiments, any combination of treatment stages may be employed. According to some embodiments, administration of a Formula I, II, III, IV, and/or V compound is "A" and the treatment with a secondary agent is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

According to some embodiments, administration of a pharmaceutical composition comprising a Formula I, II, III, IV, and/or V compound could be used in conjunction with a treatment B, such as gene therapy, chemotherapeutic, radiotherapeutic, or immunotherapeutic intervention, in addition to other pro-apoptotic or cell cycle regulating agents. It also is contemplated that various standard therapies, as well as surgical intervention, may be applied in combination with the described telomere shortening and telomere dysfunction-inducing therapy.

a. Chemotherapy

According to some embodiments, chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

b. Radiotherapy

According to some embodiments, radiotherapies can cause DNA damage and include what are commonly known as γ-rays, X-rays, and/or the directed delivery of radioisotopes to tumor cells. According to some embodiments, DNA damaging factors are also contemplated such as microwaves and UV-irradiation.

c. Immunotherapy

According to some embodiments, immunotherapy is used as part of a combined therapy, in conjunction with the administration of a pharmaceutical composition comprising a Formula I, II, III, IV, and/or V compound. According to some embodiments, immunotherapy modality relates to the targeting of the tumor cell through some marker of the tumor cell that is amenable to targeting, i.e., is not present on the majority of other cells. Many tumor markers exist and any of these may be suitable for targeting with a second treatment modality in the context of the described invention. According to some embodiments, the immunotherapy targets one or more of tumor markers carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Genes

According to some embodiments, the secondary treatment B is a gene therapy in which a therapeutic polynucleotide encoding all of part of a polypeptide is administered before, after, or at the same time as a pharmaceutical composition comprising a Formula I, II, III, IV, and/or V compound. According to some embodiments, delivery of vector encoding a certain gene product(s) related to the particular disease or health related condition can have a combined therapeutic effect, e.g., anti-proliferative effect, on target tissues.

e. Surgery

According to some embodiments, surgery is used in conjunction with a pharmaceutical composition comprising a Formula I, II, III, IV, and/or V compound. According to some embodiments, surgery includes resection in which all or part of cancerous tissue is physically removed, excised, and/or destroyed. According to some embodiments, tumor resection, which refers to physical removal of at least part of a tumor, is used in conjunction with a pharmaceutical composition comprising a Formula I, II, III, IV, and/or V compound. According to some embodiments, treatment by surgery includes laser surgery, cryosurgery, electrosurgery, and miscopically controlled surgery (Mohs' surgery). According to some embodiments, the composition of the described invention can be administered in conjunction with removal of superficial cancers, precancers, or incidental amounts of normal tissue. According to some embodiments, upon excision of part of all of cancerous cells, tissue, or tumor, a cavity may be formed in the body. According to some embodiments, treatment may be accomplished by administration of a pharmaceutical composition comprising a Formula I, II, III, IV, and/or V compound.

f. Other Anti-Cancer Agents

According to some embodiments, other anti-cancer agents may be used in combination with Formula I, II, III, IV, and/or V compositions of the described invention to additively or synergistically enhance the therapeutic efficacy of treatment.

According to some embodiments, one or more of the following anti-cancer agents may be used in combination with Formula I, II, III, IV, and/or V compositions of the described invention: immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. According to some embodiments, immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines.

According to some embodiments, Formula I, II, III, IV, and/or V compositions of the described invention may be used in combination with agents that up-regulate cell surface receptors or their ligands, such as Fas/Fas ligand, DR4 or DR5/TRAIL that potentiate the apoptotic inducing abilities of the described invention by establishment of an autocrine or paracrine effect on hyperproliferative cells. According to some embodiments, increases in intercellular signaling by elevating the number of GAP junctions increase the anti-hyperproliferative effects on the neighboring hyperproliferative cell population.

According to some embodiments, cytostatic or differentiation agents are used in combination with the described invention to improve the anti-hyperproliferative efficacy of the treatments. According to some embodiments, inhibitors of cell adhesion are used in combination with the described invention to improve the efficacy of the present invention. According to some embodiments, one or more of the following of cell adhesion inhibitors are used in combination with the described invention: focal adhesion kinase (FAKs) inhibitors and Lovastatin.

According to some embodiments, other anti-cancer agents that increase the sensitivity of a hyperproliferative cell to apoptosis are used in combination with the described invention, such as telomerase inhibitors like imetelstat sodium and signal transduction inhibitors like the antibody c225. As described in the Example section, below, According to some embodiments a clinically relevant combination of 6-thio-deoxyguanosine and imetelstat sodium have additive effects on telomere shortening in HCT116 cells. According to some embodiments, a method of treatment comprises administration of Formula I, II, III, IV, and/or V compound and a telomerase inhibiting composition such as imetelstat sodium, whether simultaneously, sequentially or both.

According to some embodiments, Formula I, II, III, IV, and/or V compound is used in combination with one or more of anti-cancer agents broadly characterized as anti-metabolites, inhibitors of topoisomerase I and II, alkylating agents, and microtubule inhibitors (e.g., taxol). According to some embodiments, Formula I, II, III, IV, and/or V compound is used in combination with one or more of Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

According to some embodiments, hormonal therapy is used in combination with the administration of a pharmaceutical composition comprising a Formula I, II, III, IV, and/or V compound. According to some embodiments, the use of hormones may be employed in the treatment of certain cancers such as breast, prostate, ovarian, or cervical cancer to lower the level or block the effects of certain hormones such as testosterone or estrogen.

Preparation and Administration of the Active Compounds and Compositions Formula I, II, III, IV, or V can be prepared according to the methods disclosed in detail in the art or by any other method known to those skilled in the art. In the case of compounds which contain two active agents, linking of a Formula I, II, III, IV, and/or V compound to another active agent may be readily accomplished following standard techniques. Appropriate blocking groups and agents to form the linking groups may be used readily.

Treatment of Disease with Intrinsic or Acquired Resistance

According to some embodiments, pharmaceutical compositions of the described invention are administered to treat a cancer or proliferative disease that has cells with acquired resistance to one or more anti-cancer agents or anti-proliferation agents.

According to some embodiments, pharmaceutical compositions of the described invention are administered to treat a cancer that has acquired resistance to one or more anti-cancer agents after being treated for 1 week or more with the anti-cancer agent. According to some embodiments, pharmaceutical compositions of the described invention are administered to treat a cancer that has acquired resistance to one or more anti-cancer agents after being treated for 2 weeks or more with the anti-cancer agent. According to some embodiments, pharmaceutical compositions of the described invention are administered to treat a cancer that has acquired resistance to one or more anti-cancer agents after being treated for 3 weeks or more with the anti-cancer agent. According to some embodiments, pharmaceutical compositions of the described invention are administered to treat a cancer that has acquired resistance to one or more anti-cancer agents after being treated for 1 month or more with the anti-cancer agent. According to some embodiments, pharmaceutical compositions of the described invention are administered to treat a cancer that has acquired resistance to one or more anti-cancer agents after being treated for 2 months or more with the anti-cancer agent. According to some embodiments, pharmaceutical compositions of the described invention are administered to treat a cancer that has acquired resistance to one or more anti-cancer agents after being treated for 3 months or more with the anti-cancer agent. According to some embodiments, pharmaceutical compositions of the described invention are administered to treat a cancer that has acquired resistance to one or more anti-cancer agents after being treated for 4 months or more with the anti-cancer agent. According to some embodiments, pharmaceutical compositions of the described invention are administered to treat a cancer that has acquired resistance to one or more anti-cancer agents after being treated for 5 months or more with the anti-cancer agent. According to some embodiments, pharmaceutical compositions of the described invention are administered to treat a cancer that has acquired resistance to one or more anti-cancer agents after being treated for 6 months or more with the anti-cancer agent. According to some embodiments, pharmaceutical compositions of the described invention are administered to treat a cancer that has acquired resistance to one or more anti-cancer agents after being treated for 7 months or more with the anti-cancer agent. According to some embodiments, pharmaceutical compositions of the described invention are administered to treat a cancer that has acquired resistance to one or more anti-cancer agents after being treated for 8 months or more with the anti-cancer agent. According to some embodiments, pharmaceutical compositions of the described invention are administered to treat a cancer that has acquired resistance to one or more anti-cancer agents after being treated for 9 months or more with the anti-cancer agent. According to some embodiments, pharmaceutical compositions of the described invention are administered to treat a cancer that has acquired resistance to one or more anti-cancer agents after being treated for 10 months or more with the anti-cancer agent. According to some embodiments, pharmaceutical compositions of the described invention are administered to treat a cancer that has acquired resistance to one or more anti-cancer agents after being treated for 11 months or more with the anti-cancer agent. According to some embodiments, pharmaceutical compositions of the described invention are administered to treat a cancer that has acquired resistance to one or more anti-cancer agents after being treated for 12 months or more with the anti-cancer agent.

According to some embodiments, pharmaceutical compositions of the described invention are administered to treat a cancer or proliferative disorder that has intrinsic or acquired resistance to one or more anti-cancer agents. According to some embodiments, pharmaceutical compositions of the described invention are administered to treat a cancer or proliferative disorder that has intrinsic or acquired resistance to one or more targeted therapies. According to some embodiments, pharmaceutical compositions of the described invention are administered to treat a cancer or proliferative disorder that has intrinsic or acquired resistance to one or more standard chemotherapies.

According to some embodiment, pharmaceutical compositions of the described invention are administered to treat a cancer or proliferative disorder that comprises cells with intrinsic or acquired resistance to one or more of the following categories of anti-cancer agents:

1. Alkylating Agents

Alkylating agents used in chemotherapy encompass a diverse group of chemicals that have in common the capacity to contribute, under physiological conditions, alkyl groups to biologically vital macromolecules, such as DNA. For several of the most valuable agents, such as cyclophosphamides and nitrosoureas, the active alkylating moieties are generated in vivo after complex metabolic reactions. There are five major types of alkylating agents used in chemotherapy of neoplastic diseases: (1) nitrogen mustards; (2) ethylenimimes; (3) alkyl sulfonates; (4) nitrosoureas; and (5) triazenes. Examples of alklyating agents include, but are not limited to, cyclophosamide (Cytotaxan®), a synthetic alkylating agent chemically related to the nitrogen mustards; temozolomide (Temodar®), a triazene analog of dacarbazine; busulfan (Myleran®), a synthetic derivative of dimethane sulfonate; ifosfamide (Ifex®), a synthetic analog of cyclophosaphamide; mesna (Mesnex®), a sulfhydryl compound; melphalan hydrochloride (Alkeran®), an orally available phenylalanine derivative of nitrogen mustard; and the nitrosoureas carmustine (BiCNU®) and lomustine (CEENU®).

2. Antimetabolites

Antimetabolites are a class of drugs that interfere with DNA and RNA growth by preventing purines (azathioprine, mercaptopurine) or pyrimidine from becoming incorporated into DNA during the S phase of the cell cycle, thus stopping normal development and division. Antimetabolites commonly are used to treat leukemias, tumors of the breast, ovary and the intestinal tract, as well as other cancers.

Antimetabolites include folic acid analogs, such as methotrexate and aminopterin; pyrimidine analogs, such as fluorouracil and fluorodeoxyuridine; cytarabine (cytosine arabinoside); and purine analogs, such as mercaptopurine, thioguanine, fludarabine phosphate, pentostatin (2'-deoxycoformycin), and cladribine.

2.1. Anti-Folates

Folic acid is an essential dietary factor from which is derived a series of tetrahydrofolate cofactors that provide single carbon groups for the synthesis of precursors of DNA (thymidylate and purines) and RNA (purines). The enzyme dihydrofolate reductase ("DHFR") is the primary site of action of most anti-folates. Inhibition of DHFR leads to toxic effects through partial depletion of tetrahydrofolate cofactors that are required for the synthesis of purines and thymidylate.

Examples of anti-folates include, but are not limited to, methotrexate and Pemetrexed disodium. The most commonly used anti-folate is methotrexate (methotrexate sodium, amethopterin, Folex®, Mexate®, Rheumatrex®, which is an antimetabolite and antifolate agent with antineoplastic and immunosuppressant activities. Pemetrexed disodium (Alimta®) is the disodium salt of a synthetic pyrimidine-based antifolate.

2.2. Pyrmidine Analogs

Pyrmidine analogs are a diverse group of drugs with the capacity to inhibit biosynthesis of pyrimidine nucleotides or to mimic these natural metabolites to such an extent that the analogs interfere with the synthesis or function of nucleic acids. Drugs in this group have been employed in the treatment of diverse afflictions, including neoplastic diseases, psoriasis and infections caused by fungi and DNA-containing viruses.

Examples of pyrimidine analogs include, but are not limited to, 5-Fluorouracil (fluorouracil, 5-FU, Adrucil®, Efudex®, Fluorplex®), an antimetabolite fluoropyrimidine analog of the nucleoside pyrimidine with antineoplastic activity; floxuridine, a fluorinated pyrimidine monophosphate analogue of 5-fluoro-2'-deoxyuridine-5'-phosphate (FUDR-MP) with antineoplastic activity; capecitabine (Xeloda®), an antineoplastic fluoropyrimidine carbamate; and gemcitabine hydrochloride (Gemzar®), the salt of an analog of the antimetabolite nucleoside deoxycytidine with antineoplastic activity.

2.3. Purine Analogs

Several analogs of natural purine bases, nucleosides and nucleotides useful in the treatment of malignant diseases (mercaptopurine, thioguanine) and for immunosuppressive (azatioprine) and antiviral (acyclovir, ganciclovir, vidarabine, zidovudine) therapies have been identified.

The purine analogs mercaptopurine and its derivative azatioprine are among the most clinically useful drugs of the antimetabolite class. Examples of purine analogs include, but are not limited to, mercaptopurine (Purinethol®), a thiopurine-derivative antimetabolite with antineoplastic and immunosuppressive activities; decitabine (Dacogen®), a cytidine antimetabolite analogue with potential antineoplastic activity; and dacarbazine (DTIC-DOME®), a triazene derivative with antineoplastic activity.

3. Natural Products

Many chemotherapeutic agents are found or derived from natural resources. Antimicrotubule molecules, such as paclitaxel or vinca alkaloids, can cause sinus bradycardia, atrioventricular block, ventricular tachycardia, hypotension, congestive heart failure and ischemia. See Yeh, E T, et al., Circulation 109 (25): 3122-31 (2004). Mitomycin, for example, has been associated with the development of caradiomyopathy, especially when given with or after an anthracycline. Buzdar, A. U., et al. Cancer Treat. Rep. 62: 1005-1008 (1978).

3.1. Antimitotic Drugs 3.1.1. Vinca Alkaloids and their Side-Effects

The vinca alkaloids, cell-cycle-specific agents that, in common with other drugs, such as colchicine, podophyllotoxin, and taxanes, block cells in mitosis, exerts their biological activities by specifically binding to tubulin, thereby blocking the ability of protein to polymerize into microtubules, and arresting cell division in metaphase through disruption of the microtubules of the mitotic apparatus. In the absence of an intact mitotic spindle, the chromosomes may disperse throughout the cytoplasm or may clump in unusual groupings. Both normal and malignant cells exposed to vinca alkaloids undergo changes characteristic of apoptosis.

Examples of vinca alkaloids include, but are not limited to, vincristine sulfate, a salt of a natural alkaloid isolated from the plant *Vinca rosea* Linn; vinblastine, a natural alkaloid isolated from the plant *Vinca rosea* Linn; and vinorelbine. Both vincristine and vinblastine, as well as the analog vinorelbine, have potent and selective antitumor effects, although their actions on normal tissue differ significantly.

3.1.2. Taxanes

The taxanes include, for example, but not limited to, paclitaxel, extracted from the Pacific yew tree *Taxus brevifolia*, and docetaxel (Taxotere®), a semi-synthetic, second-generation taxane derived from a compound found in the European yew tree *Taxus baccata*.

3.2. Epipodophyllotoxins

Podophyllotoxin is the active principle extracted from the mandrake plant *Podophyllum peltatum* from which two semisynthetic glycosides, etoposide and teniposide, have been developed.

3.3. Camptothecin Analogs

Camptothecins target the enzyme topoisomerase I. The parent compound, camptothecin, was first isolated from the Chinese tree *Camptotheca acuminata*. Although the parent camptothecin compound demonstrated antitumor activity, its severe and unpredictable toxicity, principally myelosuppression and hemorrhagic cystitis limited its use. The most widely used camptothecin analogs are irinotecan and toptecan, which are less toxic and more soluble.

3.4. Antibiotics

Antitumor antibiotics are compounds that have cytotoxic as well as antimicrobial properties. Most commonly used in neoplastic disease treatment are the actinomycins and anthracyclines. Examples include Mitroxantrone, which is a derivative of anthraquinone (9,10 dioxoantrhacene, also known as 9,10-anthracenedione, anthradione, 9,10-anthrachinon, anthracene-9,10-quinone, 9,10-dihydro-9,10-dioxoanthracene, and trade names Hoelite, Morkit and Corbit.

3.4.1. Actinomycin

An exemplary actinomycin includes Dactinomycin (Actinomycin D), produced by *Streptomyces parvullus*. This highly toxic agent inhibits rapidly proliferating cells of normal and neoplastic origin.

3.4.2. Anthracyclines

The anthracycline antibiotics and their derivatives are important antitumor agents. They are produced by the fungus *Streptomyces peucetius* var. *caesius*. Anthracyclines and anthracenediones can intercalate with DNA. Accordingly, many functions of DNA are affected, including DNA and RNA synthesis. Single-strand and double-strand breaks occur, as does sister chromatid exchange; thus these compounds are both mutagenic and carcinogenic. Scission of DNA is believed to be mediated by drug binding to DNA and topoisomerase II that prevents the resealing of DNA breaks created by the enzyme.

Examples of anthracyclines include, but are not limited to, idarubicin hydrochloride, a semisynthetic 4-demethoxy analog of daunorubicin (daunorubicin hydrochloride, daunomycin, rubidomycin; Cerubidine®); doxorubicin (doxorubicin hydrochloride, Adriamycin®, Rubex®); as well as several analogs of doxorubicin including valrubicin (Valstar®) (for intravescial therapy of BCG-refractory urinary bladder carcinoma) and epirubicin (4'-epidxorubicin, Ellence®) (as a component of adjuvant therapy following resection of early lymph-node-positive breast cancer).

Additional antibiotic antineoplastics include, but are not limited to, mitoxantrone (Novotrone®), an anthracenedione; and bleomycin antibiotics, fermentation products of *Streptomyces verticillus* that cleave DNA, and includes bleomycin sulfate (Blenoxane®); and mitomycin (mitomycin-C, Mutamycin®), an antibiotic isolated from *Streptomyces caespitosus*.

4. Biologics

Generally, the term "biologics" refers to compounds that are produced by biological processes, including those utilizing recombinant DNA technology. Biologic compounds include agents or approaches that beneficially affect a patient's biological response to a neoplasm. Included are agents that act indirectly to mediate their anti-tumor effects (e.g., by enhancing the immunological response to neoplastic cells) or directly on the tumor cells (e.g., differentiating agents). Examples of antineoplastic biologics include, but are not limited to, Filgrastim (Neupogen®), a recombinant granulocyte colony-stimulating factor (G-CSF); and Sargramostim (Leukine®), a recombinant granulocyte/macrophage colony-stimulating factor (GM-CSF).

Examples of antineoplastic monoclonal antibodies include, but are not limited to, Bevacizumab (Avastin®), a recombinant humanized monoclonal IgG antibody that binds to and inhibits the biologic activity of human vascular endothelial growth factor ("VEGF") in in vitro and in vivo assay systems, and Panitumumab (Vectibix®), a human monoclonal antibody produced in transgenic mice that attaches to the transmembrane epidermal growth factor (EGF) receptor.

5. Hormones and Related Agents

Several chemotherapeutic agents exert their therapeutic effect through interactions with hormones and related agents. Antiestrogens are modulators of the estrogen receptor. Estrogens are the family of hormones that promote the development and maintenance of female sex characteristics.

Examples of antiestrogens include, but are not limited to, tamoxifen citrate (Nolvadex®), a competitive inhibitor of estradiol binding to the estrogen receptor ("ER").

Gonadotropin-releasing hormone ("GnRH") analogs are synthetic peptide drugs modeled after human GnRH. They are designed to interact with GnRH receptor. The analogs of GnRH peptide include leuprolide (Lupron®, Eligard®), goserelin (Zoladex®), triptorelin (Trelstar Depot®) and buserelin (Suprefact®).

Examples of gonadotropin-releasing hormone analogs include Leuprolide acetate, the salt of a synthetic nonapeptide analog of gonadotropin-releasing hormone.

Examples of antineoplastic androgens include, but are not limited to, fluoxymesterone (Halotestin®), a halogenated derivative of 17-alpha-methyltestosterone. Additional antiandrogen agents, include, but are not limited to, megestrol acetate, the salt of megestrol, a synthetic derivative of the naturally occurring female sex hormone progesterone, with progestogenic, antiestrogenic, and antineoplastic activities.

Examples of somatostatin analogs include, but are not limited to, octreolide acetate (Sandostatin LAR® Depot), the salt of a synthetic long-acting cyclic octapeptide with pharmacologic properties mimicking those of the natural hormone somatostatin.

6.1. Kinase Inhibitors

Antineoplastic kinase inhibitors include, but are not limited to, Sorafenib tosylate (Nexavar®), a synthetic compound that targets growth signaling and antiogenesis, and Erlotinib hydrochloride (Tarceva®), the salt of a quinazoline derivative with antineoplastic properties.

6.2. Platinum Coordination Complexes

Examples of antineoplastic agents that form platinum coordination complexes include, but are not limited to, Cisplatin (cis-diamminedichloroplatinum (II), Platinol-AQ®), a divalent inorganic water-soluble, platinum containing complex that appears to enter cells by diffusion and reacts with nucleic acids and proteins, is a component of several combination chemotherapy regimens. For example, it is used with bleomycin, etoposide and vinblastine for treating patients with advanced testicular cancer, and with paclitaxel, cyclophosphamide or doxorubicin for treating ovarian cancer.

Another antineoplastic agent that forms a platinum coordination complex is Carboplatin (CBDCA, JM-8), which has a mechanism and spectrum of clinical activity similar to cisplatin, but generally is less reactive than cisplatin.

An additional antineoplastic agent is Oxaliplatin (trans-1-diaminocyclohexane oxalatoplatinum), which, like cisplatin, has a wide range of antitumor activity and is active in ovarian cancer, germ-cell cancer and cervical cancer. Unlike cisplatin, oxaliplatin in combination with 5-fluorouracil is active in colorectal cancer.

6.3. EDTA Derivatives

Other antineoplastic agents include EDTA-derivatives. Such compounds include, but are not limited to, Dexrazoxane hydrochloride (Zincard®), the salt of a bisdioxopiperazine with iron-chelating, chemoprotective, cardioprotective, and antineoplastic activities.

6.4. Platelet-Reducing Agent

Anagrelide hydrochloride (Agrlyin®) is a platelet-reducing agent used to treat thrombocythemia, secondary to myeloproliferative disorders, to reduce the elevated platelet count and the risk of thrombosis and to ameliorate associated symptoms including thrombo-hemorrhagic events.

6.5. Retinoids

Retinoids are a group of substances related to vitamin A and function like vitamin A in the body. Retinoids include, but are not limited to, bexarotene (Targretin®), a synthetic retinoic acid agent with potential antineoplastic, chemopreventive, teratogenic and embryotoxic properties; and isotretinoin (Accutane®), a naturally-occurring retinoic acid with potential antineoplastic activity.

6.6. Histone Deacetylase Inhibitors

The histone deacetylase inhibitor vorinostat (Zolinza®) is a synthetic hydroxamic acid derivative with antineoplastic activity, and a second generation polar-planar compound that binds to the catalytic domain of the histone deacetylases (HDACs). This allows the hydroxamic moiety to chelate zinc ion located in the catalytic pockets of HDAC, thereby inhibiting deacetylation and leading to an accumulation of both hyperacetylated histones and transcription factors. Hyperacetylation of histone proteins results in the upregulation of the cyclin-dependent kinase p21, followed by G1 arrest. Hyperacetylation of non-histone proteins such as tumor suppressor p53, alpha tubulin, and heat-shock protein 90 produces additional anti-proliferative effects. Vorinostat also induces apoptosis and sensitizes tumor cells to cell death processes.

One or more of the organometallic complexes of the present invention can be administered in combination with agents that cause a change to chromatin structure. Exemplary chromatin remodeling agents include agents undergoing clinical trials such as Vorinostat, Romidepsin, Panobinostat, Valproic acid, Belinostat, Mocetinostat (MGCD0103), Abexinostat (PCI-24781), Entinostat (MS-275), SB939, Resminostat (4SC-201), Givinostat (ITF2357), Quisinostat (JNJ-26481585), Kevetrin, CUDC-101, AR-42citenote-46, CHR-2845, CHR-3996citenote-50, 4SC-202, CG200745, ACY-1215, ME-344, sulforaphanecite_note-Tan2010-34, and Givinostat (ITF2357).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

According to some embodiments, pharmaceutical compositions of the described invention are administered to treat a cancer or proliferative disorder that has cells with intrinsic or acquired resistance to one or more of a targeted therapy or standard chemotherapy. According to some embodiments, pharmaceutical compositions of the described invention are administered to treat a cancer or proliferative disorder that has cells with intrinsic or acquired resistance to one or more of the following compounds: cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate; tumor necrosis factor; interferon alpha, beta, and gamma; IL-2 and other cytokines; F42K and other cytokine analogs; or MIP-1, MIP-1beta, MCP-1, RANTES, and other chemokines; anti-metabolites, inhibitors of topoisomerase I and II, alkylating agents and microtubule inhibitors; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; and zoledronate.

According to some embodiments, pharmaceutical compositions of the described invention are administered to treat cancer cells having intrinsic or acquired resistance to an anti-cancer compound via one or more of: alteration of a drug target through secondary mutations, activation of bypass biological pathways, activation of downstream effectors that prevent cell death, epigenetic changes, alterations to drug transport and metabolism, changes to DNA mutation and repair mechanisms, and alteration to tumor cell microenvironment.

According to some embodiments, pharmaceutical compositions of the described invention are administered to treat a cancer that has acquired resistance to one or more anti-cancer compounds. According to some embodiments, the cancer comprises cells that have a G2032R mutation in the ROS proto-oncogene 1 (ROS 1). According to some embodiments, the cancer comprises cells that have a S492R mutation in EGFR. According to some embodiments, the cancer comprises cells that have a mutation in Phosphatidylinositol-4,5-bisphosphate 3-kinase catalytic subunit alpha (PIK3CA). According to some embodiments, the cancer comprises cells that over express multi-drug resistance protein 1 (MDR1). According to some embodiments, the cancer comprises cells that over express multi-drug resistance-associated protein 1 (MRP1). According to some embodiments, the cancer comprises cells that over express breast cancer resistance protein (BCRP). According to some embodiments, the cancer comprises cells that over express thymidylate synthase. According to some embodiments, the cancer comprises cells that over express androgen receptor (AR). According to some embodiments, the cancer comprises cells that have a missense mutation at T315 of BCR-ABL1. According to some embodiments, the cancer comprises cells that have hypermethylation of the mismatch repair mechanism gene MLH1.

According to some embodiments, pharmaceutical compositions of the described invention are administered to treat a non-small cell lung cancer that has acquired drug resistance. According to some embodiments, the non-small cell lung cancer comprises cells that have acquired the T790M mutation to EGFR. According to some embodiments, the non-small cell lung cancer comprises cells that have the D761Y mutation to EGFR. According to some embodiments, the non-small cell lung cancer comprises cells that have the L747S mutation to EGFR. According to some embodiments, the non-small cell lung cancer comprises cells that have the T854A mutation to EGFR. According to some embodiments, the non-small cell lung cancer comprises cells that have amplifications of mesenchymal-epithelial transition factor (MET) receptor tyrosine kinase. According to some embodiments, the non-small cell lung cancer comprises cells that over express the receptor tyrosine kinase AXL and/or its ligand GAS6. According to some embodiments, the non-small cell lung cancer comprises cells that have undergone epithelial-mesenchymal transformation. According to some embodiments, the non-small cell lung cancer comprises cells that have lost expression of MED12. According to some embodiments, the non-small cell lung cancer comprises cells that have a high-level amplification at cytoband 22q11.21. According to some embodiments, the non-small cell lung cancer comprises cells that have overexpression of CRKL. According to some embodiments, the non-small cell lung cancer comprises cells that have a mutation in vascular endothelial growth factor (VEGF). According to some embodiments, the non-small cell lung cancer comprises cells that have a mutation in insulin-like growth factor 1 receptor (IGF-1R). According to some embodiments, the non-small cell lung cancer comprises cells that have a mutation in phosphoinositide-3kinase, catalytic, alpha polypeptide (PIK3CA). According to some embodiments, the non-small cell lung cancer comprises cells that have a mutation in v-RAF murine sarcoma viral oncogene homolog B1 (BRAF). According to some embodiments, the non-small cell lung cancer comprises cells that have a HER2 gene amplication. According to some embodiments, the non-small cell lung cancer comprises cells that have reduced expression of neurofibromin. According to some embodiments, the non-small cell lung cancer comprises cells that have a mutation in a beta-tubulin gene. According to some embodiments, the non-small cell lung cancer comprises cells that have over expression of MDR/ABCB1.

According to some embodiments, pharmaceutical compositions of the described invention are administered to treat a melanoma that has acquired drug resistance. According to some embodiments, the melanoma comprises cells that have a mutation in B-Raf proto-oncogene (BRAF). According to some embodiments, the melanoma comprises cells that have a V600E mutation in BRAF. According to some embodiments, the melanoma comprises cells that have upregulation of platelet derived growth factor receptor b (PDGFRb). According to some embodiments, the melanoma comprises cells that have acquired EGFR expression. According to some embodiments, the melanoma comprises cells that have a mutation to NRAS. According to some embodiments, the melanoma comprises cells that over express BRAF. According to some embodiments, the melanoma comprises cells that have a copy number amplification of the BRAF gene. According to some embodiments, the melanoma comprises cells that have a mutation in the MEK1 or MEK2 genes. According to some embodiments, the melanoma comprises cells that have upregulated forkhead box D3 (FOXD3).

According to some embodiments, the analogue of the described invention is administered to treat a cancer that has intrinsic resistance to one or more anti-cancer compounds.

According to some embodiments, the analogue of the described invention is administered to treat a non-small cell lung cancer (NSCLC) that comprises cells with intrinsic resistance to one or more anti-cancer compounds. According to some embodiments, the NSCLC comprises cells that have a mutation in EGFR. According to some embodiments, the NSCLC comprises cells that have a T790M mutation in EGFR. According to some embodiments, the NSCLC comprises cells that have expression of the Breast Cancer Type 1 susceptibility protein (BRCA1). According to some embodiments, the NSCLC comprises cells that have low proapoptotic protein BIM (BCL2-like 11) expression.

According to some embodiments, the analogue of the described invention is administered to treat melanoma that comprises cells with intrinsic resistance to one or more anti-cancer compounds. According to some embodiments, the melanoma comprises cells that have a P29S mutation in RAC1. According to some embodiments, the melanoma comprises cells that have loss of PTEN expression. According to some embodiments, the melanoma comprises cells that have cyclin D1 over expression. According to some embodiments, the melanoma comprises cells that have a mutation in NFL Sensitivity to Telomerase Inhibitors According to some embodiments, the analogue of the described invention is administered to a patient to treat a cancer or proliferative disorder after cells of the cancer or proliferative disorder have been identified as being sensitive to the analogue. According to some embodiments, cells of the cancer or proliferative disorder are tested for a gene expression profile. According to some embodiments, a gene expression profile is determined by gene expression microarray. According to some embodiments, the cancer or proliferative disorder comprise cells that do not overexpressing one or more of the genes listed in TABLE III. According to some embodiments, the cancer or proliferative disorder comprise cells that do not under express one or more of the genes listed in TABLE IV.

According to some embodiments, the analogue of the described invention is administered to a patient to treat a cancer or proliferative disorder with or after treatment with a sensitizing agent. According to some embodiments, the sensitizing agent is a demethylating agent. According to some embodiments, the sensitizing agent is 5-azacytidine.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Materials and Methods:
Cell Lines

HCT116 represents a human colon cancer cells, A549 models human lung epithelial cancer cells, H2882 models human lung epithelial cancer cells, HCC2429 models human lung epithelial cancer cells, HCC827 models human lung epithelial cancer cells, HCC15 models human lung epithelial cancer cells, H2087 models human lung epithelial cancer cells, HCC4017 models human lung epithelial cancer cells, HCC515 models human lung epithelial cancer cells, H2009 models human lung epithelial cancer cells, BJ-hTERT cells model telomerase expressing normal human fibroblast cells, and BJ human fibroblasts (telomerase silent) were grown in a Media X (Hyclone, Logan, UT) supplemented with 10% cosmic calf serum (Hyclone).

Drug Preparation 6-thio-dG (Metkinen Oy, Kuopio, Finland) was dissolved in DMSO/water (1:2), 6-thio-G (Sigma, St Louis, MO) was dissolved in serum free medium, and GRN163L (Geron Corporation, Menlo Park, Calf.) was dissolved in phosphate buffer saline (PBS) to prepare 50 mM or 10 mM stock solutions, which were frozen at −80° C. After stock solutions were prepared, they were aliquoted into 1 mM solutions, which were further diluted as needed for in vitro treatment experiments.

GRN163L (Imetelstat sodium) is a 13-mer thio-phosphoramidate oligonucleotide with the following sequence: 5'-TAGGGTTAGACAA-3' (SEQ ID NO: 1). Imetelstat has a palmitoyl group at the 5'-end, that helps the oligonucleotide to pass through cell membranes. The compound is complementary to the template region of human telomerase RNA subunit (hTR), and it is a highly potent direct and competitive inhibitor of telomerase. Tumor cell line treatment with imetelstat results in telomerase inhibition and progressive telomere shortening, leading to cell senescence or apoptosis in vitro.

Long-Term Cell Culture Studies

For long-term cellular experiments, HCT116 (1,000 cells/cm$^2$) and BJ (10,000 cells/cm$^2$) cells were fed with 6-thio-dG (1, 3, 10 μM) containing medium every three days. The cells were counted and replated every week for 10-16 weeks. Additionally, HCT116 cells (1,000 cells/cm$^2$) were fed with 6-thio-G (1, 3, 10 μM) every three days and each week cells were counted, collected for TRF (Telomere Restriction Fragment) analysis and replated. HCT116 cells, following treatment with 10 μM 6-thio-dG for 12 weeks, were then treated with a combination of 10 μM 6-thio-dG and 3 μM GRN163L for 2-4 weeks.

Telomerase Activity Assay

Telomerase activity was measured by the TRAP assay (Telomeric Repeat Amplification Protocol as described in Shay J. W. and Bacchetti S., "A survey of telomerase activity in human cancer," European Journal of Cancer 1997; 33:787-91.). Briefly, HCT116 cells were treated with 1 or 10 μM 6-thio-dG for 1-12 weeks. 1×10$^5$ cells were collected and lysed with ice-cold NP-40 lysis buffer (10 mM Tris-HCl pH 8.0, 1.0 mM MgCl2, 1 mM EDTA, 1% NP-40, 0.25 mM sodium deoxycholate, 10% glycerol, 150 mM NaCl, 5 mM β-mercaptoethanol) for 30 min. One microliter cellular lysate for 2500 cells was used for each reaction. Hela cells were used as a positive control and lysis buffer was used as a negative control. Samples were prepared and then the telomerase extension products were amplified using PCR (95° C. for 5 min to inactivate telomerase, then 95° C. for 30 sec, 52° C. for 30 sec, 72° C. for 30 sec; 24 cycles). Samples were run on a 10% non-denaturing acrylamide gel and visualized using a Typhoon PhosphorImager scanner system (Molecular Dynamics, GE Healthcare, Piscataway, NJ) that is capable of reading Cy5 fluorescence.

Telomere Length Assay (TRF, Terminal Restriction Fragment)

1×10$^6$ cells were collected and washed with PBS. DNA was isolated using the manufacturer's instructions (Qiagen, Valencia, CA). 2.5 μg DNA was digested with six different restriction enzymes (HhaI, HinfI, MspI, HaeIII, RsaI, AluI) (New England Bio, Ipswich, MA) and incubated at 37° C. overnight. Digested DNA was separated on a 0.7% agarose gel overnight at 70 V. The terminal restriction fragment (TRF) gel was denatured for 20 min in denaturating solution (0.5 M NaOH, 1.5 M NaCl, pH 13.2) and dried on Whatman 3MM paper under vacuum for 3 hours at 56° C. The gel was neutralized for 15 minutes in neutralization buffer (1.5 M NaCl, 0.5 M Tris-HCl, pH 8.0) and then probed with a radiolabeled telomeric probe (C-rich) for 16 hours at 42° C. in 5×SSC buffer, 5×Denhardt's solution, 10 mmol/L Na$_2$HPO$_4$, and 1 mmol/L Na$_2$H$_2$P$_2$O$_7$. The gel was washed once with 2×SSC, 0.1% SDS, twice with 0.5×SSC, 0.1% SDS and then twice with 0.5×SSC, 1% SDS at room temperature for 15 min. Gels were exposed to a PhosphorImager screen overnight and analyzed using a Typhoon PhosphorImager scanner system (Molecular Dynamics).

Telomere Dysfunction Induced Foci (TIF) Assay

The TIF assay is based on the co-localization detection of DNA damage by an antibody against DNA damage markers such as gamma-H2AX and telomeres by the telomeric protein TRF2. Briefly, HCT116 cells were plated in 4-well chamber slides and after the cells attached to the surface, either 3 μM 6-thio-dG or 3 μM 6-thio-G was added to the medium at different time points (0, 30 min, 12 h, 24 h, 48 h, 72 h). Slides were rinsed once with PBS and fixed in 4% paraformaldehyde in PBS for 10 min. Then, cells were washed twice with PBS and permeabilized in 0.5% Nonidet-P40 in PBS, blocked with 0.5% Bovine Serum Albumin (BSA) and 0.2% fish gelatin in PBS for 30 min. gamma-H2AX (mouse) (Millipore, Billerica, MA) was diluted 1:1000 and TRF2 (rabbit) (Abcam, Cambridge, MA) was diluted 1:200 in blocking solution and this primary Ab mixture was incubated on cells for 2 h. After three washes with PBST (1×PBS in 0.1% Triton) and 3 washes with PBS, cells were incubated with Alexaflour 488 conjugated goat anti rabbit (1:500) (Invitrogen, Grand Island, NY) and Alexaflour 568 conjugated goat anti mouse (1:500) (Invitrogen) for 40 min, then washed six times with PBS. After drying, the slides were mounted with Vectashield mounting medium with DAPI (Vector Laboratories, Burlingame, CA). Images were captured with Deltavision wide-field microscope, then deconvoluted using Autoquant X3. TIFs were quantified using Imaris software.

Statistical Analysis

Comparisons of different groups for statistical significance were analyzed using a two-tailed, unpaired. Student t test. P value of 0.05 or less was considered significant.

Results

Effects of 6-thio-dG and 6-thio-G on Cellular Morphology

Cancer HCT116 and normal BJ fibroblast cells were treated with 6-thio-dG (3 μM) and 6-thio-G (3 μM) twice during one week. Following one week of the treatment, cell morphology was monitored, and then the cells were collected and counted. FIG. 1B shows the results of the cell count. Treatment with 6-thio-dG resulted in death of the vast majority of HCT116 cells, and also changed their morphology, whereas the morphology and cell counts of normal BJ fibroblasts were only slightly affected.

6-thio-dG, but not 6-thio-G, Resulted in Progressive Telomere Shortening in Cancer Cells To determine if 6-thio-dG and 6-thio-G causes progressive telomere shortening, telomere lengths of treated cells were evaluated by TRF assay. Cancer HCT116 and normal BJ fibroblast cells were treated with 1 μM or 10 μM of 6-thio-dG for 1-12 weeks every 3 days. In addition, HCT116 cells were also treated with 1 μM or 10 μM 6-thio-G for 1-10 weeks every 3 days to determine if there is any effect of this molecule on telomeric length maintenance. The control was untreated. Each week samples were collected for TRF analysis at 1×10$^6$ cells/sample at 1, 5, and 12 weeks for cells treated with 6-thio-dG and 1, 5, and 10 for cells treated with 6-thio-G.

The results of the TRF assays showed that telomere shortening was detectable as early as one week and five weeks, with more dramatic telomeres shortening after 12 weeks of continuous 6-thio-dG treatment. At 12 weeks, both the 1 μM or 10 μM showed dramatic telomere shortening. At the same time, treatment with 6-thio-G did not result in any significant effects on telomere length of HCT116 cells after 10 weeks. This suggested that intracellular metabolic pathways of 6-thio-dG and 6-thio-G are different, and that 6-thio-dG is much more readily converted into the corresponding 5'-triphosphate, which is eventually being recognized by telomerase and incorporated into telomeres.

In addition, BJ fibroblast cells treated with 6-thio-dG or 6-thio-G (data not shown) for 10 weeks did not show enhanced telomere shortening, as compared to untreated control cells. When telomerase activity of HCT116 cells treated with 6-thio-dG or 6-thio-G was evaluated by TRAP assay, no inhibition of telomerase activity was observed for either. (For the TRAP assay, cells were treated with 1 and 10 μM 6-thio-dG every 3 days for 12 weeks. Each week samples were collected for TRAP analysis at 1×10$^5$ cells/sample. The control was an untreated sample.) This suggests that 6-thio-dG causes telomeric shortening independent from telomerase inhibition.

6-thio-dG and GRN163L Show Additive Effects on Telomere Shortening

HCT116 cells were treated with either 10 μM 6-thio-dG alone for 12-16 weeks, or with 3 μM GRN163L alone for 11 weeks. Then, these long term 6-thio-dG treated surviving cells were cultured with a combination of 6-thio-dG (10 μM) and/or GRN163L (3 μM) for 2-4 additional weeks. FIG. 2 shows a table summarizing the types of treatment protocols tested. Treatment with GRN163L did not show any significant telomere shortening after 11 weeks as compared to the control. Yet, combination therapy produced additive, if not synergistic, effects on HCT116 cell telomere shortening. Specifically, the HCT116 cells were treated beyond the 12 weeks of 6-thio-dG treatment with either GRN163L only or GRN163L+6-thio-dG, for an additional 2 and 4 weeks to determine if there is an effect on telomere length. These cells cultured with 6-thio-dG beyond 12 weeks of treatment with GRN163L, whether alone or in combination, resulted in increased telomere shortening in HCT116 cells as compared with cells cultured with 6-thio-dG for 12, weeks, 14 weeks, and 16 weeks. These results suggest that combination therapy of 6-thio-dG and GRN163L may be more effective than the single agent therapy with either GRN163L or 6-thio-dG.

Treatment of telomerase positive cancer cells only with 6-thio-dG or only with GRN163L did exhibit telomere shortening, as compared with the telomerase negative control cells. However, HCT116 cells treated with 6-thio-dG for 12 weeks and then continued to be treated with 6-thio-dG exhibited stablized telomeres. In other words, the detected telomere lengths were approximately the same at 12 weeks and 16 weeks. In addition, when cells cultured with 6-thio-dG for 12 weeks were then returned to normal medium without drug for 2-4 weeks, the telomere remained about the same as after 12 week of 6-thio-dG treatment. This suggests that 6-thio-dG treatment does not allow cells to reverse its effects on telomeric lengths for at least 2 to 4 weeks.

Telomerase inhibitors do not immediately cause cell death. By binding to telomerase and inhibiting its enzymatic activity telomerase cannot maintain telomere homeostasis. It can take several months to drive the already short telomeres in cancer cells to become so short that they initiate cell death (apoptosis). Thus, with classic telomerase inhibitors there is a substantial lag phase before cancer cells die. As demonstrated by the present study of GRN163L, there was a delay in telomere shortening for GRN163L as compared to 6-thio-dG. (FIG. 3A (telomerase inhibition) and FIG. 3B (telomere altering (such as uncapping) in telomerase positive cells) show a comparison of this respective lag times in causing cell death.) The 6-thio-dG shortened this lag period considerably since the mechanism of causing apoptosis is to have 6-thio-dG be converted to 6-thio-dGTP in the cells. Such converted compounds are a good and specific substrate for telomerase and can be incorporated into the telomeres. Thus, compounds of the described invention do not inhibit telomerase but are an immediate telomere chain terminator (that is dependent on the presence of telomerase) that will be recognized as damaged DNA and will result in rapid initiation of apoptosis.

6-thio-dG, but not 6-thio-G, Resulted in Telomere Dysfunction Induced Foci (TIFs) in Telomerase Expressing Cells Normal BJ cells and telomere expressing BJ-hTERT cells were seeded in chamber slides. Following cell attachment, 6-thio-dG (10 μM) and 6-thio-G (10 μM) were added to fresh medium of each cell type. To test if 6-thio-dG and 6-thio-G cause telomere dysfunction in normal cells as compared to telomere expressing cells, TIF analysis was conducted. A control was used for each cell type as well, where DMSO was added to fresh medium of each cell type. Using combination of gamma-H2AX and TRF2 immuno-staining we were able to distinguish between genomic DNA damage and telomere specific damage after 48 hours. The results are shown in Table 1. As shown, the 6-thio-dG induced telomere induced foci in BJ-hTERT cells and exhibited more specificity for telomerase expressing cells over normal cells. In comparison, 6-thio-G did not induce telomere induced foci. This demonstrates that only telomerase expressing cells will be affected by 6-thio-dG. These include almost all human cancer cells and certain human diseases involving acute and chronic inflammation.

TABLE 1

| Cell types/ Drug treatment | Number of nuclei scored | >4 TIFs per nucleus background subtracted |
| --- | --- | --- |
| BJ-hTERT/DMSO control | 104 | 0 |
| BJ-hTERT/6-thio-G | 94 | 0 |
| BJ-hTERT/6-thio-dG | 97 | 14 |
| BJ/DMSO control | 102 | 0 |
| BJ/6-thio-G | 101 | 0 |
| BJ/6-thio-dG | 100 | 2 |

6-thio-dG Treatment Results in Telomere Dysfunction in Cancer Cells

Figure 5:
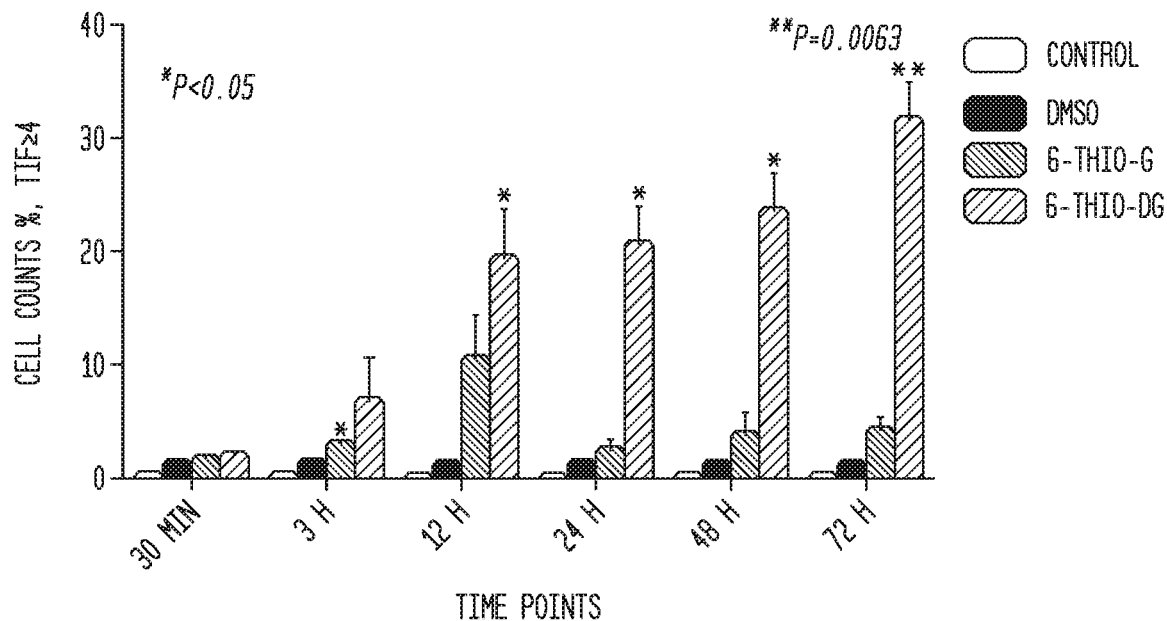
FIG. 5. (A) Binding of gamma-H2AX on uncapped telomeres. 6-thio-dG induced telomeric localization of gamma-H2AX. Representative data. Images were obtained by DeltaVision and then deconvoluted by Autoquant X3. DNA was stained with DAPI (blue). Red dots show DNA damage (gamma-H2AX), green dots show TRF2 and yellow dots show TIFs (telomere dysfunction-induced foci indicating DNA damage on telomeres) in merged images. (B) TIF index (percentage of TIF positive cells) of HCT116 cells treated with 6-thio-dG (3 μM) or 6-thio-G (3 μM). Cells with four or more gamma-H2AX foci co-localizing with TRF2 were scored as TIF positive by Imaris software (n=75, SDs from two independent experiments). *P<0.05, **P=0.0063 (compared with vehicle control), in the unpaired Student t test. ns, not significant differences in the unpaired Student t test. (Control; untreated).

Cancer HCT116 cells were seeded in chamber slides. Following cell attachment, 6-thio-dG (3 μM) and 6-thio-G (3 μM) were added to fresh medium at various time points (0, 30 min, 2 h, 12 h, 24 h, 48 h, 72 h). To test if 6-thio-dG and 6-thio-G cause telomere dysfunction in cancer cells, TIF analysis was conducted. Using combination of gamma-H2AX and TRF2 immuno-staining we were able to distinguish between genomic DNA damage and telomere specific damage. 6-thio-dG treatment causes a 2.8-fold increase in telomeric DNA damage as compared to 6-thio-G after 72 h (FIG. 4). In addition to the increase in telomere damage by 6-thio-dG, there was also an overall increase in genomic DNA damage compared to 6-thio-G (FIG. 5). Co-localization of gamma-H2AX and TRF2 show the existence of dysfunctional telomeres, which can leave chromosome ends uncapped and can induce DNA damage responses, such as cell cycle arrest, senescence, apoptosis and chromosome end fusions.

6-thio-dg Treatment Decreases the Survival and Viability of HCT116 Cells

Figure 6A:
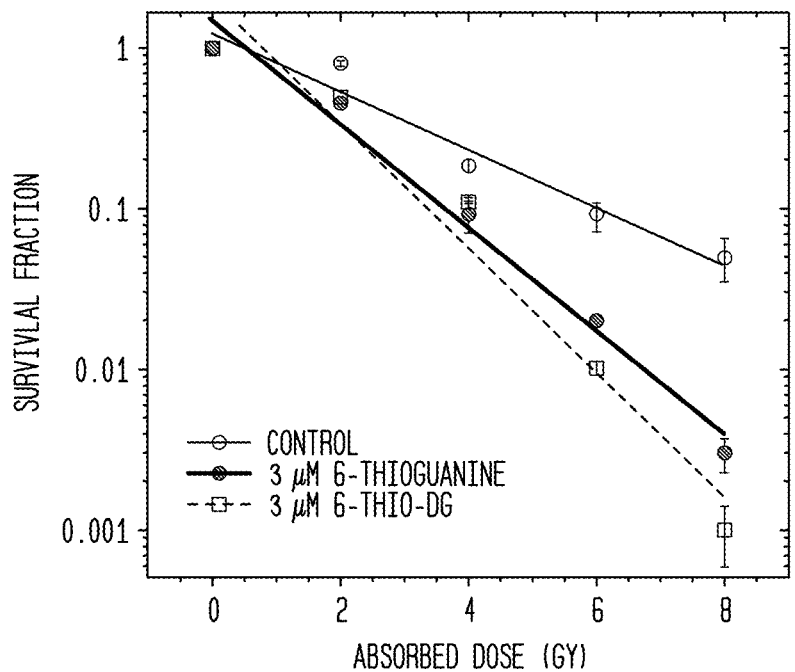
FIGS. 6A and 6B. (A) Line graph showing the survival fraction of HCT116 treated with 6-thio-dG (3 μM) and 6-thio-G (3 μM), and after 72 hours, were irradiated with various doses of ionizing radiation. Following the treatment cells were seeded at different densities and the cultured for 10 days. (B) Line graph showing cell viability determined using a cell titer glow luminescent assay.
Figure 6B:
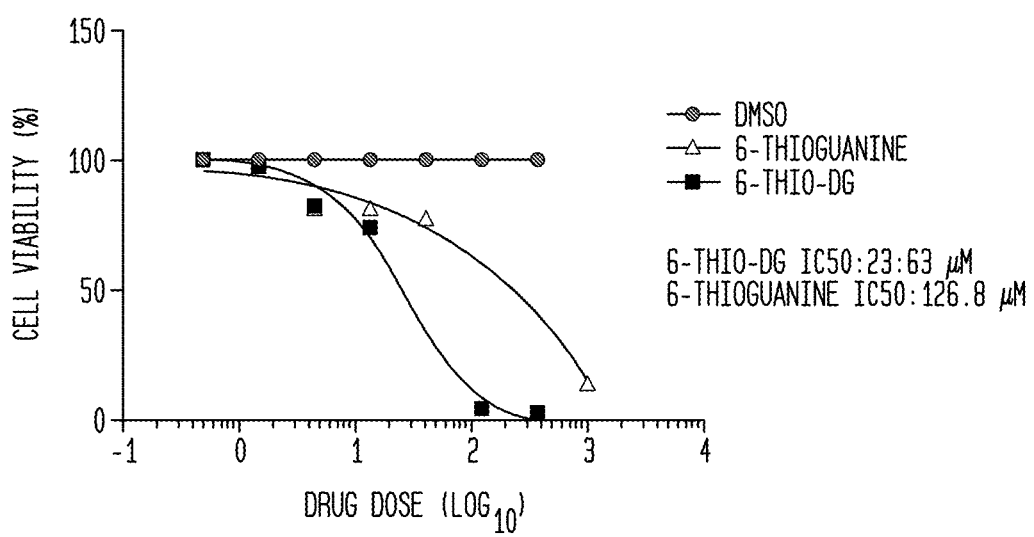

As shown in FIG. 6A, the survival fraction of HCT116 cells treated with 6-thio-dG is lower than cells treated with 6-thio-G. HCT116 cells were treated with 6-thio-dg (3 μM) and 6-thio-G (3 μM), and after 72 hours, were irradiated with various doses of ionizing radiation. Following the treatment cells were seeded at different densities and the cultured for 10 days. As shown in FIG. 6B, cell viability of HCT116 cells treated with 6-thio-dG is lower than cells treated with 6-thio-G. Cell viability was determined using a cell titer glow luminescent assay.

GI 50 Values in a Normal Cell Line and a Panel of Cancel Cell Lines Demonstrate that 6-thio-dG was more Effective at Lower Dosages Against a Variety of Cancer Cell Lines than 6-thio-G Cells of each type listed in Table 2 were seeded in chamber slides. GI 50 values were determined for a panel cancer cell lines and a normal BJ cell line for both 6-thio-dG and 6-thio-G. As shown in Table 2, the GI 50 values were slightly higher for 6-thio-G as compared with 6-thio-dG in all the cancer cell lines except the H2087, where it was equal. Thus, 6-thio-dG was more effective at a lower dosage against a variety of cancer cell lines compared to 6-thio-G. This suggests that 6-thio-dG is a more effective chemotherapeutic agents compared to an already approved compound, 6-thio-G due to an additional mode of action. In xenograft and mouse toxicity studies described in the next section, 6-thio-dG is not only more effective in reducing tumor burden but with less toxicity (e.g. less weight loss).

TABLE 2

| Cell Type | 6-thio-dG (GI 50, μM) | 6-thio-G (GI 50, μM) |
| --- | --- | --- |
| BJ | >100 | >100 |
| HCT116 | 1.0 | 1.2 |
| A549 | 2.1 | 2.3 |
| H2882 | 0.4 | 0.6 |
| HCC2429 | 0.6 | 0.7 |
| HCC827 | 0.8 | 1.7 |
| HCC15 | 0.8 | 1.1 |
| H2087 | 0.9 | 0.9 |
| HCC4017 | 0.9 | 2.0 |
| HCC515 | 2.4 | 4.9 |
| H2009 | 2.6 | 3.3 |

6-thio-dg Treatment Decreases the Rate of Tumor Growth in Xenograft Animal Models with HCT116 and A549 Cells Doses of 2 mg/kg of 6-thio-dG and 2 mg/kg of 6-thio-G were IP injected every two days for a total of 6 injections into mice. DMSO injections were used for the control. The volume of the tumor was measured. FIG. 7A shows that the rate of tumor growth was less for the animal models with HCT116 cells receiving the 6-thio-dG injections.

Figure 7B:
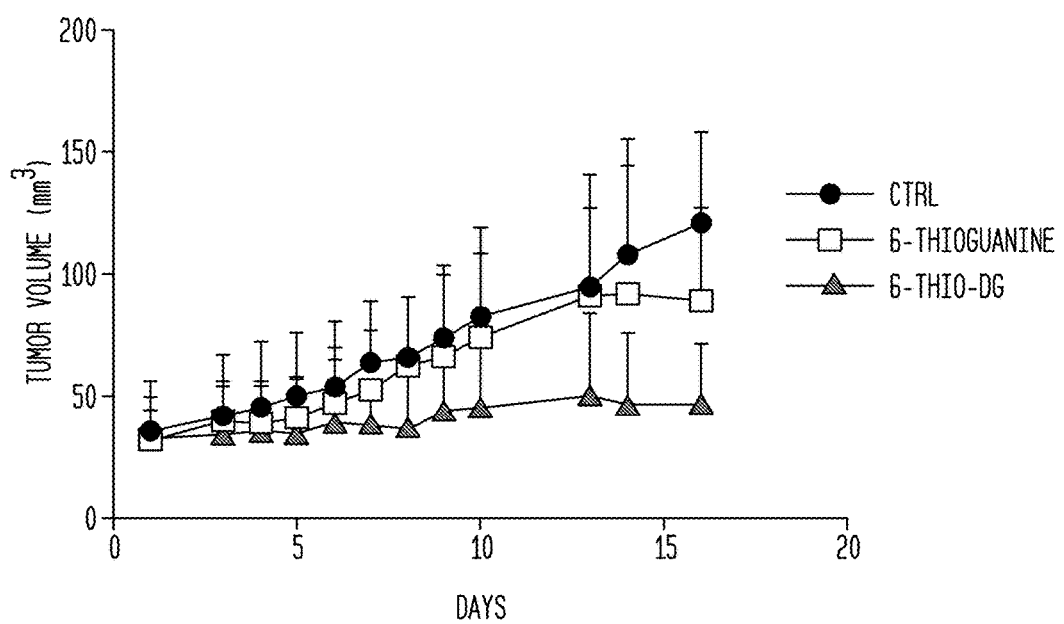

Doses of 2.5 mg/kg of 6-thio-dG and 2.5 mg/kg of 6-thio-G were injected every day into mice after tumor implantation and providing time for tumor initiation. DMSO injections were used for the control. The volume of the tumor was measured. FIG. 7B shows that the rate of tumor growth was less for the animal models with A549 human lung cancer cells receiving the 6-thio-dG injections compared to the control and 6-thio-G treated mice. In addition, upon a histology comparison of the residual tumors, the residual 6-thio-dG tumors were mostly fibrotic and often associated with apoptotic and inflammatory cells, whereas the residual 6-thio-G and control tumors exhibited mostly "healthy" growing cancerous cells.

Toxicity Testing in Rats

Six rats were treated with 15 mg of 6-thio-dG/kg of body weight every two days. One rat died after 6 injections, the remaining five mice showed no signs of impaired function. Another 5 rats were treated with 50 mg of 6-thio-dG/kg of body weight every other day. All rats died after 12 days.

Toxicity-Weight Loss Testing in WT Mice

Figure 8A:
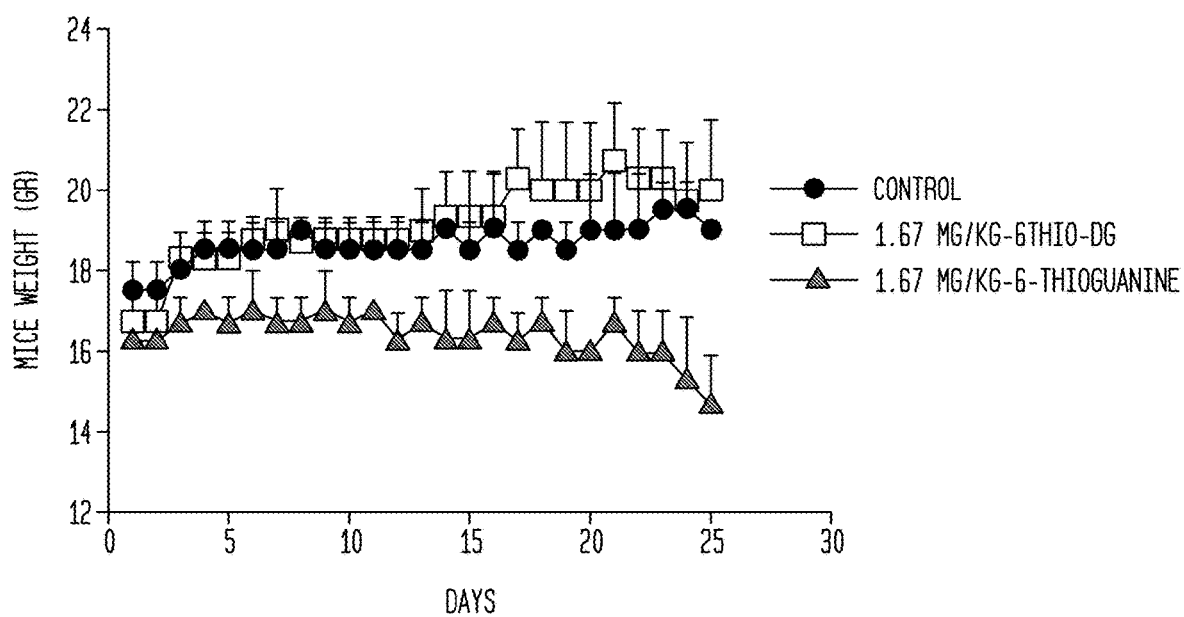
FIGS. 8A and 8B. (A) Line graph showing the weight loss in WT mice models receiving 1.67 mg/kg of 6-thio-dG or 6-thio-G, as compared to a control. (B) Line graph showing the weight loss in WT mice models receiving 5 mg/kg of 6-thio-dG or 6-thio-G, as compared to a control. Graphs show 6-thio-dG causes less weight loss compared to 6-thio-G.
Figure 8B:
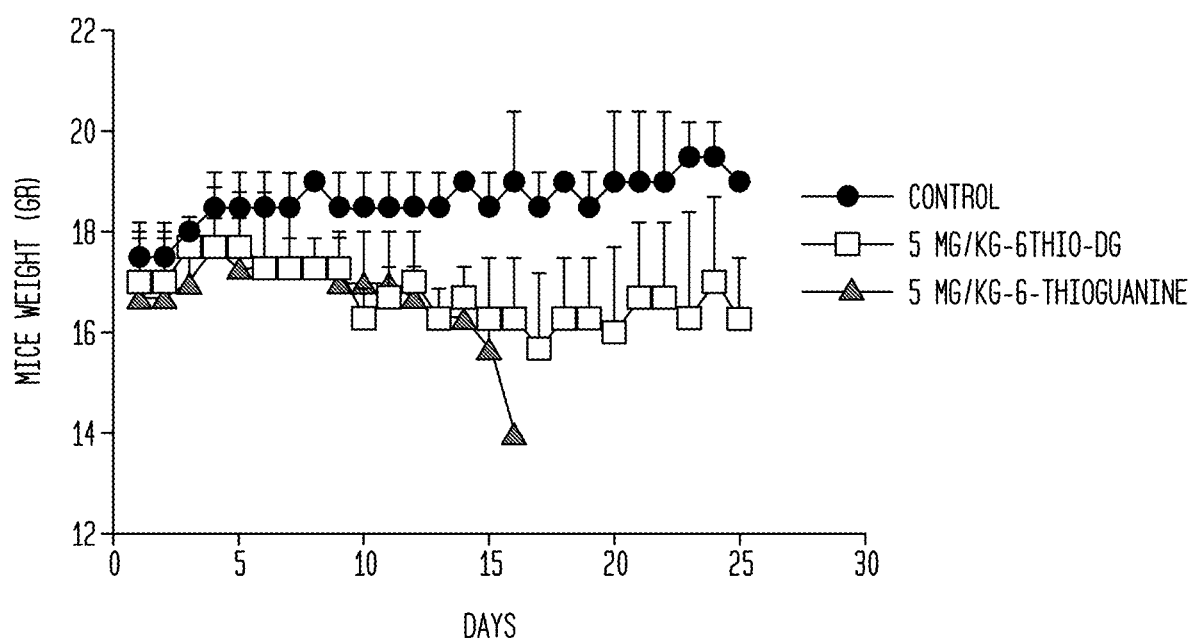

Six WT mice were treated with 1.67 mg of 6-thio-dG/kg of body weight daily. Six WT mice were treated with 1.67 mg of 6-thio-G/kg of body weight daily. Six WT mice were treated with 5 mg of 6-thio-dG/kg of body weight daily. Six WT mice were treated with 5 mg of 6-thio-G/kg of body weight daily. The mice were given the appropriate dosage and weighed daily for 25 days. The results are shown in FIGS. 8A and 8B. For the mice administered the lower 1.67 mg/kg dose, an example of an effective cancer dose, no weight loss was observed for those treated with 6-thio-dG. In comparison, the mice receiving 6-thio-G at the same dose lost between 1-2 grams (6-12% of initial weight) over the course of the 25 day treatment. For the mice administered the higher 5 mg/kg dose (a 2-3 fold increase over an effective cancer dose), only modest weight loss was observed for those treated with 6-thio-dG. In comparison, the mice receiving 6-thio-G at the same dose loss around 2 grams and all mice died by the 15$^{th}$ day of treatment. Importantly, these results in normal mice suggest that expected toxicities associated with treating cancer patients 6-thio-dG are expected to be significantly less compared to the already approved 6-thio-G compound. In addition, there is a significant tumor reduction effect of 6-thio-dG at ~3-fold lower doses that do not cause weight loss in mice.

Most Telomerase-Positive Cancer Cells are Sensitive to 6-thio-dG While Normal Cells are Not Four different cell lines were treated with nine different doses of 6-thio-dG for 7 days. HCT116 colon cancer cell line (FIG. 9A), HCEC1 normal colonic cell line (FIG. 9C), A549 non-small cell lung cancer cell line (FIG. 9B), and BJ normal fibroblast cell line (FIG. 9D) were each treated. Survival fraction was measured by CellTitreGlo luminescent cell viability assay (Promega).

Figure 9:
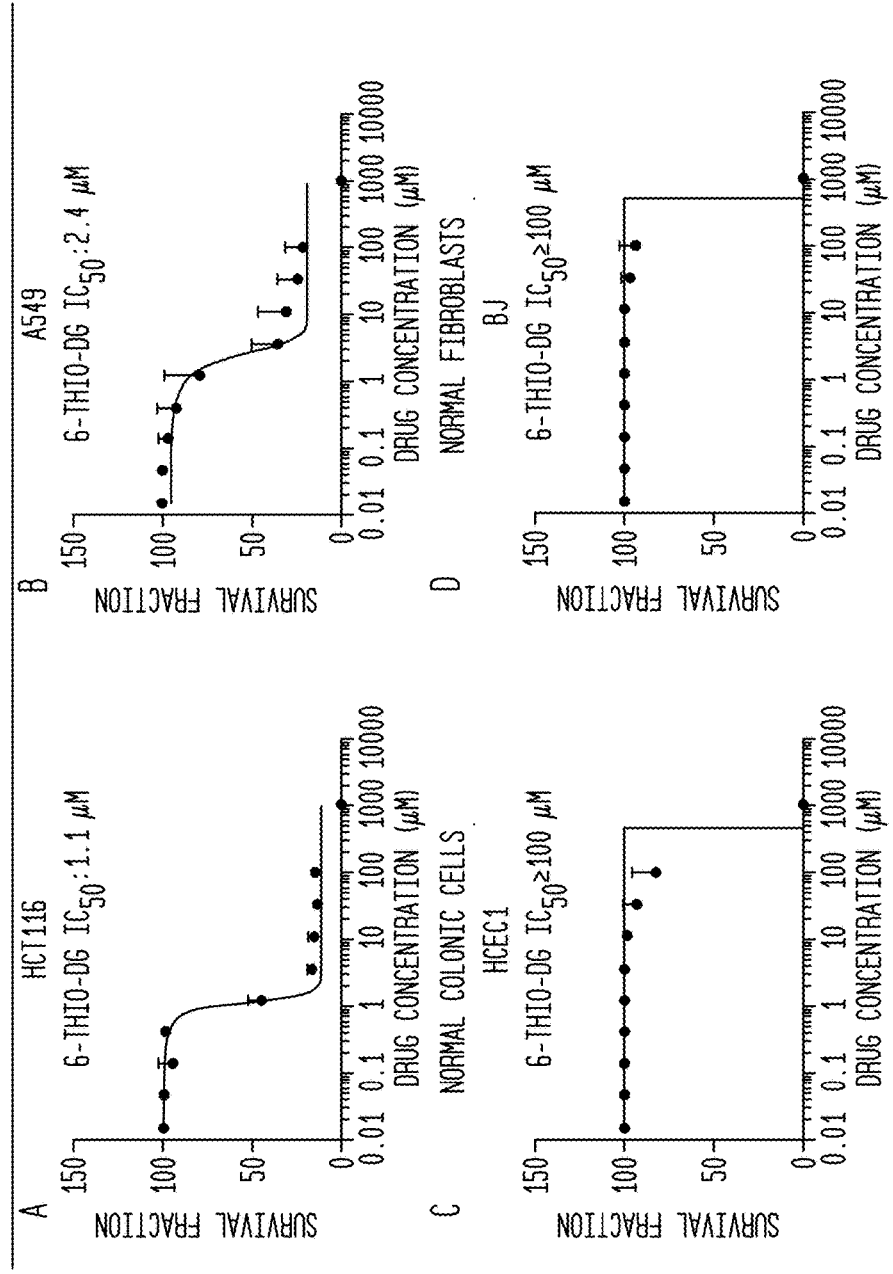
FIG. 9 shows the IC$_{50}$ values of HCT 116 colon (A), A549 non-small cell lung cancer (B), HCEC1 normal human colonic epithelial (C) and BJ normal human fibroblast (D) cells. Cells were treated with nine different doses of 6-thio-dG and evaluated for survival at 7 days. Survival fraction was measured by CellTitreGlo luminescent cell viability assay. Most telomerase-positive cells are sensitive to 6-thio-dG, but normal cells are not.

The results of FIG. 9 show that the cancer cell lines, HCT116 and A549, were more sensitive to 6-thio-dG when compared to their non-cancerous counterpart cell line. While the IC$_{50}$ values for HCT116 and A549 cell lines were determined to be 1.1 µM and 2.4 µM (FIGS. 9A and 9B), respectively, both of the non-cancerous cell lines had IC$_{50}$ values greater than 100 µM (FIGS. 9C and 9D). Notably, HCT116 and A549 are both telomerase positive cancer cell lines while, HCEC1 and BJ are telomerase silent normal cell lines.

Gene Expression Differences of 6-thio-dG Sensitive and Resistant Cell Lines

Gene expression differences were determined between 63 different non-small cell lung cancer cell lines by micro array analysis. Briefly, approximately 5 µg of total cellular RNA was isolated from each cell line and reverse transcribed into cDNA using standard techniques. The cDNA was then indirectly labeled with a fluorescent probe using a two-step hybridization and labeling protocol where the gene chip (Illumina Human WG-6 V3, Cat No: BD101-0201, BD-101-0603) was hybridized to cDNA overnight, washed stringently, and then post-stained with fluorescent dendrimers. After hybridization and washes, the gene chip was scanned using Illumina TotalPrep Kit (Ambion) Cat No: AMIL1791 and then arrays were scanned using Illumina Beadstation 500 BeadArray reader and data acquisitioned with BeadStudio (Illumina) for visualization and data mining. The data is available and processed on GEO (accession GSE32036 http://www.ncbi.nlm.nih.gov/geo/query/acc.cgi?token=pfiphqkackiyubo&acc=GSE32036). Raw data was processed using default parameters of the MBCB package in R/Bioconductor. Statistically significant genes were determined using unpaired t-tests with multiple testing correction via the Bonferroni method (p<0.01).

Figure 10:
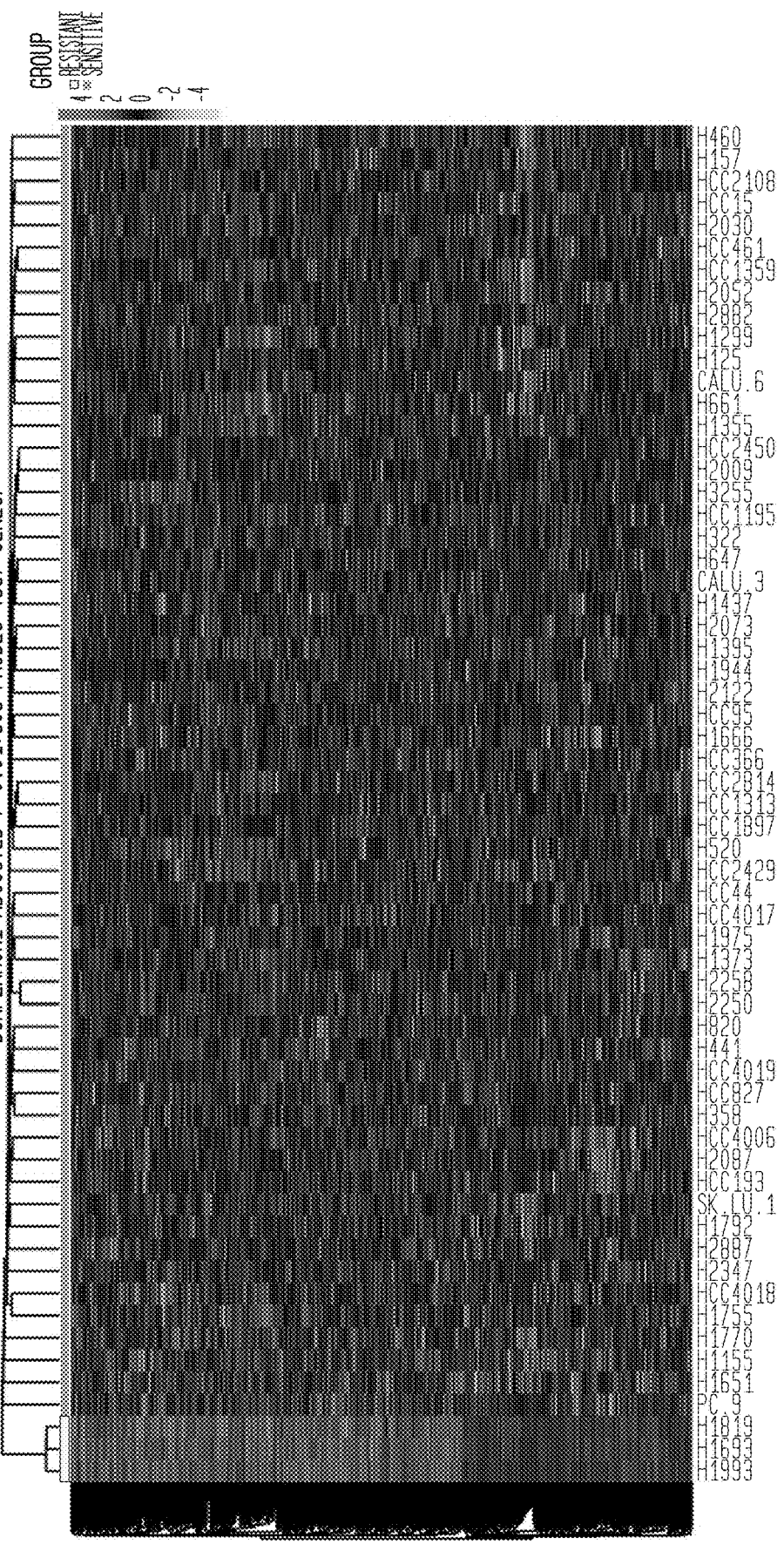
FIG. 10 shows a graphical representation of gene expression differences for 667 genes in 64 different 6-thio-dG resistant and sensitive NSCLC cell lines as determined by gene chip (Illumina WG-6 V3, Cat. No. BD101-0201, BD-101-0603). The hybridized chip was scanned using Illumina TotalPrep Kit (Ambion) Cat. No. AMIL1791 and Illumina Beadstation 500 Bead Array reader. Data acquisition for visualization and data mining was performed with BeadStudio (Illumina). Genes were identified having a greater than 0.01 cutoff using unpaired t-test with multiple testing corrections via Bonferroni method. Only 3 cell lines were resistant to 6-tho-dG (FIG. 10 left side).
Figure 11B:
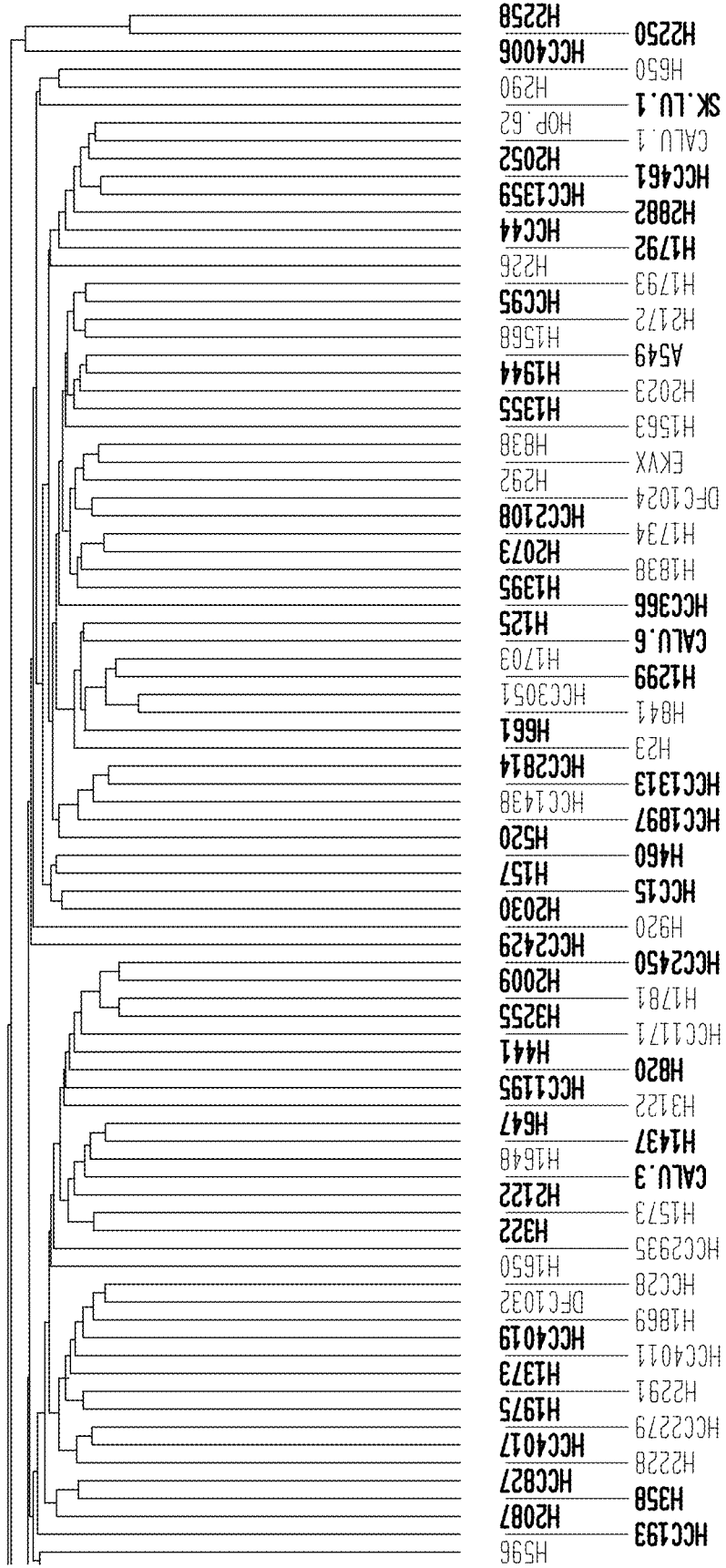

667 genes were identified as having greater than 0.01 cutoff using unpaired t-tests with multiple testing correction via the Bonferroni method. A heat map graphical representation of the data is depicted in FIG. 10. The three NSCLC cell lines that were known to be resistant to 6-thio-dG were grouped as indicated in FIG. 10 (labeled "resistant"). Sensitive cell lines and cell lines untested for 6-thio-dG sensitivity are also noted. Other cell lines tested were predicted to be fully or partially resistant to 6-thio-dG based on their microarray signature (not shown in FIG. 10). Those cell lines were the H2086, H324, H2342, and H2126 NSCLC cell lines, which had gene expression profiles that clustered with known resistant NSCLC cell lines, H1993, H1693 and H1819 (FIG. 11).

Of the four predicted resistant cell lines, one was experimentally demonstrated to be resistant to 6-thio-dG while the others were demonstrated to have intermediate resistance (FIG. 12). A panel of NSCLC cell lines was tested for sensitivity to 6-thio-dG by performing a cell count after 1 week treatment. Briefly, cells were treated with 3 µM 6-thio-dG every three days for 1 week. Viable cells were counted at the end of treatment. Each 6-thiodG treated cell line was normalized to its DMSO treated control. The results of the cell count are depicted in FIG. 12, with the various cell lines arranged in descending resistance to 6-thio-dG from left to right. The data shows that four cell lines (H1693, H1993, H2086, H1819) had a survival rate of greater than 50%, and therefore were classified as resistant. The other predicted resistant cell line was classified as having intermediate resistance, with IC$_{50}$ values of 3-7 µM for H2085, H2343, and H2126, and IC$_{50}$ value of 2.2 µM for H324. The IC$_{50}$ values for the whole panel of tested cells are depicted in FIG. 13. The IC$_{50}$ values for tested cells are depicted as a column scatter graph in FIG. 14.

Figure 15:
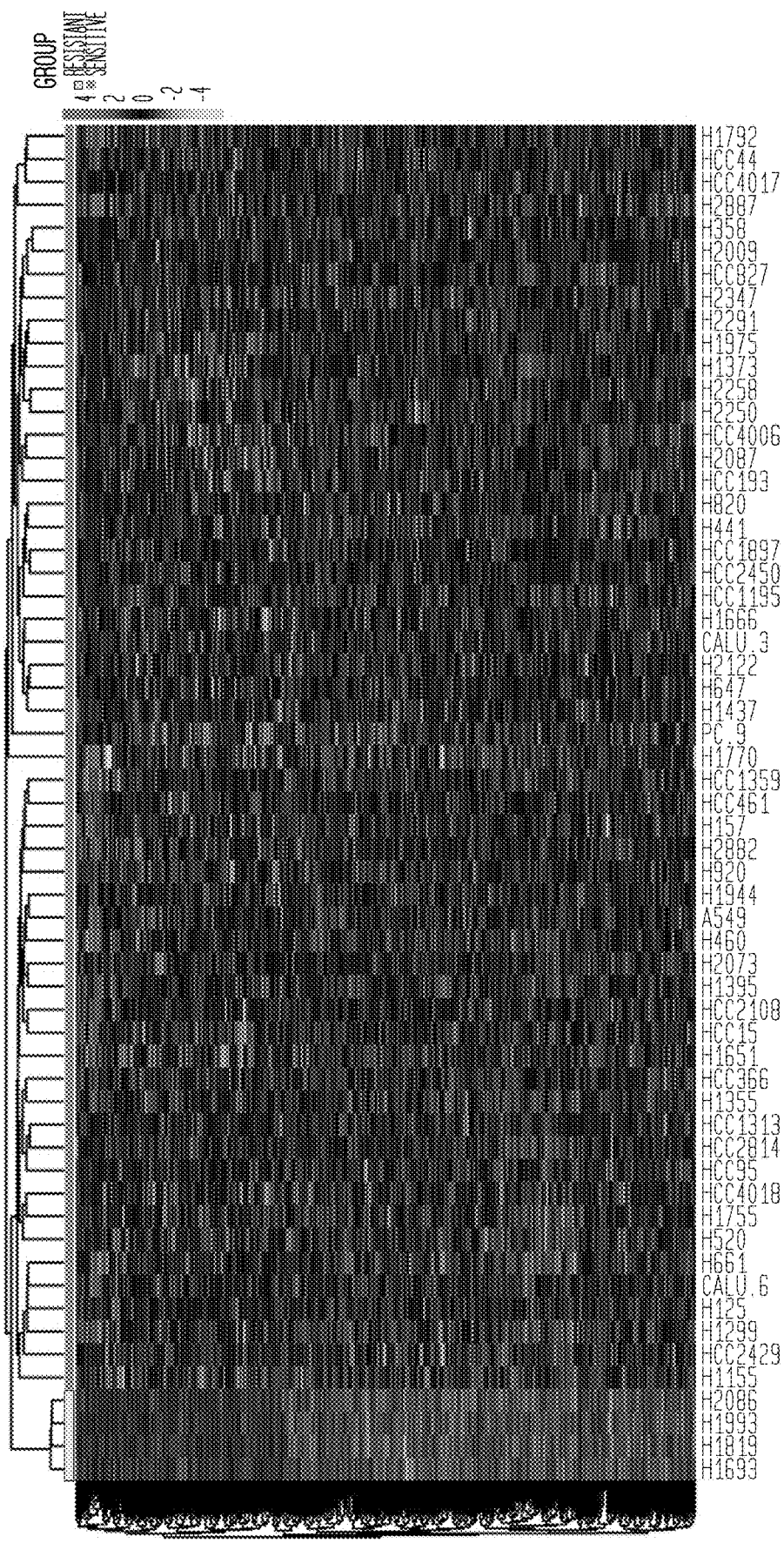
FIG. 15 shows the revised graphical representation of gene expression patterns for 354 genes in 64 different NSCLC cell lines as determined by gene chip after grouping the gene expression profiles of cell lines determined to be resistant to 6-thio-dG. The genes identified as highly upregulated are depicted in table III, infra. The genes identified as highly down regulated are listed in table IV, infra.

A revised cluster analysis of the microarray data was performed by grouping the cell line gene expression profiles of cell lines previously identified as being resistant to 6-thio-dG with the gene expression profile of the newly identified resistant cell line (H2086). The heat map graphical representation of the cluster analysis is depicted in FIG. 15. The revised cluster analysis improved separation of the 6-thio-dG resistant NSCLC cell lines from the sensitive NSCLC cell lines. The genes identified as highly upregulated in 6-thio-dG resistant cell lines are depicted in Table III. The genes highly down regulated in 6-thio-dG resistant cell lines are depicted in Table IV. According to some embodiments, differentially expressed genes and their fold changes were obtained using the Model-based Background Correction for BeadArrays (MBCB) method. According to some embodiments, bead-level data were processed with the MBCB algorithm (See Ding et al, Nucl Acids Res, 36:e58, 2008, which is incorporated by reference in its entirety), which is a background-correction and summarization method. The fold change is the change in the sensitive lines compared to the resistant lines (e.g. the gene corresponding to probe (ILMN_1744604) was expressed ~58 fold higher in the sensitive lines compared to the resistant lines).

TABLE III

| ProdeID | Symbol | Bonferonni Adjusted p-value | FoldChange |
|---|---|---|---|
| ILMN_1744604 | CYBA | 0 | 58.08277 |
| ILMN_2058782 | IFI27 | 5.70E−07 | 20.34844 |
| ILMN_1709795 | RAC2 | 0 | 16.32618 |
| ILMN_1692223 | LCN2 | 1.85E−06 | 15.19393 |
| ILMN_1782419 | GNG11 | 0 | 15.00554 |
| ILMN_1697409 | TNFRSF14 | 0 | 14.95143 |
| ILMN_1746517 | KYNU | 6.91E−07 | 13.64798 |
| ILMN_1738742 | PLAT | 0 | 13.34254 |
| ILMN_1710937 | IFI16 | 0 | 13.23784 |
| ILMN_1723480 | BST2 | 0 | 12.16215 |

TABLE III-continued

| ProdeID | Symbol | Bonferonni Adjusted p-value | FoldChange |
|---|---|---|---|
| ILMN_1724533 | LY96 | 0 | 11.477 |
| ILMN_2201580 | GSTM2 | 1.11E−08 | 11.09314 |
| ILMN_1662358 | MX1 | 5.19E−07 | 8.86166 |
| ILMN_1737514 | KYNU | 1.90E−07 | 8.788725 |
| ILMN_1773963 | GNA15 | 3.74E−05 | 8.246977 |
| ILMN_1801245 | HTM1 | 8.83E−08 | 7.893543 |
| ILMN_1731044 | KCTD14 | 0 | 7.837138 |
| ILMN_1727689 | TNFAIP2 | 8.19E−09 | 7.645218 |
| ILMN_1665865 | IGFBP4 | 0 | 7.468344 |
| ILMN_1699651 | IL6 | 4.89E−06 | 7.042823 |
| ILMN_1755974 | ALDOC | 0.007951 | 6.640219 |
| ILMN_1750062 | IFI44 | 0.000117 | 6.542693 |
| ILMN_1717262 | PROCR | 0 | 6.37652 |
| ILMN_1774287 | CF8 | 5.02E−06 | 6.357424 |
| ILMN_1705247 | ACSL5 | 8.02E−05 | 6.228333 |
| ILMN_1674063 | OA52 | 2.04E−06 | 6.226424 |
| ILMN_2305225 | NDRG4 | 1.08E−11 | 6.066504 |
| ILMN_1701789 | IFIT3 | 1.60E−06 | 6.052289 |
| ILMN_1748840 | CALB2 | 0.000214 | 5.99448 |
| ILMN_1676213 | SRPX2 | 3.29E−05 | 5.87135 |
| ILMN_1698765 | PYCARD | 1.90E−09 | 5.75489 |
| ILMN_1736567 | CD74 | 0.0003 | 5.602897 |
| ILMN_2330307 | SLC43A3 | 2.17E−11 | 5.472617 |
| ILMN_1769245 | GLIPE1 | 4.19E−05 | 5.381182 |
| ILMN_2379644 | CD74 | 5.22E−05 | 5.348715 |
| ILMN_1695311 | HLA-DMA | 1.07E−05 | 5.289018 |
| ILMN_1719883 | CYP4F11 | 5.58E−06 | 5.267559 |
| ILMN_1713813 | LOC650611 | 1.94E−05 | 4.986205 |
| ILMN_1846306 |  | 9.96E−06 | 4.818026 |
| ILMN_2391861 | GSTM1 | 3.27E−06 | 4.506177 |
| ILMN_1689456 | ZBTB20 | 1.04E−06 | 4.487894 |
| ILMN_1738589 | MGLL | 0.00024 | 4.485202 |
| ILMN_2192072 | MMP7 | 0.001719 | 4.479347 |
| ILMN_1744381 | SERPINE1 | 0.000146 | 4.462719 |
| ILMN_1794612 | UBE1L | 1.18E−08 | 4.429826 |
| ILMN_1666078 | HLA-H | 5.71E−09 | 4.365754 |
| ILMN_1681301 | AIM2 | 1.53E−07 | 4.125413 |
| ILMN_2064725 | METTL7B | 4.77E−10 | 4.079261 |
| ILMN_1812618 | CENTD3 | 3.69E−06 | 4.047413 |
| ILMN_1701114 | G6P1 | 2.08E−05 | 4.03626 |

TABLE IV

| | | | |
|---|---|---|---|
| ILMN_2043079 | ILDR1 | 4.37E−06 | −3.03285 |
| ILMN_1630937 | HIST1H2BC | 1.01E−07 | −3.06238 |
| ILMN_1669557 | LOC647881 | 0 | −3.06344 |
| ILMN_1662839 | PLEKHA1 | 0.00584 | −3.23505 |
| ILMN_1651496 | HIST1H2BD | 2.48E−08 | −3.31379 |
| ILMN_1711124 | MARVELD2 | 1.19E−09 | −3.38481 |
| ILMN_2050145 | GRHL2 | 2.60E−05 | −3.39634 |
| ILMN_1801476 | CDS1 | 2.38E−05 | −3.72706 |
| ILMN_1660727 | ENPP5 | 0.005589 | −3.7914 |
| ILMN_1800739 | SPINT2 | 0.004735 | −4.06748 |
| ILMN_1670130 | ARID3A | 0.000976 | −4.06862 |
| ILMN_2130525 | TSPAN13 | 0 | −4.11487 |
| ILMN_1728298 | SBK1 | 5.31E−10 | −4.1275 |
| ILMN_2095704 | SYCP2 | 1.49E−06 | −4.16981 |
| ILMN_1682599 | GPRC5A | 1.00E−05 | −4.20682 |
| ILMN_2041222 | FLJ40504 | 0.000144 | −4.22531 |
| ILMN_1724832 | OVOL2 | 0.003103 | −5.41435 |
| ILMN_1682428 | C1orf59 | 5.40E−06 | −5.57065 |
| ILMN_1770616 | LOC115749 | 0.007205 | −6.36777 |
| ILMN_1737972 | TSPYL5 | 2.48E−08 | −7.14085 |
| ILMN_1700268 | QPRT | 0.000324 | −7.2052 |
| ILMN_1791825 | RAB25 | 0.000272 | −7.47771 |
| ILMN_1801697 | FLJ36445 | 0 | −9.95077 |

TABLE IV-continued

| | | | |
|---|---|---|---|
| ILMN_1796461 | PRSS8 | 0 | −12.4814 |
| ILMN_1687947 | HIST1H2BE | 6.46E−08 | −2.01029 |
| ILMN_1669015 | XPNPEP1 | 0.004845 | −2.01378 |
| ILMN_1775448 | PFN2 | 0.000353 | −2.0138 |
| ILMN_1773935 | TPARL | 0.000218 | −2.0513 |
| ILMN_2372403 | ALDH5A1 | 0.000348 | −2.1106 |
| ILMN_2052717 | GRAMD1C | 0 | −2.12324 |
| ILMN_1739397 | GLMN | 0.000436 | −2.13408 |
| ILMN_1665982 | FTS | 0 | −2.1559 |
| ILMN_1869087 |  | 1.22E−08 | −2.19554 |
| ILMN_2380163 | PTPRF | 0.009202 | −2.21019 |
| ILMN_1813801 | LOC643674 | 2.03E−07 | −2.26958 |
| ILMN_1704196 | DSG2 | 0.009452 | −2.33547 |
| ILMN_1737715 | O5R2 | 1.74E−07 | −2.33774 |
| ILMN_1750158 | ACOX1 | 7.61E−06 | −2.3519 |
| ILMN_1718712 | C20orf177 | 0.001427 | −2.37256 |
| ILMN_1807492 | LOC649426 | 0 | −2.38591 |
| ILMN_1755909 | C20orf1 | 0 | −2.41072 |
| ILMN_1634778 | KRT18 | 0.000445 | −2.4281 |
| ILMN_2229214 | STOX1 | 5.12E−08 | −2.45008 |
| ILMN_1716616 | MARVELD3 | 1.21E−05 | −2.46396 |
| ILMN_1756849 | HIST1H2AE | 8.79E−05 | −2.49756 |
| ILMN_1654014 | STOX1 | 7.31E−08 | −2.72688 |
| ILMN_1690454 | TMEM20 | 0.003809 | −2.73339 |
| ILMN_1755201 | FBXO15 | 0.004784 | −2.79645 |
| ILMN_2047599 | TMEM50B | 2.17E−11 | −2.87009 |
| ILMN_2367458 | UFD1L | 0 | −2.88501 |
| ILMN_1758623 | HIST1H2SD | 0.003996 | −2.99544 |
| ILMN_1754500 | FNBP1L | 1.08E−11 | −2.9958 |

Paclitaxel-Carboplatin Resistant NSCLC Cell Lines are Sensitive to 6-thio-dG

Cell lines that have acquired resistance to standard anticancer compounds were tested for sensitivity to 6-thio-dG. Briefly, cell lines that are normally sensitive to paclitaxel/carboplatin were treated with paclitaxel/carboplatin combination given in a clinically relevant 2:3 ratio over long-term passage in culture to develop resistant cell lines. The NSCLC cell lines chosen were H1299 and H1355, and were treated with paclitaxel/carboplatin double therapy for 8-9 months with incrementally increased doses. Treatment was given in cycles of drug ON/drug OFF and cells were characterized at 18 and 16 different treatment cycles for H1299 and H1355 cells, respectively. T[n] indicates cell line variant developed after 'n' cycles of doublet therapy. The resistance of the cell lines to paclitaxel/carboplatin treatment is depicted in FIG. 16A and FIG. 16B. The resistant H1299 cell line had an $IC_{50}$ value about ten times great than the parental H1299 cell line (FIG. 16A). Similarly, the resistant H1355 cell line had an $IC_{50}$ value about 100 times greater than the H1355 parental cell line (FIG. 16B).

Once paclitaxel/carboplatin resistance was acquired, the resistant H1299 and H1355 cell lines were treated every three days with three different concentrations (1 µM, 3 µM, and 10 µM) of 6-thio-dG or a control (DMSO:water with 1:1 dilution) for one week. A cell count was performed to measure cell growth/death. As depicted in FIG. 16C and FIG. 16D, both of the paclitaxel/carboplatin resistant cell lines were sensitive to all three concentrations of 6-thio-dG when compared to control treatment.

6-thio-dG Sensitivity does not Correlate with Cell Growth Rate or Telomere Length To determine whether a correlation exists between 6-thio-dG sensitivity and cell growth rate, doubling time data for several different cell lines(A549, Calu-3, Calu-6, H1155, H1355, H1395, H1437, H157, H1666, H1693, H1792, H1819, H1838, H1944, H1993, H2009, H2073, H2087, H2122, H2126, H2347, H2882, H2887, H3122, H322, H3255, H358, H460, H661, H727, HCC1359, HCC193, HCC2429, HCC44, HCC515, HCC827, HCC95) was plotted against each cell lines' $IC_{50}$ values (FIG. 17A). The results show no correlation between doubling time and $IC_{50}$ values, indicating that the cell lines which divide more rapidly are no more or less sensitive to 6-thio-dG than cell lines which divide more slowly (FIG. 17A).

Telomere length was also measured to identify whether that variable affects 6-thio-dG sensitivity. Telomere length of several different cell lines (A549, Calu-3, Calu-6, H1155, H1355, H1395, H1437, H157, H1666, H1693, H1792, H1819, H1838, H1944, H1993, H2009, H2073, H2087, H2122, H2126, H2347, H2882, H2887, H3122, H322, H3255, H358, H460, H661, H727, HCC1359, HCC193, HCC2429, HCC44, HCC515, HCC827, HCC95) was plotted against each cell lines' $IC_{50}$ values. Average telomere length was measured by TRF (Telomere Restriction Fragment) via Southern blot. The results show no correlation between telomere length and 6-thio-dG $IC_{50}$ values, suggesting that sensitivity to 6-thio-dG is independent of telomere length (FIG. 17B).

Genetic Mutations of 6-thio-dG Resistant Cell Lines

Figure 18:
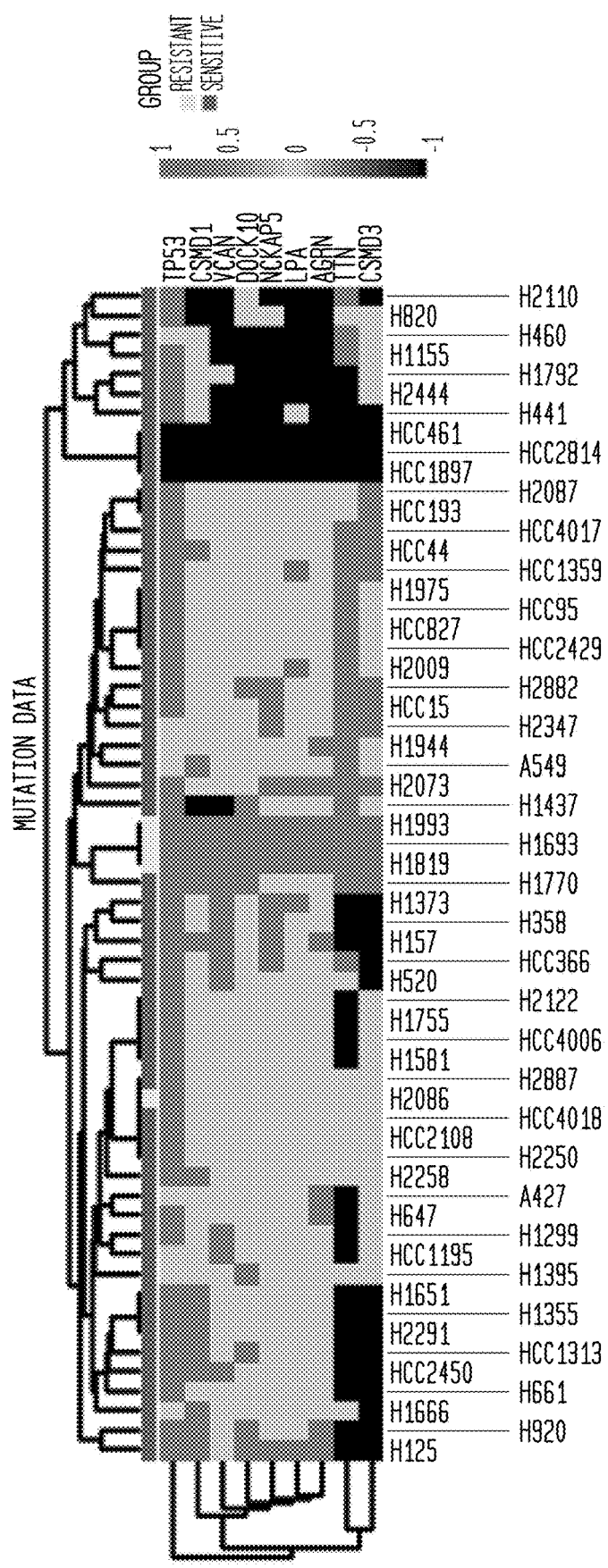
FIG. 18 shows a graphical representation of mutant genes present in various NSCLC cell lines, grouped by genotype of three known resistant NSCLC cell lines. Mutation data was determined from exome sequencing and COSMIC. There were 9 common mutations in 3 of the resistant lines. The mutated genes common to the resistant cell lines H1819, H1693, and H1993 were used to cluster mutant/wild type genes of the NSCLC cell line panel. Genes found to contain mutations among all three resistant cell lines are listed in Table V.

Mutations data was provided from data aggregated from exome sequencing and COSMIC. There were 9 common mutations in 3 of the resistant lines. H2086 did not have mutations data available on 8 of those genes The mutated genes common to the resistant cell lines H1819, H1693, and H1993 were used to cluster mutant/wildtype genes of a panel of NSCLC cell lines (FIG. 18). The genes found to contain mutations among all three resistant cell lines are listed in Table V.

TABLE V

| Gene Name | Description |
| --- | --- |
| TP53 | Tumor suppressor gene that is responsible for making p53 protein |
| CSMD1 | CUB and Sushi multiple domain 1; deletion/mutation in this gene is correlated with more aggressive NSCLC. |
| VCAN | A member of proteoglycan family and a major component of the extracellular matrix; this protein is involved in cell adhesion, proliferation, migrations, and angiogenesis. |
| DOCK10 | A member of cytokinesis protein family; a member of the RhoGTPase family |
| NCKAP5 | A protein coding gene |
| LPA (Lysophosphatidic acid) | Is an intermediate in the synthesis of phosphatidic acid; is involved in cell migration, proliferation, and differentiation; is involved in cell survival |
| AGRN | Is critical in the development of the neuromuscular junction |
| TTN (titin) | Is associated with cancer |
| CSMD3 | Cub and Sushi Multiple Domain 3; associated with colorectal cancer; loss of CSMD3 results in increased proliferation of airway epithelial cells |

Methylation Patterns of 6-thio-dG Sensitive and Resistant NSCLC Cell Lines

Figure 19A:
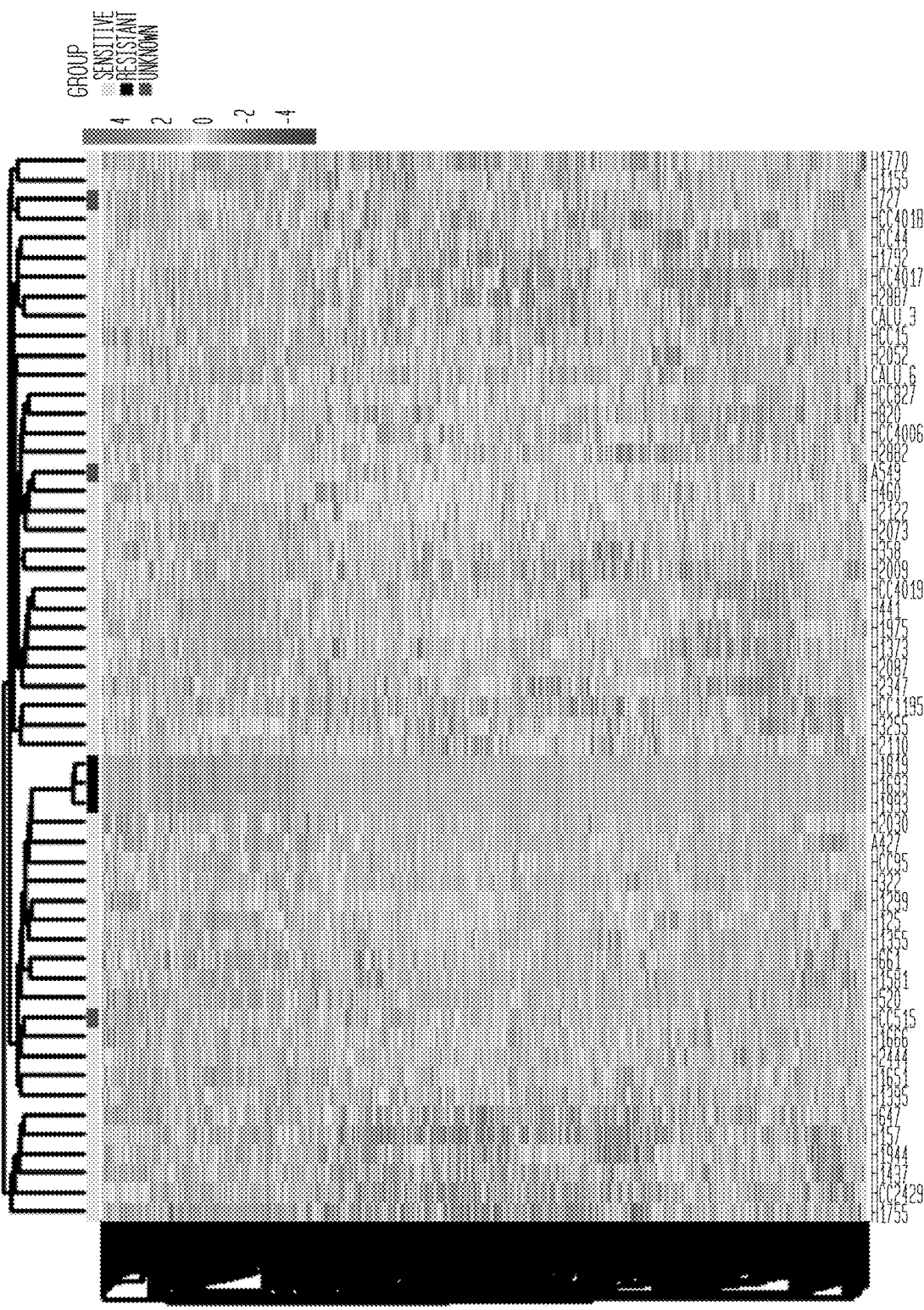
FIG. 19A and FIG. 19B show a graphical representation of methylation patterns across genes of various NSCLC cell lines compared to microarray expression patterns. Methylation data was obtained using the Infinium Human Methylation 450 Bead Chip from Ilumina. Significant methylation sites were determined using t-tests with Bonferroni correction ($p<0.01$).
Figure 19B:
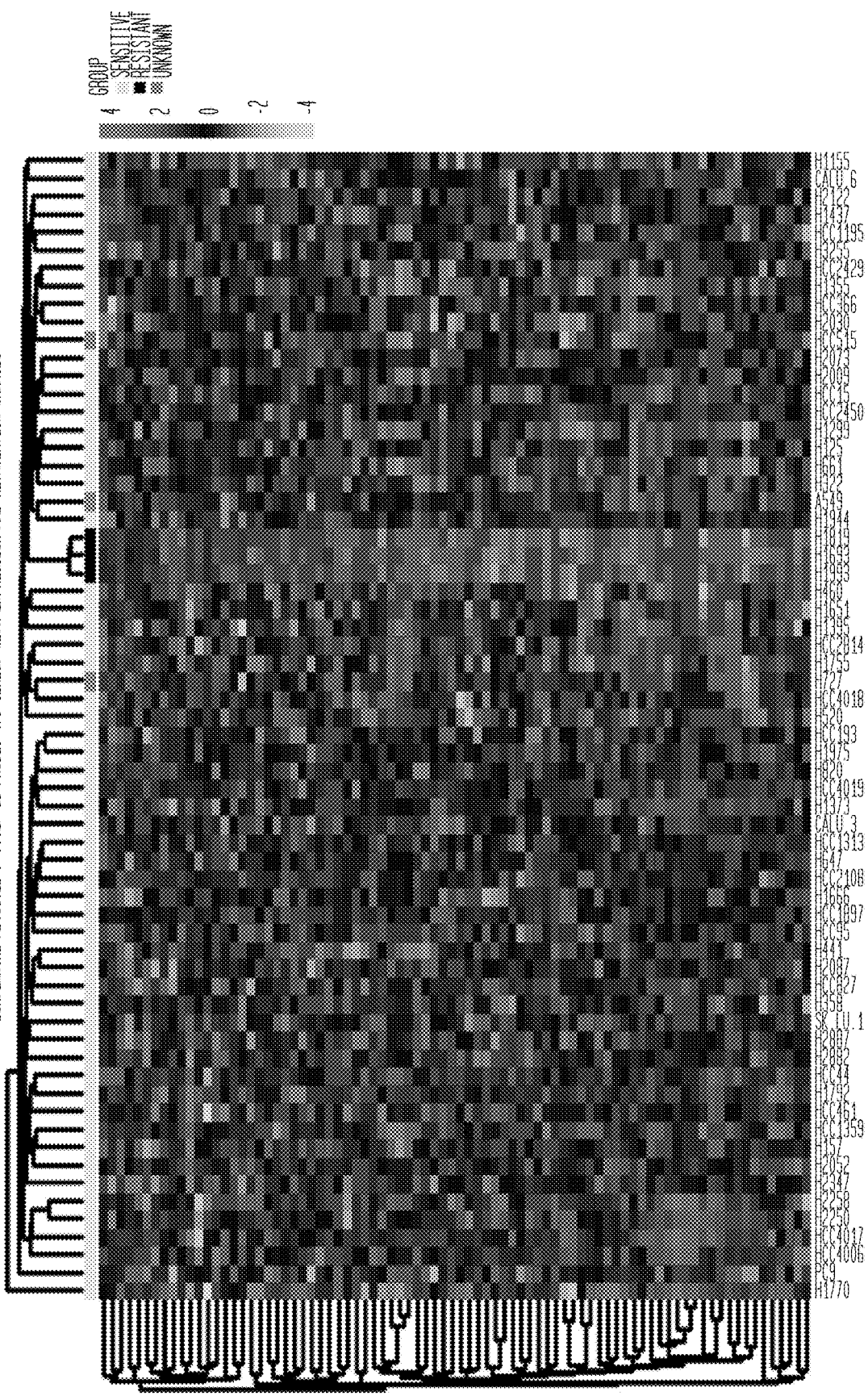

FIGS. 19A and 19B shows Methylation data was obtained using the Infinium HumanMethylation450 BeadChip from Illumina. Significant methylation sites were determined using t-tests with Bonferroni correction (p<0.01).

Sensitization of NSCLC Cells to 6-thio-dG Treatment

Two isogenic pairs of NSCLC cell lines were studied for sensitization to 6-thio-dG treatment. The isogenic pair of cell lines H1693 and H1819, which are derived from the same patient, both are have a resistance to 6-thio-dG treatment ($IC_{50}$ values of >100 μM for both H1693 and H1819). From the isogenic pair of cell lines H1993 and H2073, which are also derived from the same patient, only H1993 displays resistance to 6-thio-dG ($IC_{50}$>100 μM), while H2073 is sensitive ($IC_{50}$>0.7 μM).

All three resistant cell lines were pre-treated with 500 nM of the demethylating agent 5-azacytidine for one week. Following the 5-azacytidine pretreatment, each resistant cell line was treated with 9 different concentrations (0.01 to 1000 micromolar) of 6-thio-dG for one week. Cells were then evaluation for growth/death. The 5-azacytidine pretreatment had no effect on the sensitivity to 6-thi-dG for the H1693 and H1819 isogenic cell lines. But the 5-azacytidine pretreatment did increase sensitivity of the H1993 cells substantially ($IC_{50}$~4.1 μM) (FIG. 20A).

H1993 cells were further studied for sensitivity to 6-thio-dG with the demethylase inhibitor, JumonjiC (FIG. 20B). H1993 6-thio-dG resistant cell lines were treated with 10, 50, and 100 nM JumonjiC (JIB-04) simultaneously with 0, 3, or 5 μM 6-thio-dG for 5 days. Cell counts were performed at the end of treatment. The combination of 6-thiodG and JIB-04 inhibitors had an additive effect on the growth inhibition on H1993 cell line with increasing dosing of these inhibitors.

Acquired and Intrinsic Resistance to 6-thio-dG in NSCLC Cells

Figure 21:
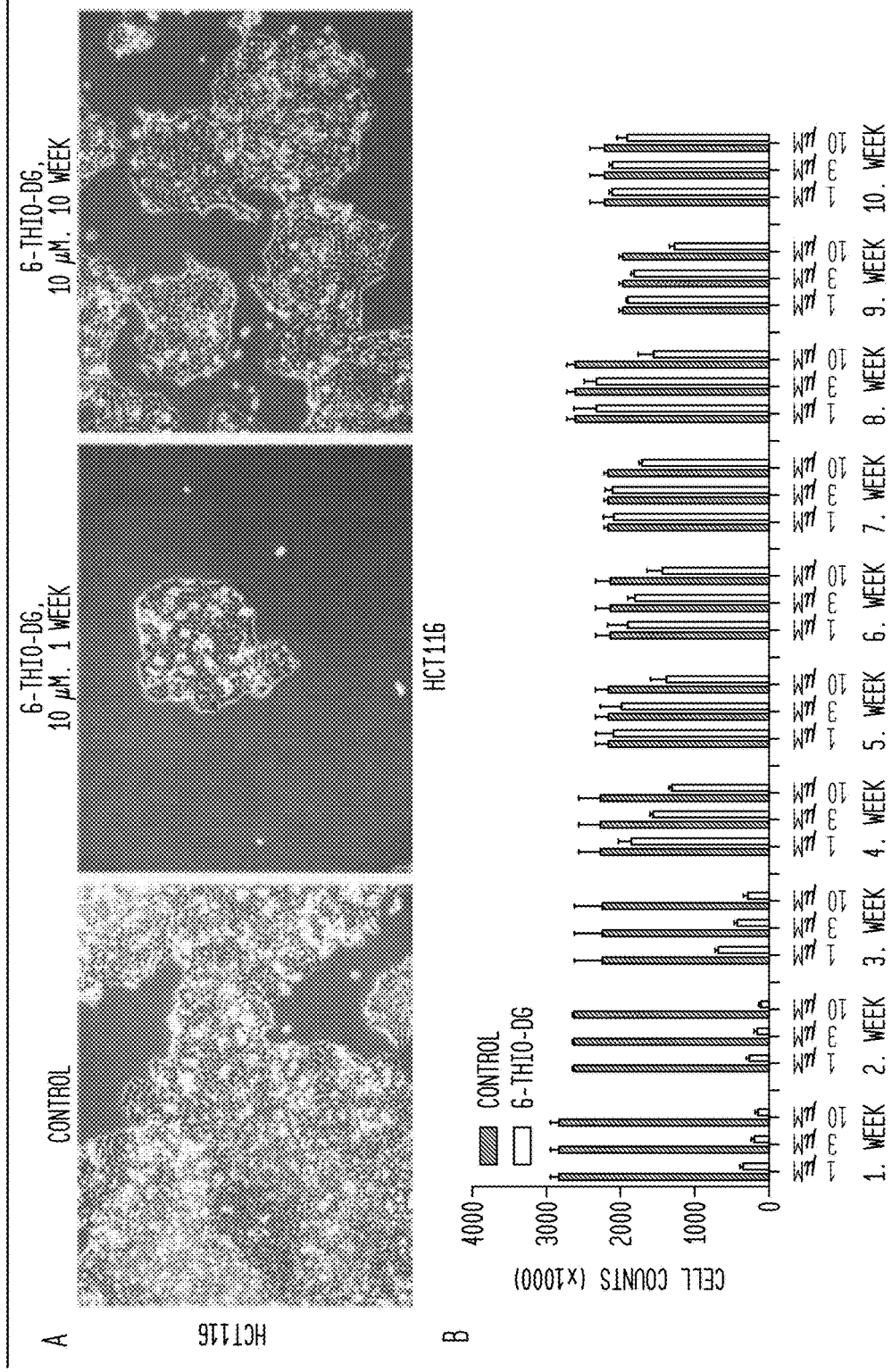
FIG. 21 shows data of acquired resistance to 6-thio-dG of HCT116 cells after long term treatment.

HCT116 cell, which have initial sensitivity to 6-thio-dG treatment, are capable of acquiring resistance. FIG. 21A shows light microscopy images of HCT116 cells under different treatment conditions. The left (control) panel shows a representative image of HCT116 cells cultured for 1 week while being treated with 1:1 diluted DMSO:water mixture, and having normal adherent growth. The middle panel (6-thio-dG) shows a representative image of the growth pattern of cells after treatment with 10 μM 6-thio-dG for 1 week, with notably fewer cells than control. The right panel (6-thio-dG) shows a representative image of the growth of HCT116 cells after treatment with 10 μM 6-thio-dG for 10 weeks, showing continued cell growth.

FIG. 21B shows the quantification of cell growth for HCT116 cells cultured with various concentrations of 6-thio-dG or control, for each week over the 10 week duration. The data shows that for all concentrations of 6-thio-dG (1 μM, 3 μM, and 10 μM), the HCT116 cells begin to acquire resistance to the treatment by the third week. Resistance then continues through week 10.

Figure 22:
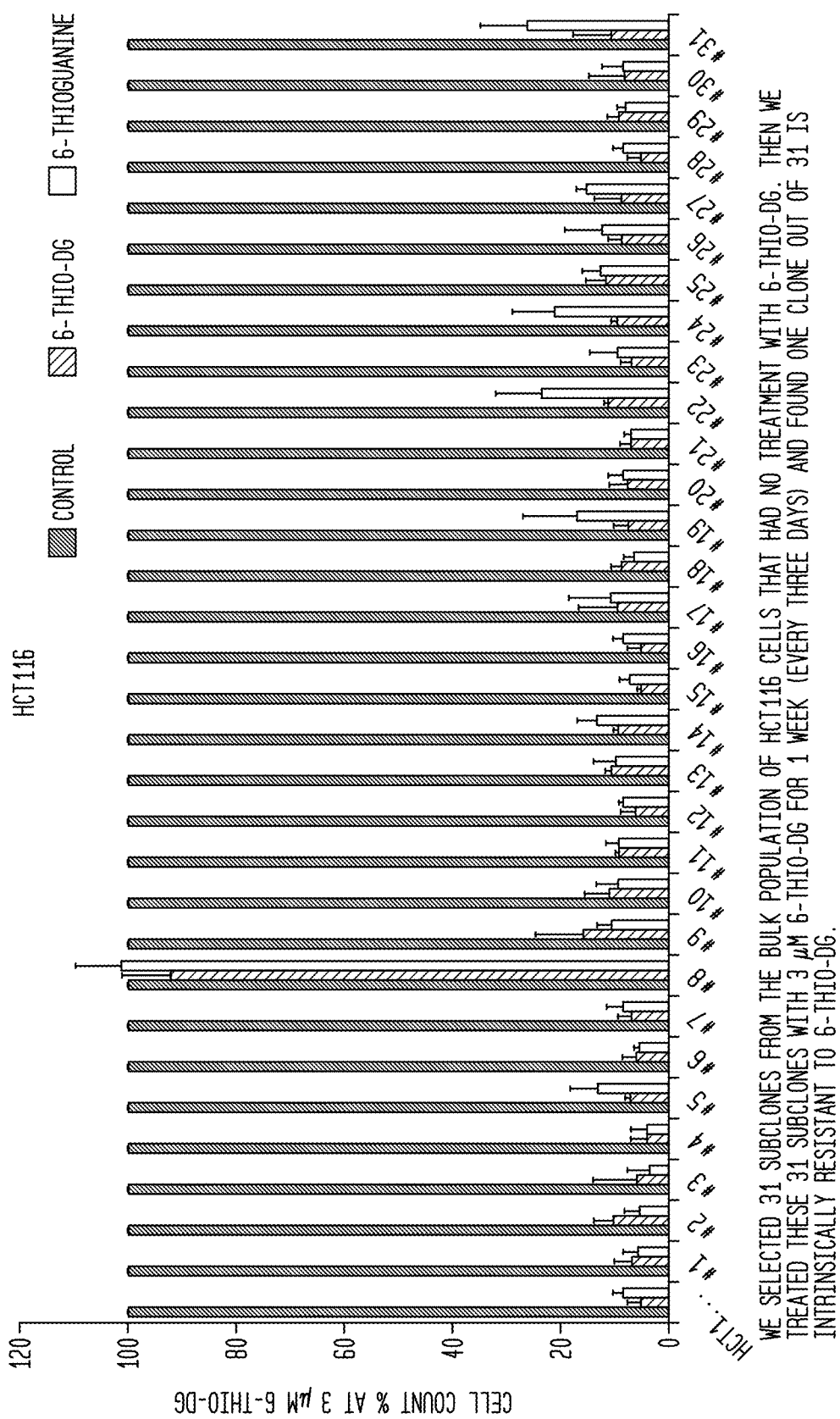
FIG. 22 depicts data showing generation of intrinsically resistant HCT116 clones that previously had no 6-thio-dG treatment. 31 sub clone cell lines were treated with 3 uM 6-thio-dG every three days for one week. At the end of the treatment, a cell count was performed and cell percentages relative to controls were determined. On clone (#8) was intrinsically resistant during some point of the sub cloning.

In a separate experiment, 31 sub clone cell lines were derived from HCT116 cells that had no prior treatment with 6-thio-dG. Each of the 31 sub clones were then treated with 3 μM 6-thio-dG, 6-thioguanine, or 1:1 diluted DMSO:water mixture as a control every three days for one week. At the end of one week, a cell count was performed of treated cells and cell percentage calculated relative to control cell count (FIG. 22). The results show that one clone (#8) became intrinsically resistant to 6-thio-dG treatment at some point during the sub cloning.

Four of the sub clone cell lines were further studied for resistance to 6-thio-dG. Clone numbers 31, 8, 15, and 5, were treated with 3 µM 6-thio-dG for 4 weeks. HCT116 Control group represent the main population treated with DMSO:water for 1-4 weeks. At the end of 4 weeks a cell count was performed to quantify cell growth. Sub clone #31, which was originally sensitive to 6-thio-dG treatment, acquired resistance and by week 4 showed cell growth indistinguishable from controls. Clone #8, which had intrinsic resistance prior to any 6-thio-dG treatment, maintained resistance for the duration of the treatment. Clones #15 and #5 each showed initial sensitivity to the 6-thio-dG treatments, and remained sensitive for the duration of the experiment. (FIG. 23)

In another separate experiment, three parental cell lines and their concomitant paclitaxel/carboplatin resistant lines were tested for sensitivity to 6-thio-dG. The parental cell lines HCC4017 (FIG. 24A), H1693 (FIG. 24B), H1819 (FIG. 24C) were treated in vitro with paclitaxel/carboplatin double therapy in clinically relevant 2:3 ratio for 5-6 cycles with increasing doses to develop resistant cell lines. The resulting resistant lines and their parents were tested for the effect of 6-thio-dG at 1, 3, and 10 µM concentrations. The HCC4017 paclitaxel/carboplatin resistant cell line was still sensitive to 6-thio-dG, showing that the genes responsible for acquisition of paclitaxel/carboplatin resistance are not necessarily responsible for the acquisition of 6-thio-dG resistance.

Gene expression differences of parental and paclitaxel/carboplatin resistance cell lines were examined (FIG. 25). Briefly, approximately 5 µg of total cellular RNA was isolated from each cell line and reverse transcribed into cDNA using standard techniques. The cDNA was then indirectly labeled with a fluorescent probe using a two-step hybridization and labeling protocol where the gene chip (Illumina Human WG-6 V3, Cat No: BD101-0201, BD-101-0603) was hybridized to cDNA overnight, washed stringently, and then post-stained with fluorescent dendrimers. After hybridization and washes, the gene chip was scanned using Illumina TotalPrep Kit (Ambion) Cat No: AMIL1791 and then arrays were scanned using Illumina Beadstation 500 BeadArray reader and data acquisitioned with Bead-Studio (Illumina) for visualization and data mining. Statistically significant genes were determined using unpaired t-tests with multiple testing correction via the Bonferroni method (p<0.01).

2652 genes were identified as having differential expression greater than 0.01 cutoff using unpaired t-tests with multiple testing correction via the Bonferroni method. A heat map graphical representation of the data is depicted in FIG. 25. The cell lines that were known to be resistant to 6-thio-dG were grouped as indicated in FIG. 25 (labeled "resistant"). Sensitive cell lines for 6-thio-dG are also noted.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for treating a resistant non-small cell lung cancer that is telomerase positive, the patient population being characterized by relapse of the cancer within six months of a first line anti-cancer agent, the method comprising administering to the subject
   (a) a first amount or dose of 6-thio-2'-deoxyguanosine and
   (b) a second amount or dose of an anti-cancer agent,
   wherein the first and second amounts or doses together comprise a therapeutically effective amount of a combination;
   wherein the combination is effective to:
      reduce size of a tumor, reduce growth rate of a tumor, reduce incidence of metastasis, promote an immune response, reduce progression of the cancer, increase lifespan of the subject, or a combination thereof; and
   wherein the anti-cancer agent is an EGFR inhibitor and said non-small cell lung cancer is EGFR resistant prior to treatment with said 6-thio-2'-deoxyguanosine.

2. The method according to claim 1, wherein the non-small cell lung cancer comprises a solid tumor comprising tumor cells, a metastatic cancer comprising metastatic tumor cells, or a combination thereof.

3. The method according to claim 1, wherein the amount or dose of 6-thio-2'-deoxyguanosine is about 0.5 mg/kg to about 3 mg/kg.

4. The method according to claim 1, wherein the combination is administered intravenously or orally.

5. The method according to claim 1, wherein the combination is administered by intratumoral injection.

6. The method according to claim 1, wherein the subject is a human being.

7. The method according to claim 1, wherein the combination produces an additive effect.

8. The method according to claim 1, wherein the combination produces a synergistic effect.

* * * * *